(12) United States Patent
Pfeifer et al.

(10) Patent No.: US 8,246,954 B2
(45) Date of Patent: Aug. 21, 2012

(54) METHODS OF TREATING AMYLOIDOSIS WITH HUMANIZED ANTI-BETA-AMYLOID ANTIBODIES

(75) Inventors: Andrea Pfeifer, St.-Légier (CH); Maria Pihlgren, St. Sulpice (CH); Andreas Muhs, Pully (CH); Ryan Watts, San Mateo, CA (US)

(73) Assignees: AC Immune S.A., Lausanne (CH); Genentech, Inc., South San Francisco, CA (US)

( * ) Notice: Subject to any disclaimer, the term of this patent is extended or adjusted under 35 U.S.C. 154(b) by 112 days.

(21) Appl. No.: 12/460,747

(22) Filed: Jul. 23, 2009

(65) Prior Publication Data

US 2010/0080800 A1 Apr. 1, 2010

Related U.S. Application Data

(63) Continuation of application No. 11/777,777, filed on Jul. 13, 2007, now Pat. No. 7,892,544.

(60) Provisional application No. 60/943,499, filed on Jun. 12, 2007.

(30) Foreign Application Priority Data

Jul. 14, 2006 (EP) .................................. 06014730
Oct. 2, 2006 (EP) .................................. 06020765

(51) Int. Cl.
*A61K 39/395* (2006.01)
(52) U.S. Cl. ................. 424/133.1; 424/139.1; 514/17.8
(58) Field of Classification Search ........................ None
See application file for complete search history.

(56) References Cited

U.S. PATENT DOCUMENTS

| | | | |
|---|---|---|---|
| 4,666,829 A | 5/1987 | Glenner et al. |
| 5,218,100 A | 6/1993 | Muller-Hill et al. |
| 5,231,000 A | 7/1993 | Majocha et al. |
| 5,231,170 A | 7/1993 | Averback |
| 5,234,814 A | 8/1993 | Card et al. |
| 5,262,332 A | 11/1993 | Selkoe |
| 5,441,870 A | 8/1995 | Seubert et al. |
| 5,538,845 A | 7/1996 | Knops et al. |
| 5,567,720 A | 10/1996 | Averback |
| 5,589,154 A | 12/1996 | Anderson |
| 5,593,846 A | 1/1997 | Schenk et al. |
| 5,605,811 A | 2/1997 | Seubert et al. |
| 5,624,821 A | 4/1997 | Winter et al. |
| 5,665,355 A | 9/1997 | Primi |
| 5,679,531 A | 10/1997 | Konig |
| 5,688,651 A | 11/1997 | Solomon |
| 5,693,753 A | 12/1997 | Konig |
| 5,705,401 A | 1/1998 | Masters et al. |
| 5,721,130 A | 2/1998 | Seubert et al. |
| 5,750,349 A | 5/1998 | Suzuki et al. |
| 5,766,846 A | 6/1998 | Schlossmacher et al. |
| 5,773,218 A | 6/1998 | Gallatin et al. |
| 5,786,180 A | 7/1998 | Konig |
| 5,955,285 A | 9/1999 | Averback |
| 5,955,317 A | 9/1999 | Suzuki et al. |
| 6,018,024 A | 1/2000 | Seubert et al. |
| 6,114,133 A | 9/2000 | Seubert et al. |
| 6,214,973 B1 | 4/2001 | Ohtomo et al. |
| 6,218,506 B1 | 4/2001 | Krafft et al. |
| 6,274,603 B1 | 8/2001 | Poirier |
| 6,284,221 B1 | 9/2001 | Schenk et al. |
| 6,287,793 B1 | 9/2001 | Schenk et al. |
| 6,294,171 B2 | 9/2001 | McMichael |
| 6,303,567 B1 | 10/2001 | Findeis et al. |
| 6,309,892 B1 | 10/2001 | Averback |
| 6,387,674 B1 | 5/2002 | Trasciatti et al. |
| 6,582,945 B1 | 6/2003 | Raso |
| 6,610,493 B1 | 8/2003 | Citron et al. |
| 6,664,442 B2 | 12/2003 | McConlogue et al. |
| 6,737,056 B1 | 5/2004 | Presta |
| 6,743,427 B1 | 6/2004 | Schenk |
| 6,750,324 B1 | 6/2004 | Schenk |
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |

(Continued)

FOREIGN PATENT DOCUMENTS

CL 3485-2006 12/2006

(Continued)

OTHER PUBLICATIONS

Mitchell et al. Curr Drug Targets. 2007; 8(7):832-838.*
Vickers JC. Drugs Aging. 2002; 19(7):487-494.*
U.S. Appl. No. 11/637,213, filed Dec. 11, 2006, Greferath et al.
U.S. Appl. No. 11/777,777, filed Jul. 13, 2007, Pfeifer et al.
U.S. Appl. No. 12/138,372, filed Jun. 12, 2008, Pfeifer et al.
U.S. Appl. No. 12/213,006, filed Jun. 12, 2008, Pfeifer et al.
U.S. Appl. No. 12/213,007, filed Jun. 12, 2008, Pfeifer et al.
U.S. Appl. No. 12/460,747, filed Jul. 23, 2009, Pfeifer et al.
Acha-Orbea et al., 1993, "Anti-T-cell receptor V beta antibodies in autoimmunity", Immunol Ser; 59:193-202.

(Continued)

*Primary Examiner* — Bridget E Bunner
*Assistant Examiner* — Kimberly A Ballard
(74) *Attorney, Agent, or Firm* — Jones Day

(57) ABSTRACT

The present invention is related to chimeric and humanized antibody and to methods and compositions for the therapeutic and diagnostic use in the treatment of amyloidosis, a group of disorders and abnormalities associated with amyloid protein such as Alzheimer's disease.

57 Claims, 33 Drawing Sheets

U.S. PATENT DOCUMENTS

Figures 1, 2:
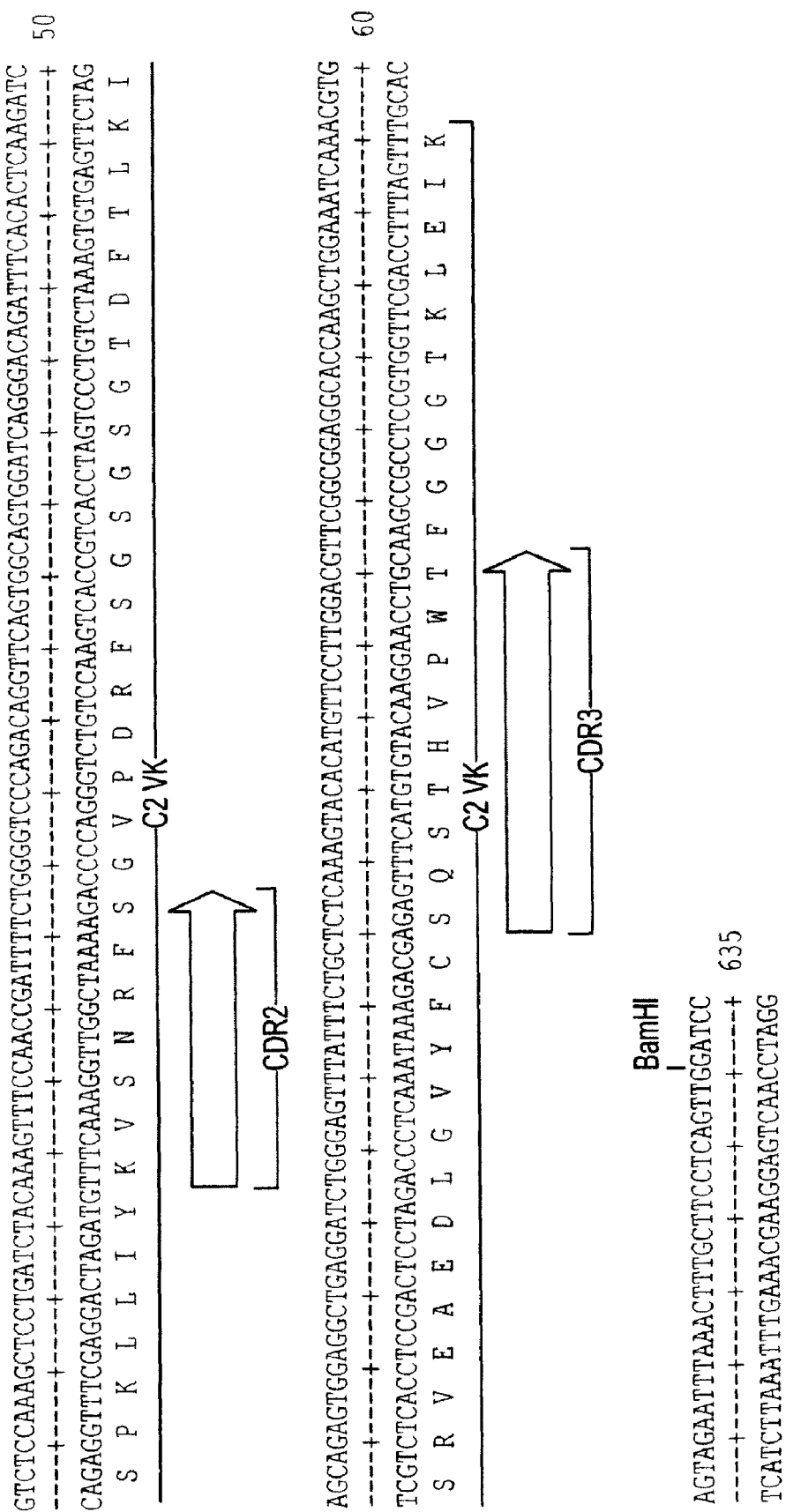
Figure 2:
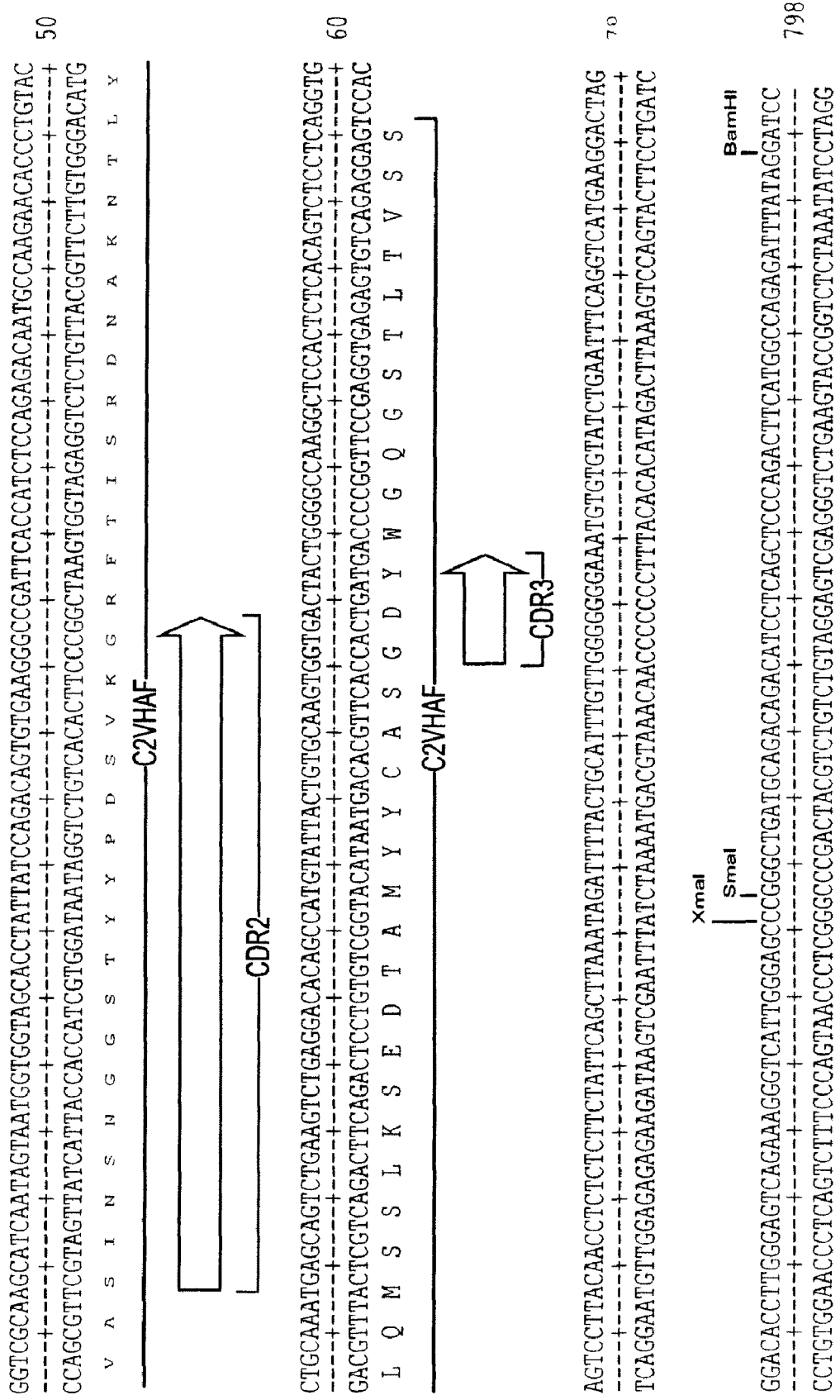

| | | |
|---|---|---|
| 6,905,686 B1 | 6/2005 | Schenk |
| 6,913,745 B1 | 7/2005 | Schenk |
| 6,972,127 B2 | 12/2005 | Schenk |
| 6,998,124 B1 | 2/2006 | Erickson-Miller et al. |
| 7,014,855 B2 | 3/2006 | Schenk |
| 7,022,500 B1 | 4/2006 | Queen et al. |
| 7,060,270 B2 | 6/2006 | Nicolau et al. |
| 7,067,133 B2 | 6/2006 | Nicolau |
| 7,129,084 B2 | 10/2006 | Bulow et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,318,923 B2 | 1/2008 | Tsurushita et al. |
| 7,320,790 B2 | 1/2008 | Hinton et al. |
| 7,332,581 B2 | 2/2008 | Presta |
| 7,335,491 B2 | 2/2008 | Drapeau et al. |
| 7,339,035 B2 | 3/2008 | Yanagisawa et al. |
| 7,371,365 B2 | 5/2008 | Poduslo et al. |
| 7,413,884 B2 | 8/2008 | Raso |
| 7,427,342 B2 | 9/2008 | Barber |
| 7,625,560 B2 | 12/2009 | Basi et al. |
| 7,772,375 B2 | 8/2010 | Greferath et al. |
| 7,892,544 B2 | 2/2011 | Pfeifer et al. |
| 8,048,420 B2 | 11/2011 | Pfeifer et al. |
| 8,124,353 B2 | 2/2012 | Pfeifer et al. |
| 2001/0029293 A1 | 10/2001 | Gallatin et al. |
| 2002/0009445 A1 | 1/2002 | Du et al. |
| 2002/0086847 A1 | 7/2002 | Chain |
| 2002/0094335 A1 | 7/2002 | Chalifour et al. |
| 2002/0182660 A1 | 12/2002 | Fong |
| 2002/0197258 A1 | 12/2002 | Ghanbari et al. |
| 2003/0068316 A1 | 4/2003 | Klein et al. |
| 2003/0108551 A1 | 6/2003 | Nicolau |
| 2003/0147882 A1 | 8/2003 | Solomon et al. |
| 2003/0190689 A1 | 10/2003 | Crosby et al. |
| 2003/0232758 A1 | 12/2003 | St. George-Hyslop et al. |
| 2004/0043416 A1 | 3/2004 | Ji et al. |
| 2004/0043418 A1 | 3/2004 | Holtzman et al. |
| 2004/0058414 A1 | 3/2004 | Queen et al. |
| 2004/0087777 A1 | 5/2004 | Basi et al. |
| 2004/0142872 A1 | 7/2004 | Poduslo et al. |
| 2004/0146512 A1 | 7/2004 | Rosenthal et al. |
| 2004/0175394 A1 | 9/2004 | Schenk et al. |
| 2004/0181042 A1 | 9/2004 | Yanagisawa et al. |
| 2004/0191264 A1 | 9/2004 | Nielsen et al. |
| 2004/0192898 A1 | 9/2004 | Jia et al. |
| 2004/0213800 A1 | 10/2004 | Seubett et al. |
| 2004/0223912 A1 | 11/2004 | Montalto et al. |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265919 A1 | 12/2004 | Vanderstichele et al. |
| 2005/0013815 A1 | 1/2005 | Schenk |
| 2005/0019330 A1 | 1/2005 | Schenk |
| 2005/0031651 A1 | 2/2005 | Gervais et al. |
| 2005/0118651 A1 | 6/2005 | Basi et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0147613 A1 | 7/2005 | Raso |
| 2005/0169925 A1 | 8/2005 | Bardroff et al. |
| 2005/0175626 A1 | 8/2005 | Delacourte et al. |
| 2006/0008458 A1 | 1/2006 | Solomon |
| 2006/0057646 A1 | 3/2006 | Wiltfang et al. |
| 2006/0057701 A1 | 3/2006 | Rosenthal et al. |
| 2006/0073149 A1 | 4/2006 | Bales et al. |
| 2006/0110388 A1 | 5/2006 | Davies et al. |
| 2006/0111301 A1 | 5/2006 | Mattner |
| 2006/0115477 A1 | 6/2006 | Unger et al. |
| 2006/0127954 A1 | 6/2006 | Mercken et al. |
| 2006/0160161 A1 | 7/2006 | Pavliakova et al. |
| 2006/0165682 A1 | 7/2006 | Basi et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0246075 A1 | 11/2006 | Mercken et al. |
| 2006/0280733 A1 | 12/2006 | Kayed et al. |
| 2006/0292152 A1 | 12/2006 | Rosenthal et al. |
| 2007/0010435 A1 | 1/2007 | Frangione et al. |
| 2007/0015218 A1 | 1/2007 | Cao et al. |
| 2007/0031416 A1 | 2/2007 | Shoji et al. |
| 2007/0072307 A1 | 3/2007 | Godavarti et al. |
| 2007/0098721 A1 | 5/2007 | Hillen et al. |
| 2007/0110750 A1 | 5/2007 | Glabe et al. |
| 2007/0128191 A1 | 6/2007 | Barrio |
| 2007/0166311 A1 | 7/2007 | Greferath et al. |
| 2007/0190046 A1 | 8/2007 | DeMattos et al. |
| 2007/0213512 A1 | 9/2007 | Krafft et al. |
| 2007/0218499 A1 | 9/2007 | Lambert et al. |
| 2008/0025988 A1 | 1/2008 | Yamaguchi et al. |
| 2008/0107601 A1 | 5/2008 | Lauwereys et al. |
| 2008/0131422 A1 | 6/2008 | Sugimura et al. |
| 2008/0199879 A1 | 8/2008 | Takayama et al. |
| 2008/0292639 A1 | 11/2008 | Shen et al. |
| 2009/0017040 A1 | 1/2009 | Pfeifer et al. |
| 2009/0017041 A1 | 1/2009 | Pfeifer et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0093002 A1 | 4/2009 | Pfeifer et al. |
| 2009/0155246 A1 | 6/2009 | Gellerfors et al. |
| 2009/0155249 A1 | 6/2009 | Pfeiffer et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Barghorn et al. |
| 2009/0191190 A1 | 7/2009 | Barghorn et al. |
| 2009/0214515 A1 | 8/2009 | Holzman et al. |
| 2009/0232801 A1 | 9/2009 | Hillen et al. |
| 2009/0238831 A1 | 9/2009 | Hillen et al. |
| 2010/0150906 A1 | 6/2010 | Pfeifer et al. |
| 2010/0291097 A1 | 11/2010 | Pfeifer et al. |
| 2010/0297012 A1 | 11/2010 | Pfeifer et al. |
| 2010/0297013 A1 | 11/2010 | Pfeifer et al. |
| 2010/0297132 A1 | 11/2010 | Greferath et al. |
| 2011/0070613 A1 | 3/2011 | Greferath et al. |
| 2011/0212109 A1 | 9/2011 | Barghorn et al. |

FOREIGN PATENT DOCUMENTS

| | | |
|---|---|---|
| CL | 2007-2070 | 7/2007 |
| CL | 2008-1741 | 6/2008 |
| CL | 2008-1742 | 6/2008 |
| CN | 1396183 | 2/2003 |
| EP | 0613007 | 8/1994 |
| EP | 0623675 | 11/1994 |
| EP | 0304013 | 6/1996 |
| EP | 0783104 | 7/1997 |
| EP | 1130032 | 9/2001 |
| EP | 1420032 | 5/2004 |
| EP | 1741783 | 1/2007 |
| EP | 1861422 | 12/2007 |
| EP | 1954718 | 8/2008 |
| EP | 1963363 | 9/2008 |
| EP | 1976877 | 10/2008 |
| JP | 07238096 | 9/1995 |
| JP | 2005 185281 | 7/2005 |
| JP | 2007077103 | 3/2007 |
| WO | WO 89/07657 | 8/1989 |
| WO | WO 90/05746 | 5/1990 |
| WO | WO 92/11018 | 7/1992 |
| WO | WO 95/11994 | 5/1995 |
| WO | WO 96/01359 | 1/1996 |
| WO | WO 96/28187 | 9/1996 |
| WO | WO 96/29605 | 9/1996 |
| WO | WO 96/03631 | 11/1996 |
| WO | WO 96/40731 | 12/1996 |
| WO | WO 97/10505 | 3/1997 |
| WO | WO 97/18476 | 5/1997 |
| WO | WO 97/21728 | 6/1997 |
| WO | WO 99/05175 | 2/1999 |
| WO | WO 99/27944 | 6/1999 |
| WO | WO 99/40837 | 8/1999 |
| WO | WO 99/40909 | 8/1999 |
| WO | WO 99/59571 | 11/1999 |
| WO | WO 00/56771 | 9/2000 |

| | | |
|---|---|---|
| WO | WO 00/72880 | 12/2000 |
| WO | WO 01/16364 | 3/2001 |
| WO | WO 01/18169 | 3/2001 |
| WO | WO 01/62801 | 8/2001 |
| WO | WO 01/85093 | 11/2001 |
| WO | WO 02/46237 | 6/2002 |
| WO | WO 02/096937 | 12/2002 |
| WO | WO 03/014162 | 2/2003 |
| WO | WO 03/016466 | 2/2003 |
| WO | WO 03/031475 A2 | 4/2003 |
| WO | WO 03/070760 | 8/2003 |
| WO | WO 03/076006 | 9/2003 |
| WO | WO 03/077858 | 9/2003 |
| WO | WO 03/090772 | 11/2003 |
| WO | WO 2004/024090 | 3/2004 |
| WO | WO 2004/029093 | 4/2004 |
| WO | WO 2004/031400 A2 | 4/2004 |
| WO | WO 2004/050707 | 6/2004 |
| WO | WO 2004/058258 | 7/2004 |
| WO | WO 2004/065569 | 8/2004 |
| WO | WO 2004/067561 | 8/2004 |
| WO | WO 2004/071408 | 8/2004 |
| WO | WO 2004/108895 | 12/2004 |
| WO | WO 2004/108895 A2 | 12/2004 |
| WO | WO 2005/005638 | 1/2005 |
| WO | WO 2005/018424 | 3/2005 |
| WO | WO 2005/025516 | 3/2005 |
| WO | WO 2005/053604 | 6/2005 |
| WO | WO 2005/058941 | 6/2005 |
| WO | WO 2005/081872 | 9/2005 |
| WO | WO 2005/105998 | 11/2005 |
| WO | WO 2005/120571 | 12/2005 |
| WO | WO 2006/016644 | 2/2006 |
| WO | WO 2006/036291 | 4/2006 |
| WO | WO 2006/037604 | 4/2006 |
| WO | WO 2006/039327 | 4/2006 |
| WO | WO 2006/055178 | 5/2006 |
| WO | WO 2006/066049 | 6/2006 |
| WO | WO 2006/066089 | 6/2006 |
| WO | WO 2006/066171 | 6/2006 |
| WO | WO 2006/081171 | 8/2006 |
| WO | WO 2006/083533 | 8/2006 |
| WO | WO 2006/083689 | 8/2006 |
| WO | WO 2006/094724 | 9/2006 |
| WO | WO 2006/103116 | 10/2006 |
| WO | WO 2006/118959 | 11/2006 |
| WO | WO 2006/121656 | 11/2006 |
| WO | WO 2007/011639 | 1/2007 |
| WO | WO 2007/017686 | 2/2007 |
| WO | WO 2007/022416 | 2/2007 |
| WO | WO 2007/042261 | 4/2007 |
| WO | WO 2007/050359 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/068412 | 6/2007 |
| WO | WO 2007/068429 | 6/2007 |
| WO | WO 2007/106617 | 9/2007 |
| WO | WO 2007/108756 | 9/2007 |
| WO | WO 2007/113172 | 10/2007 |
| WO | WO 2007/113172 A2 | 10/2007 |
| WO | WO 2007/123345 | 11/2007 |
| WO | WO 2008/002893 | 1/2008 |
| WO | WO 2008/011348 | 1/2008 |
| WO | WO 2008/012101 | 1/2008 |
| WO | WO 2008/030251 | 3/2008 |
| WO | WO 2008/045962 | 4/2008 |
| WO | WO 2008/060364 | 5/2008 |
| WO | WO 2008/061795 | 5/2008 |
| WO | WO 2008/067464 | 6/2008 |
| WO | WO 2008/070229 | 6/2008 |
| WO | WO 2008/071394 | 6/2008 |
| WO | WO 2008/104385 | 9/2008 |
| WO | WO 2008/104386 | 9/2008 |
| WO | WO 2008/110885 A2 | 9/2008 |
| WO | WO 2008/143708 | 11/2008 |
| WO | WO 2008/150946 | 12/2008 |
| WO | WO 2008/150946 A1 | 12/2008 |
| WO | WO 2008/150949 | 12/2008 |
| WO | WO 2008/156621 | 12/2008 |
| WO | WO 2008/156622 | 12/2008 |
| WO | WO 2009/048537 | 4/2009 |
| WO | WO 2009/048538 | 4/2009 |
| WO | WO 2009/048539 | 4/2009 |

OTHER PUBLICATIONS

Anderson et al., 2004, "Characterization of beta amyloid assemblies in drusen: the deposits associated with aging and age-related macular degeneration", Experimental Eye Research; 78:243-256.

Bard et al., 2000, "Peripherally administered antibodies against amyloid bipeptide enter the central nervous system and reduce pathology in a mouse model of Alzheimer disease", Nature Med.; 6:916-919.

Bard et al., 2003, "Epitope and isotype specificities of antibodies to beta-amyloid peptide for protection against Alzheimer's disease-like neuropathology", Proc Natl Acad Sci USA; 100(4): 2023-2028.

Barghorn et al., 2005, "Globular amyloid beta-peptide 1-42 oligomer—a homogeneous and stable neuropatholgical protein in Alzheimer's disease", J Neurochem; 95(31):834-847.

Written Opinion of International Application No. PCT/US2007/073504, dated May 14, 2008.

Barrow et al., 1992, "Solution conformations and aggregational properties of synthetic amyloid beta-peptides of Alzheimer's disease. Analysis of circular dichroism spectra", J. Mol. Biol.; 225:1075-1093.

Campbell et al., 1984, "General properties and applications of monoclonal antibodies", Elsevier Science Publishers B.V., pp. 1-32.

Celli et al., 1998, "Origin and pathogenesis of antiphospholipid antibodies", Braz J Med Biol Res; 31(6):723-732.

Database EMBL [Online], 1988, "Mouse innunoglobulin rearranged kappa-chain V-region V105 gene from C.AL20-TEPC-105 myeloma, exons 1 and 2", retrieved from EBI accession No. EMBL:M12183 Database accession No. M12183.

Database EMBL [Online], 1999, "*Mus musculus* F5.20G3 low-affinity anti-phosphorylcholine IgG antibody mRNA, partial cds", retrieved from EBI accession No. EMBL:AF044238 Database accession No. AF044238.

Database Geneseq [Online], 1988, "L chain subunit of FAS specific antibody coding sequence", retrieved from EBI accession No. GSN:AAT88870 Database accession No. AAT88870.

Database Geneseq [Online], 1999, "Anti-human FAS monoclonal antibody CH11 light chain cDNA", retrieved from EBI accession No. GSN:AAV66736 Database accession No. AAV66736.

Database Geneseq [Online], 2003, "Mouse DNA encoding antibody 3D8 heavy chain variable region", retrieved from EBI accession No. GSN:ABX16569 Database accession No. ABX16569.

Database Geneseq [Online], 2005, "Humanized monoclonal antibody Hu4785-2 heavy chain", retrieved from EBI accession No. GSP:ADX39139 Database accession No. ADX39139.

Database Geneseq [Online], 2005, "Humanized monoclonal antibody Hu4785-2 VH region", retrieved from EBI accession No. GSP:ADX39143 Database accession No. ADX39143.

Database Geneseq [Online], 2005, "Humanized monoclonal antibody Hu4785-2 partial protein", retrieved from EBI accession No. GSP:ADX39104 Database accession No. ADX39104.

Database Geneseq [Online], 2005, "Mouse monoclonal antibody 4785 heavy chain SEQ ID 38", retrieved from EBI accession No. GSP:ADX39137 Database accession No. ADX39137.

Database Geneseq [Online], 2005, "Mouse monoclonal antibody 4785 heavy chain SEQ ID 1", retrieved from EBI accession No. GSP:ADX39100 Database accession No. ADX39100.

Database NCBI Protein [Online] dated Apr. 11, 1996, accession No. AAA96779.

Database NCBI Protein [Online] dated Aug. 30, 1993, accession No. AAA38584.

Database NCBI Protein [Online] dated Mar. 23, 2002, accession No. AAL92941.

Database NCBI Protein [Online] dated Mar. 23, 2002, accession No. AAL92933.

David et al., 1991, "A significant reduction in the incidence of collagen induced arthritis in mice treated with anti-TCRV-beta antibodies", J Cell Biochem; Suppl. 15E, p. 179.

De Giorgi et al., 1993, "Induction of foetal lethality in AKR offspring after repeated inoculations into AKR females of anti-TCR/V beta 6 monoclonal antibody", Res Immunol; 144(4):245-255.

Di Giorgi et al., 1993, "Murine hybridomas secreting monoclonal antibodies reacting with MIsa antigens", Exp Clin Immunogenet; 10(4):219-223.

Demattos et al., 2001, "Peripheral anti-Aβ antibody alters CNS and plasma Aβ clearance and decreases brain Aβ burden in a mouse model of Alzheimer's disease", Proc Natl Acad Sci USA; 98:8850-8855.

Dorronsoro et al., 2003, "Peripheral and dual binding site inhibitors of acetylcholinesterase as neurodegenerative disease-modifying agents", Expert Opin Ther Pat; 13(11):1725-1732.

European Office Action of European application No. 06829456.0-2402, dated Dec. 23, 2008.

Frenkel et al., 2000, "Modulation of Alzheimer's beta-amyloid neurotoxicity by site-directed single-chain antibody", J Neuroimmunol; 106(1-2):23-31.

Fujimuro et al., 1994, "Production and characterization of monoclonal antibodies specific to multi-ubiquitin chains of polyubiquitinated proteins", FEBS; 349:173-180.

Fujimuro et al., 2005, "Production of antipolyubiquitin monoclonal antibodies and their use for characterization and isolation of polyubiquitinated proteins", Meth Enzymol; 399:75-86.

Fukuchi et al., 2006, "Amelioration of amyloid load by anti-Abeta single-chain antibody in Alzheimer mouse model", Biochem Biophys Res Commun; 344(1):79-86.

Hicke, 2001, "Protein regulation by monoubiquitin", Nat Rev; 2:196-201.

International Preliminary Report on Patentability of International application No. PCT/US2007/073504, dated Jan. 22, 2009.

International Search Report for International Application No. PCT/EP2006/011862, dated Jun. 12, 2007.

International Search Report for International Application No. PCT/US2007/073504, dated May 14, 2008.

Johnson-Wood et al., 1997, "Amyloid precursor protein processing and A beta42 deposition in a transgenic mouse model of Alzheimer disease", Proc. Natl. Acad. Sci. USA; 94(4):1550-1555.

Jung et al., 1996, "Alzheimer's beta-amyloid precursor protein is expressed on the surface of immediately ex vivo brain cells: a flow cytometric study", J. Neurosci. Res.; 46(3):336-348.

Kim et al., 2004, "Development of conformation-specific antibodies for neutralization of beta-amyloid oligomers", Neurobiol Aging; 25(1):S145, P1-175 Abstract.

Kisilevsky et al., 1995, "Arresting amyloidosis in vivo using small-molecule anionic sulphonates or sulphates: Implications for Alzheimer's disease", Nat Med; 1(2):143-148.

Kisilevsky, 1996, "Anti-amyloid drugs potential in the treatment of diseases associated with aging", Drugs Aging; 8(2):75-83.

Klein et al., 2002, "Abeta toxicity in Alzheimer's disease: globular oligomers (ADDLs) as new vaccine and drug targets", Neurochem Int; 41(5):345-352.

Lambert et al., 2007, "Monoclonal antibodies that target pathological assemblies of Abeta", J Neurochem; 100(1): 23-35.

Langdon et al., 2000, "Germline sequences of $V_H$7183 gene family members in C57BL/6 mice demonstrate natural selection of particular sequences during recent evolution", Immunogen; 51:241-245.

Lee et al., 2002, "Molecular cloning of agonistic and antagonistic monoclonal antibodies against human 4-IBB", Eur J Immunogenet; 29(5):449-452.

Levine et al., 2002, "4,4'-dianilino-1,1'-binaphthyl-5-disulfonate (bis-ANS) reports on non-β-sheet conformers of Alzheimer's peptide β(1-40)", Arch Biochem Biophys; 404:106-115.

Liu Ruitian et al., 2004, "Single chain variable fragments against beta-amyloid (Abeta) can inhibit Abeta aggregation and prevent Abeta-induced neurotoxicity", Biochem; 43(22):6959-6967.

Lund et al., 1995, "Oligosaccharide-protein interactions in IgG can modulate recognition by Fc-gamma receptors", FASEB J; 9(1):115-119.

McLaurin et al., 2002, "Therapeutically effective antibodies against amyloid-beta peptide target amyloid-beta residues 4-10 and inhibit cytotoxicity and fibrillogenesis", Nat Med; 8(11):1263-1269.

Moretto et al., 2007, "Conformation-sensitive antibodies against Alzheimer amyloid-beta by immunization with a thioredoxin-constrained B-cell epitope peptide", J Biol Chem; 282(15):11436-11445.

Nemes et al., 2004, "Cross-linking of ubiquitin, HSP27, parkin, and α-synuclein by γ-glutamyl-ε-lysine bonds in Alzheimer's neurofibrillary tangles", FASEB J; 18:1135-37.

Nicolau et al., 2002, "A liposome-based therapeutic vaccine against beta-amyloid plaques on the pancreas of transgenic norba mice", Proc Natl Acad Sci USA; 99(4): 2332-2337.

Office Action dated Apr. 27, 2009 of U.S. Appl. No. 11/637,213.
Office Action dated Aug. 31, 2009 of U.S. Appl. No. 11/637,213.
Office Action dated Feb. 17, 2009 of U.S. Appl. No. 11/637,213.
Office Action dated Sep. 1, 2009 of U.S. Appl. No. 12/138,372.
Office Action dated Sep. 11, 2009 of U.S. Appl. No. 11/637,213.
Office Action dated Aug. 10, 2009 of U.S. Appl. No. 11/777,777.
Office Action dated Jan. 27, 2010 of U.S. Appl. No. 11/777,777.
Office Action dated May 5, 2010 of U.S. Appl. No. 11/777,777.
Office Action dated Jul. 1, 2010 of U.S. Appl. No. 11/777,777.
Office Action dated Oct. 10, 2010 of U.S. Appl. No. 11/777,777.
Office Action dated Jan. 12, 2011 of U.S. Appl. No. 11/777,777.

Padlan et al., 1989, "Structure of an antibody-antigen complex: crystal structure of the HyHEL-10 Fab-lysozyme complex", Proc Natl Acad Sci USA; 86(15):5938-42.

Paul eds., 1993, "Fv structure and diversity in three dimensions", Fundamental Immunology; 292-295.

Racke et al., 2005, "Exacerbation of cerebral amyloid angiopathy-associated microhemorrhage in amyloid precursor protein transgenic mice by immunotherapy is dependent on antibody recognition of deposited forms of amyloid beta", J. Neurosci.; 25(3):629-636.

Rudikoff et al., 1982, "Single amino acid substitution altering antigen-binding specificity", Proc Natl Acad Sci USA; 79(6):1979-1983.

Ewert et al., 2003, "Biophysical properties of human antibody variable domains", J Mol Biol; 325:531-553.

Rzepecki et al., 2004, "Prevention of Alzheimer's disease-associated Aβ aggregation by rationally designed non-peptide β-sheet ligands", J Biol Chem; 279(46):47497-47505.

Schable et al., 1999, "Characteristics of the immunoglobulin V kappa genes, pseudogenes, relics and orphons in the mouse genome", Eur J Immunol; 29:2082-2086.

Schenk et al., 1999, "Immunization with amyloid-beta attenuates Alzheimer-disease-like pathology in the PDAPP mouse", Nature; 400:173-177.

International Search Report of International application No. PCT/US2000/014810, dated Dec. 15, 2000.

International Search Report of International application No. PCT/US2007/021134, dated Dec. 19, 2008.

Seubert et al., 1992, "Isolation and quantification of soluble Alzheimer's beta-peptide from biological fluids", Nature 359(6393):325-327.

Solomon et al., 1996, "Monoclonal antibodies inhibit in vitro fibrillar aggregation of the Alzheimer beta-amyloid peptide", Proc Natl Acad Sci USA;93:452-455.

Solomon et al., 1997, "Disaggregation of Alzheimer β-amyloid by site-directed mAb", Proc Natl Acad Sci USA; 94:4109-4112.

Soto et al., 1995, "The alpha-helical to beta-strand transition in the amino-terminal fragment of the amyloid beta-peptide modulates amyloid formation", J. Biol. Chem.; 270(7):3063-3067.

Tenno et al., 1994, "Structural basis for distinct roles of Lys63- and Lys48-linked polyubiquitin chains", Genes to Cells; 9:865-875.

Van Gool et al., 1994, "Concentrations of amyloid-beta protein in cerebrospinal fluid increase with age in patients free from neurodegenerative disease", Neurosci Let; 172(1-2):122-124.

Weaver-Feldhaus et al., 2004, "Yeast mating for combinatorial Fab library generation and surface display", FEBS Letters; 564(2):24-34.

Written Opinion of International Application No. PCT/US2007/021134, dated Dec. 19, 2008.

Ding et al., 2007, "Targeting age-related macular degeneration with Alzheimer's disease based immunotherapies: anti-amyloid-beta antibody attenuates pathologies in an age-related macular degeneration mouse model", Vision Research, Pergamon Press, Oxford, GB; 48(3):339-345.
Guo et al., 2007, "Targeting amyloid-beta in glaucoma treatment", Proc Natl Acad Sci USA; 104(33):13444-13449.
McKinnon et al., 2002, "Caspase activation and amyloid precursor protein cleavage in rat ocular hypertension", Invest Ophthamol & Vis Sci; 43(4):1077-1087.
MacCallum et al., 1996, "Antibody-antigen interactions: contact analysis and binding site topography", J Mol Biol; 262:732-745.
International Preliminary Report on Patentability of International application No. PCT/EP2006/011862, dated Jun. 26, 2008.
International Preliminary Report on Patentability of International application No. PCT/US2008/007317, dated Dec. 17, 2009.
International Preliminary Report on Patentability of International application No. PCT/US2008/007318, dated Dec. 17, 2009.
International Preliminary Report on Patentability of International application No. PCT/US2007/021134, dated Apr. 7, 2009.
International Search Report of International application No. PCT/US2008/011493, dated Oct. 12, 2009.
International Search Report of International application No. PCT/US2008/011492, dated Sep. 7, 2009.
International Search Report of International application No. PCT/US2008/011491, dated Sep. 20, 2009.
International Search Report of International application No. PCT/US2008/007317, dated Oct. 28, 2008.
International Search Report of International application No. PCT/US2008/007318, dated Nov. 21, 2008.
Written Opinion of International application No. PCT/US2008/011493, dated Oct. 12, 2009.
Written Opinion of International application No. PCT/US2008/011492, dated Sep. 7, 2009.
Written Opinion of International application No. PCT/US2008/011491, dated Sep. 20, 2009.
Written Opinion of International application No. PCT/EP2006/011862, dated Jun. 12, 2007.
Written Opinion of International application No. PCT/US2008/007318, dated Nov. 21, 2008.
Written Opinion of International application No. PCT/US2008/007317, dated Oct. 28, 2008.
"Staining of human Brain Sections with AC Immune's humanized ACI-01-Ab7 Antibody", Study ACI-Bonn-01, AC Immune, Sep. 26, 2006, pp. 1-4.
Piorkowska, K., and Pihlgren, M.,"Study ACI-ACI-2009.02; Binding of ACI-01-Ab-7C2 to plaques", AC Immune, 2009, pp. 1-3.
Pihlgren, M., "Study ACI-ACI-2009.03 Disaggregation of Abetal-42 fibers by ACI-01-Ab-7C2", AC Immune, 2009, pp. 1-4.
"Comparison of 8F5 and FP12H3-C2/ACI-01-Ab-7-C2 antibodies", AC Immune, Aug. 2009, pp. 1-3.
Pihlgren, M., "Binding of the murine monoclonal anti-Abeta antibody ACI-01-Ab7 to Abetal-42 monomers, oligomers, and fibers", AC Immune, 2006, pp. 1-4.
"Study to analyze the Binding of AC Immune's murine monoclonal Antibody ACI-01-Ab7 to Amyloid Species in ELISA", AC Immune, 2006, pp. 1-2.
"Studies to map the Epitope of AC Immune's monoclonal Antibody ACI-01-Ab7", AC Immune, 2006, pp. 1-5.
"Studies of Influence of Passive Vaccination with ACI-01-Ab7 on Memory Capacity in single transgenic hAPP Mice" AC Immune, 2006, pp. 1-3.
"Study to analyze the Binding of AC Immune's monoclonal Antibody ACI-01-Ab7 to Amyloid Species in Western Blot and Dot Blot", AC Immune, 2006, pp. 1-4.
Amendment and Response as filed on Jul. 27, 2009 in U.S. Appl. No. 11/637,213.
European Office Action of European Application No. 08768370.2-1222, dated May 3, 2010.
Ward et al., 1989, "Binding activities of a repertoire of single immunoglobulin variable domains secreted from *Escherichia coli*", Letters to Nature; 341(12):544-546.
Pereira et al., 1998, "Cardiolipin binding a light chain from lupus-prone mice", Biochemistry; 37(5):1430-1437.

Van Den Beucken et al., 2001, "Building novel binding ligands to B7.1 and B7.2 based on human antibody single variable light chain domains", J Mol Biol; 310:591-601.
Davies et al., 1995, "Antibody VH domains as small recognition units", Biotechnology;13:475-479.
Dumoulin et al., 2002, "Single-domain antibody fragments with high conformational stability", Protein Sci; 11:500-515.
Klimka et al., 2000, "Human anti-CD30 recombinant antibodies by guided phage antibody selection using cell panning", Brit J Cancer; 83(2):252-260.
Marks et al., 1992, "By-passing immunization: Building high affinity human antibodies by chain shuffling", Biotechnology; 10:779-783.
Portolano et al., 1993, "Lack of promiscuity in autoantigen-specific H and L chain combination as revealed by human H and L chain roulette", J Immunol; 150(3):880-887.
Clackson et al., 1991, "Making antibody fragments using phage display libraries", Nature; 352(15):624-328.
Rader et al., 1998, "A phage display approach for rapid antibody humanization:designed combinatorial V gene libraries", Proc Natl Acad Sci USA; 95:8910-8915.
International Preliminary Report on Patentability of application No. PCT/US2008/011491, dated Apr. 15, 2010.
International Preliminary Report on Patentability of application No. PCT/US2008/011492, dated Apr. 15, 2010.
International Preliminary Report on Patentability of application No. PCT/US2008/011493, dated Apr. 15, 2010.
Notice of Allowance and Fees Due of U.S. Appl. No. 11/637,213, dated Dec. 14, 2009.
Blond et al., 1987, "Partly native epitopes are already present on early intermediates in the folding of trytophan synthase", Proc Natl Acad Sci USA; 84:1147-1151.
Burdick et al., 1992, "Assembly and aggregation properties of synthetic Alzheimer's A4/beta amyloid peptide analogs", J Biol Chem; 267:546-554.
Dewachter et al., 2000, "Aging increased amyloid peptide and caused amyloid plaques in brain of old APP/V717I transgenic mice by a different mechanism than mutant presenilin 1", J Neurosci; 20:6452-6458.
Dewachter et al., 2002, "Neuronal deficiency of presenilin 1 inhibits amyloid plaque formation and corrects hippocampal long-term potentiation but not a cognitive defect of amyloid precursor protein [V717I] transgenic mice", J Neurosci; 22:3445-3453.
Glenner et al., 1984, "Alzheimer's disease: initial report of the purification and characterization of a novel cerebrovascular amyloid protein", Biochem Biophys Res Comm; 129:885-890.
Heneka et al., 2005, "Focal glial activation coincides with increased with increased BACE1 activation and precedes amyloid plaque deposition in APP[V717I] transgenic mice", J Neuroinflammation; 2:22.
Kirschner et al., 1986, "X-ray diffraction from intraneuronal paired helical filaments and extraneuronal amyloid fibers in Alzheimer disease indices cross-beta conformation", Proc Natl Acad Sci USA; 83:503-507.
Khaw et al., 1982, "Technetium-99m labeling of antibodies to cardiac myosin fab and to human fibrinogen", J Nucl Med; 23:1011-1019.
McGreer et al., 1994, "Pathological proteins in senile plaques", Tohoku J Exp Med; 174:269-277.
Moechars et al., 1999, "Early phenotypic changes in transgenic mice that overexpress different mutants of amyloid precursor protein in brain", J Biol Chem; 274:6483-6492.
Nelson et al., 2006, "Recent atomic models of amyloid fibril structure", Curr Opin Struct Biol; 16:260-265.
Petkova et al., 2004, "Solid state NMR reveals a pH-dependent antiparallel β-sheet registry in fibrils formed by a β-amyloid peptide", J Mol Biol; 335:247-260.
Petkova et al., 2002, "A structural model for Alzheimer's β-amyloid fibrils based on experimental constraints from solid state NMR", Proc Natl Acad Sci USA; 99:16742-16747.
Singapore Written Opinion of Singaporean application No. 200900163-7, dated Nov. 6, 2009.
Van Der Auwera et al., 2005, "A ketogenic diet reduces amyloid beta 40 and 42 in a mouse model of Alzheimer's disease", Nutr Metab (Lond); 2:28.

Gulf Cooperation Council Office Action of GCC application No. GCC/P/2006/7389, dated Mar. 5, 2010.
Office Action of European application No. 08768371.0-2406, dated Jun. 28, 2010.
Solomon, 2007, "Beta-amyloid based immunotherapy as a treatment of Alzheimer's disease", Drugs of Today; 43(5):333-342.
Smith et al., 1995, "Determination of helix-helix interactions in membranes by rotational resonance NMR", Proc Natl Acad Sci USA; 92:488-491.
Notice of Allowance of U.S. Appl. No. 11/777,777, dated Jul. 30, 2010.
Russian Office Action of Russian application No. 2008128139, dated Jul. 13, 2010.
European Office Action of European application No. 06829456.0-2402, dated Jul. 30, 2010.
Hanan et al., 1996, "Inhibitory effect of monoclonal antibodies on Alzheime's β-amyloid peptide aggregation", Amyloid: Int J Exp Clin Invest; 3:130-133.
Office Action of U.S. Appl. No. 12/213,006, dated Jun. 7, 2010.
Office Action of U.S. Appl. No. 12/213,007, dated Jun. 4, 2010.
Singapore Office Action of Singaporean patent application No. 200804129-5, dated Aug. 23, 2010, with Examination Report, dated Jun. 9, 2010.
Sergeant, 2003, "Truncated beta-amyloid peptide species in pre-clinical Alzheimer's disease as new targets for the vaccination approach", J Neurochem; 85(6):1581-91.
Russian Office Action (translation) of Russian application No. 2009104769, dated Feb. 15, 2011.
Office Action of U.S. Appl. No. 12/213,006, dated Nov. 15, 2010.
Casset et al., 2003, "A peptide mimetic of an anti-CD4 monoclonal antibody by rational design", Biochemical and Biophysical Research Communications.
Vajdos et al., 2002, "Comprehensive functional maps of the antigen-binding site of an anti-ErbB2 antibody obtained with shotgun scanning mutagenesis", J Mol Biol; 320(2):415-428.
Office Action of U.S. Appl. No. 12/213,007, dated Nov. 19, 2010.
Russian Office Action of Russian application No. 2008128139, dated Nov. 8, 2010.
European Office Action of European application No. 08838455.7-2406, dated Oct. 21, 2010.
Mexican Office Action (translation) of Mexican application No. MX/a/2009/013503, dated Dec. 28, 2010.
Office Action of U.S. Appl. No. 12/138,372, dated Feb. 2, 2011.
Chen et al., 1999, "Selection and analysis of an optimized anti-VEGF antibody: crystal structure of an affinity-matured Fab in complex with antigen", J Mol Biol; 293:865-881.
Rebe et al., 2005, "Deglycosylation of anti-β amyloid antibodies inhibits microglia activation in BV-2 cellular model", American Journal of Alzheimer's Disease and Other Dimentias; 20(5):303-313.
Holm et al., 2007, "Functional mapping and single chain construction of the anti-cytokeratin 8 monoclonal antibody TS1", Mol Immunol; 44:1075-1084.
European Office Action of European application No. 08768371.0-2406, dated Feb. 8, 2011.
Indonesian Office Action of application No. W-00200801821, dated Feb. 25, 2011.
Written Opinion of Singapore application No. 201002372-9, dated Oct. 18, 2010.
Chinese Office Action of Chinese application No. 200680046466.9, dated Feb. 24, 2011.
Office Action of U.S. Appl. No. 12/311,505 dated Apr. 4, 2011.
European Office Action of EP application No. 08836966.5-2406, dated May 18, 2010.
European Office Action of EP application No. 08837467.3-2406, dated Oct. 21, 2010.
Hungarian Search Report of Singaporean application No. 200908189-4, dated Dec. 17, 2010.
New Zealand Examination Report of New Zealand application No. 585110, dated Jan. 19, 2011.
New Zealand Examination Report of New Zealand application No. 574188, dated Jun. 23, 2010.
New Zealand Examination Report of New Zealand application No. 581834, dated Oct. 29, 2010.
New Zealand Examination Report of New Zealand application No. 581835, dated Nov. 2, 2010.
Office Action of U.S. Appl. No. 11/637,213, dated Apr. 27, 2009.
Office Action of U.S. Appl. No. 11/777,777, dated May 5, 2010.
Office Action of U.S. Appl. No. 11/777,777, dated Aug. 10, 2009.
Vietnamese Office Action of Vietnamese application No. 1-2008-01736, dated Dec. 1, 2009.
Vietnamese Office Action of Vietnamese application No. 1-2008-01736, dated Jul. 22, 2009.
Vietnamese Office Action of Vietnamese application No. 1-2008-01736, dated Dec. 1, 2008.
Chilean Office Action of Chilean application No. 2007-2070 with English Technical Report, dated Mar. 14, 2011.
Chilean Office Action of Chilean application No. 3485-2006 with English Technical Report, dated Apr. 13, 2011.
Davies et al., 1996, "Affinity improvement of single antibody VH domains: residues in all three hypervariable regions affect antigen binding", Immunotechnology; 2(3):169-179.
European Office Action, dated Jul. 18, 2011 of EP application No. 06829456.0-2402.
Holt et al., 2003, "Domain antibodies: proteins for therapy", Trends in Biotechnology; 21(11):484-490.
Maynard et al., 2000, "Antibody engineering", Annu Rev Biomed Eng; 2:339-376.
Mexican Office Action (translation) of Mexican application No. MX/a/2009/000476, dated Mar. 30, 2011.
Mexican Office Action of Mexican application No. MX/a/2008/007477, dated Mar. 17, 2011.
Mexican Office Action of Mexican application No. MX/a/2009/003468, dated Aug. 8, 2011.
Office Action of U.S. Appl. No. 12/460,747, dated Jun. 8, 2011.
Office Action of U.S. Appl. No. 12/213,006, dated Apr. 19, 2011.
Office Action of U.S. Appl. No. 12/589,570, dated Jul. 20, 2011.
Pini et al., 1998, "Design and use of a phage display library. Human antibodies with subnanomolar affinity against a marker of angiogenesis eluted from a two-dimensional gel", J Biol Chem; 273(34):21769-21776.
Singapore Examination Report of Singaporean application No. 200900163-7, dated Sep. 30, 2010.
Ukrainian Office Action of Ukrainian application No. 200808792, dated Jun. 1, 2011.
Written Opinion of Singaporean application No. 200908190-2, dated Jul. 8, 2011.
U.S. Appl. No. 13/136,435, filed Jul. 29, 2011, Pfeifer et al.
Australian Examination Report dated Aug. 23, 2011 of Australian application No. 2006326284.
Brown et al., 1996, "Tolerance of single, but not multiple, amino acid replacements in antibody VH CDR 2: a means of minimizing B cell wastage from somatic hypermutation?", J Immunol; 156(9):3285-3291.
Chilean Office Action dated Aug. 16, 2011 of Chilean application No. 1741-2008, with English Technical Report, dated Oct. 31, 2011.
Chilean Office Action dated Aug. 11, 2011 of Chilean application No. 1742-2008 with English Technical Report.
Chinese Office Action (English translation) dated Oct. 14, 2011 of Chinese application No. 200780044555.4.
Bedzyk et al., 1990, "Active site structure and antigen binding properties of idiotypically cross-reactive anti-fluorescein monoclonal antibodies", J Biol Chem; 265(1):133-138.
Chinese Office Action (translation) dated Sep. 23, 2011 of Chinese Patent application No. 200780033976.7.
Chinese Office Action (with English translation), dated Jul. 27, 2011 of application No. 200780033976.7.
European Office Action, dated Dec. 13, 2011 of European application No. 07867188.0-2406.
European Office Action, dated Oct. 11, 2011 of European application No. 08768371.0-2406.
European Search Report, dated Jul. 11, 2011 of European application No. 10196705.
Summons to Attend Oral Proceedings dated Dec. 22, 2011 of European application No. 07840408.4-2406.

Frenkel et al., 1999, "High affinity binding of monoclonal antibodies to the sequential epitope EFRH of beta-amyloid peptide is essential for modulation of fibrillar aggregation"; J Neuroimmunol; 95(1-2):136-142.
Gulf Cooperation Council Office Action dated Oct. 16, 2011, of GCC application No. GCC/P/2007/8700, with Chinese Examination Report, dated Jul. 19, 2011.
Gulf Cooperation Council Office Action of GCC application No. 7389 (English translation), dated Jul. 5, 2011 with Examination Report of application GCC/P/2006/7389, dated Mar. 3, 2011.
Hungarian Written Opinion, dated Nov. 10, 2011 of Singaporean application No. 200908189-4.
Israeli Office Action dated Sep. 12, 2011, of Israeli patent application No. 196748 (Informal translation).
Malaysian Office Action, dated Nov. 30, 2011 of Malaysian application No. PI 20081950.
Mexican Office Action (translation), dated Nov. 22, 2011 of Mexican application No. MX/a/2009/013505.
Mexican Office Action (translation), dated Nov. 23, 2011 of Mexican application No. MX/a/2011/004131.
Mexican Office Action, dated Nov. 9, 2011 of Mexican application No. MX/a/2008/007477.
New Zealand Examination Report, dated Jul. 19, 2011 of New Zealand application No. 568012.
New Zealand Examination Report, dated Sep. 13, 2011 of New Zealand application No. 574188.
New Zealand Examination Report, dated Sep. 13, 2011 of New Zealand application No. 595068.
Notice of Allowance and Fees Due, dated Oct. 19, 2011 of U.S. Appl. No. 12/311,505.
Office Action, dated Aug. 12, 2011 of U.S. Appl. No. 12/138,372.
Office Action, dated Nov. 1, 2011 of U.S. Appl. No. 12/460,747.
Office Action, dated Nov. 2, 2011 of U.S. Appl. No. 12/589,570.
Ohno et al., 1985, "Antigen binding specificities of antibodies are primarily determined by seven residues of VH", Proc Natl Acad Sci USA; 82(9):2945-2949.
Ozawa et al., 2002, "Enhanced $A\beta_{40}$ deposition was associated with increased $A\beta_{42/43}$ in cerebral vasculature with dutch-type hereditary cerebral hemorrhage with amyloidosis (HCHWA-D)", Ann NY Acad Sci; 977:149-154.
Pakula et al., 1989, "Genetic analysis of protein stability and function", Annu Rev Genet; 23:289-310.
Philippines Office Action, dated Sep. 14, 2011 of Philippines application No. 12008501065.
Russian Office Action (translation), dated Jul. 6, 2011 of Russian application No. 2008128139/10.
Russian Office Action (translation), dated Nov. 30, 2011 of Russian application No. 2008128139.
Russian Office Action of Russian application No. 200900880, dated Oct. 3, 2011 (with English translation).
Russian Office Action, dated Sep. 9, 2011 of Russian application No. 2009104769/10.
Ukrainian Office Action, dated Dec. 1, 2011 of application No. 200808792.
Vietnamese Office Action, dated Feb. 9, 2012 of Vietnamese application No. 1-2008-01736.
Casset et al., 2003, "A peptide mimetic of an anti-CD4 monoclonal antibody by rational design", Biochemical and Biophysical Research Communications; 307:198-205.
Glaucoma—Wikipedia entry, downloaded Jan. 30, 2012.
Office Action, dated Feb. 2, 2012 of U.S. Appl. No. 12/681,673.
Office Action, dated Feb. 2, 2012 of U.S. Appl. No. 12/681,683.
Chilean Office Action, dated Mar. 9, 2012 of Chilean application No. 2070-2007.
Chinese Office Action, dated Feb. 9, 2012 of Chinese application No. 200880103155.0.
De Pascalis et al., 2002, "Grafting of "Abbreviated" complementarity-determining regions contains specificity-determining residues essential for ligand contact to engineer a less immunogenic humanized monoclonal antibody", J Immunol; 169:3076-3084.
Egyptian Office Action, as sent in an email dated Mar. 24, 2012 of Egyptian application No. PCT/794/2008.
Hensley et al., 1999, "p38 kinase is activated in the Alzheimer's disease brain", J Neurochem; 72:2053-2058.
International Search Report, dated Apr. 3, 2012 of International application No. PCT/US11/45948.
Israeli Office Action dated Feb. 27, 2012, of Israeli patent application No. 204837 (Unofficial translation).
Israeli Office Action, dated Jan. 4, 2012 of Israeli application No. 191230 (Unofficial translation).
Li et al., 2003, "Interleukin-1 mediates pathological effects of microglia on tau phosphorylation and on synaptophysin synthesis in cortical neurons through a p38-MAPK pathway", J Neuroscience; 23(5):1605-1611.
Munoz et al., 2007, "A novel p38α MAPK inhibitor suppresses brain proinflammatory cytokine up-regulation and attenuates synaptic dysfunction and behavioral deficits in an Alzheimer's disease mouse model", J Neuroinflammation; 4(21):1-14.
Munoz et al., 2010, "Targeting p38 MAPK pathway for the treatment of Alzheimer's disease", Neuropharmacology; 5(3):561-568.
New Zealand Examination Report of New Zealand application No. 574188, dated Mar. 9, 2012.
Office Action dated Mar. 27, 2012 of U.S. Appl. No. 12/701,199.
Singapore Examination Report, dated Feb. 10, 2012 of Singapore application No. 200908190-2.
Ukrainian Office Action dated Oct. 3, 2011 of Russian application No. 200900880 (with English translation).
Written Opinion, dated Apr. 3, 2012 of International application No. PCT/US11/45948.
Wu et al., 1999, "Humanization of a murine monoclonal antibody by simultaneous optimization of framework and CDR residues", J Mol Biol; 294:151-162.
Israeli Office Action, dated Feb. 22, 2012 of Israeli patent application No. 204836.

* cited by examiner

FIG. 1-1

FIG. 2-1

```
                    10                  20                30
C2VHAF     E V Q L V E S G G G L V Q P G G S L K L S C A A S G F T F S
AF120466   E V K L V E S G G G L V K P G G S L K L S C A A S G F T F S 40                  50                60
C2VHAF     S Y G M S W V R Q T P D K R L E L V A S I N S N G G S T Y Y
AF120466   S Y G M S W V R Q T P D K R L E W V A T I S S G G S Y T Y Y 70                  80                90
C2VHAF     P D S V K G R F T I S R D N A K N T L Y L Q M S S L K S E D
AF120466   P D S V K G R F T I S R D N A K N T L Y L Q M S S L K S E D 100             110
C2VHAF     T A M Y Y C A S G D Y W G Q G S T L T V S S
AF120466   T A M Y Y C A R R
```

FIG. 3

|         | 1                                                           | 10                    | 20                    | 30        |
|---------|-------------------------------------------------------------|-----------------------|-----------------------|-----------|
| C2VK    | D V V M T Q T P L S L P V S L G D Q A S I S C R S S Q S L V |
| C2HuVK1 | D I V M T Q S P L S L P V T P G E P A S I S C R S S Q S L V |
| C2HuVK2 | D I V M T Q S P L S L P V T P G E P A S I S C R S S Q S L V |
| C2HuVK3 | D I V M T Q S P L S L P V T P G E P A S I S C R S S Q S L V |
| C2HuVK4 | D I V M T Q S P L S L P V T P G E P A S I S C R S S Q S L V |
| dpk15   | D I V M T Q S P L S L P V T P G E P A S I S C R S S Q S L L |
| JK1     | - - - - - - - - - - - - - - - - - - - - - - - - - - - - - - |

|         | 40                    | 50                    | 60                    |
|---------|-----------------------|-----------------------|-----------------------|
| C2VK    | Y S N G D T Y L H W Y L Q K P G Q S P K L L I Y K V S N R F |
| C2HuVK1 | Y S N G D T Y L H W Y L Q K P G Q S P Q L L I Y K V S N R F |
| C2HuVK2 | Y S N G D T Y L H W Y L Q K P G Q S P Q L L I Y K V S N R F |
| C2HuVK3 | Y S N G D T Y L H W Y L Q K P G Q S P K L L I Y K V S N R F |
| C2HuVK4 | Y S N G D T Y L H W Y L Q K P G Q S P K L L I Y K V S N R F |
| dpk15   | H S N G Y N Y L D W Y L Q K P G Q S P Q L L I Y L G S N R A |
| JK1     | - - - - - - - - - - - - - - - - - - - - - - - - - - - - - - |

|         | 70                    | 80                    | 90                    |
|---------|-----------------------|-----------------------|-----------------------|
| C2VK    | S G V P D R F S G S G S G T D F T L K I S R V E A E D L G V |
| C2HuVK1 | S G V P D R F S G S G S G T D F T L K I S R V E A E D V G V |
| C2HuVK2 | S G V P D R F S G S G S G T D F T L K I S R V E A E D V G V |
| C2HuVK3 | S G V P D R F S G S G S G T D F T L K I S R V E A E D V G V |
| C2HuVK4 | S G V P D R F S G S G S G T D F T L K I S R V E A E D V G V |
| dpk15   | S G V P D R F S G S G S G T D F T L K I S R V E A E D V G V |
| JK1     | - - - - - - - - - - - - - - - - - - - - - - - - - - - - - - |

|         | 100                   | 110                   |
|---------|-----------------------|-----------------------|
| C2VK    | Y F C S Q S T H V P W T F G G G T K L E I K |
| C2HuVK1 | Y Y C S Q S T H V P W T F G Q G T K V E I K |
| C2HuVK2 | Y F C S Q S T H V P W T F G Q G T K V E I K |
| C2HuVK3 | Y Y C S Q S T H V P W T F G Q G T K V E I K |
| C2HuVK4 | Y F C S Q S T H V P W T F G Q G T K V E I K |
| dpk15   | Y Y C M Q - - - - - - - - A - L Q T P |
| JK1     | - - - - - - - - - W T F G Q G T K V E I K |

*FIG. 10*

```
                              10                  20              30
C2VHAF    E V Q L V E S G G G L V Q P G G S L K L S C A A S G F T F S
C2HuVHAF1 E V Q L V E S G G G L V Q P G G S L R L S C A A S G F T F S
C2HuVHAF2 E V Q L V E S G G G L V Q P G G S L R L S C A A S G F T F S
C2HuVHAF3 E V Q L V E S G G G L V Q P G G S L R L S C A A S G F T F S
C2HuVHAF4 E V Q L V E S G G G L V Q P G G S L R L S C A A S G F T F S
DP-54     E V Q L V E S G G G L V Q P G G S L R L S C A A S G F T F S
HUJH6     - - - - - - - - - - - - - - - - - - - - - - - - - - - - - -

40                  50              60
C2VHAF    S Y G M S N V R Q T P D K R L E L V A S I N S N G G S T Y Y
C2HuVHAF1 S Y G M S N V R Q A P G K G L E W V A S I N S N G G S T Y Y
C2HuVHAF2 S Y G M S N V R Q A P G K G L E W V A S I N S N G G S T Y Y
C2HuVHAF3 S Y G M S N V R Q A P G K G L E L V A S I N S N G G S T Y Y
C2HuVHAF4 S Y G M S N V R Q A P G K G L E L V A S I N S N G G S T Y Y
DP-54     S Y W M S N V R Q A P G K G L E W V A N I K Q D G S E K Y Y
HUJH6     - - - - - - - - - - - - - - - - - - - - - - - - - - - Y Y 70                  80              90
C2VHAF    P D S V K G R F T I S R D N A K N T L Y L Q M S S L K S E D
C2HuVHAF1 P D S V K G R F T I S R D N A K N S L Y L Q M N S L R A E D
C2HuVHAF2 P D S V K G R F T I S R D N A K N S L Y L Q M N S L R A E D
C2HuVHAF3 P D S V K G R F T I S R D N A K N S L Y L Q M N S L R A E D
C2HuVHAF4 P D S V K G R F T I S R D N A K N S L Y L Q M N S L R A E D
DP-54     V D S V K G R F T I S R D N A K N S L Y L Q M N S L R A E D
HUJH6     - - - - - - - - - - - - - - - - - - - - - - - - - - - - - -

100                 110
C2VHAF    T A M Y Y C A S G D Y W G Q G S T L T V S S
C2HuVHAF1 T A V Y Y C A R G D Y W G Q G T T V T V S S
C2HuVHAF2 T A V Y Y C A S G D Y W G Q G T T V T V S S
C2HuVHAF3 T A V Y Y C A R G D Y W G Q G T T V T V S S
C2HuVHAF4 T A V Y Y C A S G D Y W G Q G T T V T V S S
DP-54     T A V Y Y C A R
HUJH6     - - - Y Y Y G M - D V W G Q G T T V T V S S
```

*FIG. 11*

BamHI
                                                                          BglII
GGATCCTGGCAGAGTCTTCACAGATGCTTCTGAGACAACATTTGCTTTCAAAAAATGAACCACCACACATCCTAAAGATCTCAGCCACTTCCATGTTCAT
----+----+----+----+----+----+----+----+----+----+----+----+----+----+----+----+----+----+----+----+ 100
CCTAGGACCGTCTCAGAGTGTCTACGAAGACTCTGTTGTAAACGAAAGTTTTTTACTTGGTGTGTAGGATTTCTAGAGTCGGTGAAGGTACAAAGTA

TTTATGTTACAGCAAACATCACAACAATCATTCCTACAGATCACCACTGCATGTGATCAATAAAATAGTTTTGCAACAATGTACTTATGATAATCATC
----+----+----+----+----+----+----+----+----+----+----+----+----+----+----+----+----+----+----+----+ 200
AAATACAATGTCGTTTGTAGTGTTAGTAAGGATGTCTAGTGGTGACGTACACTAGTTATTTTATCAAAAACGTTGTTACCATGAATACTATTAGTAG

TTTTATTGTTACAAATACTGCTTTACAATAGTTATTCGGTTGCACTGTTCATATATTAGAGTTCCAATTAGCTCACTTAGGAACATAAGTCCCTGAACAG
----+----+----+----+----+----+----+----+----+----+----+----+----+----+----+----+----+----+----+----+ 300
AAAATAACAAATGTTTATGACGAAATGTTATCAATAAGCCAACGTGACAAGTATAATCTAAAGGTTAATCGAGTGAATCCTTGTATTCAGGGAGCTTGTC

CTCAGTGTCATCTTTTTCATTCCTGTTTCTATCCCCTACATCTCTTCCTTTGCAGACGACTATCTCCTACACTGAAACAGGAAAGCTAGCTTTTTTTTC
----+----+----+----+----+----+----+----+----+----+----+----+----+----+----+----+----+----+----+----+ 400
GAGTCAGTAGAAAAAGTAAGGACAAAGATAGGGGATGTAGAGAAGGAAACGTCTGCTGATAGAGGATGTGACTTTGTCCTTTCGATCGAAAAAAAAAG

AGTGCTATTTAATTATTTCAATATCCTCATCAAATGTATTTAAATACAACAAAGCTCAACCAAAAAGAAATATGTAATTCTTTCAGAGTAAAAAT
----+----+----+----+----+----+----+----+----+----+----+----+----+----+----+----+----+----+----+----+ 500
TCACGATAAATTAATAAAGTTATAGGAGTAGTTTACATAAATTTATTGTTTCGAGTTGGTTTTCTTTTTCTTATACATTAAGAAAGTCTCATTTTA

CACACCCATGACCTGGCCACTGAGGGCTTGATCAATTCACTTTGAATTGGCATTAAATACCATTAAGGTATATTAACTGATTTAAAATAAGATATATT
----+----+----+----+----+----+----+----+----+----+----+----+----+----+----+----+----+----+----+----+ 600
GTGTGGGTACTCGACCGGTGACTCCCGAACTAGTTAAGTAACTTAAACCGTAATTATGGTAATTCCATATATTGGACTAAAATTTATTCTATATAA

CGTGACCATGTTTTAACTTTCAAAAATGTAGCTGCCAGTGTGATTTATTCAGTTGTACAAAATATCTAAACCTATGCAATGTGATTAATAAAAA
----+----+----+----+----+----+----+----+----+----+----+----+----+----+----+----+----+----+----+----+ 700
GCACTGGTACAAAATTGAAAGTTTTTACATCGACGGTCACACTAAAATAAGTCAACATGTTTATAGATTGGATATCGTTACACTAATTATTTT

FIG. 13 - 1

CTTAAACATATTTCCAGTACCTTAATTCTGTGATAGGAAAATTTAATTCATAATCTGAGTATTTAATTCATAATCTCTAAAATAGTTTAATGATTGTCATG
----+----|----+----|----+----|----+----|----+----|----+----|----+----|----+----|----+----|----+----| 800
GAATTTGTATAAAGGTCATGGAATTAAGACACTATCCTTTTAAATTAAGACTCATAAATTAAGTATTAGAGATTTTATCAAATTACTAAACAGTAAC
                              PvuII

TGTTGCTGTGCGTTACCCCAGCTGATCTCAAAAGTGATATTTGGTCTGCAACAACTGATAGAGGACTATTTTAGGGCCTTTTAAAG
----+----|----+----|----+----|----+----|----+----|----+----|----+----|----+----|----+----| 900
ACAACGACAGCAAATGGGGTCGACTAGAGTTTTCACTATAAACCAGACGTTGTTGACTATCCTGATAAAATCCCGGAAAATTTC

CTCTATTAAAACTAACTACAACGATTCAAAACTGTTTAAACTATTTCAAAATGATTTTAGAGCCTTTTGAAACTCTTTTAAACTCT
----+----|----+----|----+----|----+----|----+----|----+----|----+----|----+----|----+----| 1000
GAGATAATTTTGATTGAATGTTGCTAAGTTTTGACAAATTTGATAAAGTTTACTAAAATCTCGGAAAACTTTGAGAAAATTGAGA
                                                                                  EcoRI

ATTAAAACTAATAAGATAACTTGAAATAATTTCATGTCAAATACATTAACTGTTTAATGTTAAATGCCAGATGAAAAATGTAAGCTATCAAGAATTC
----+----|----+----|----+----|----+----|----+----|----+----|----+----|----+----|----+----|----+----| 1100
TAATTTGATTATTCTATTGAACTTTATTAAAGTACAGTTTATGTAATTGACAAATTACGTTCTACTTTTTACATTCGGTCTACTTTCGATAGTTCTTAAG
                                                                NcoI

ACCCAGATAGGAGTATCTTCATAGCTACTGTTTTCCCTGCTTATTTCCAGTGATCACATTATTTGCTACCATGGTTATTTATACAATTATCTGAAAAA
----+----|----+----|----+----|----+----|----+----|----+----|----+----|----+----|----+----|----+----| 1200
TGGGTCTATCCTCATAGAAGTATCGATGACAAAAGGGACGAATAAAGGTCACTAGTGTAATAAAACGATGGTACCAATAAATATGTTAATAGACTTTTT

AATTAGTTATGAAGATTAAAAGAGAAGAAAATATTAAACATAAGAGATCTTCATGTTGAACTGCTGGTTAACAGTGAAGTTAGTTTTAAAAAA
----+----|----+----|----+----|----+----|----+----|----+----|----+----|----+----|----+----|----+----| 1300
TTAATCAATACTTCTAATTTCTCTTCTTTTATAATTTGTATTCTCTAAGTCAGAAGTACAACTTGACGACCAATTGTCACTTCAATCAAAATTTTT
                                                                                PvuII

AAAAAAAAACTATTTCTGTTATCAGCTGACTTCTCCCTATCTGTTGACTTCTCCCAGCAAAAGATTCTTATTTTACATTTTAACTACTGCTCTCCCACCCA
----+----|----+----|----+----|----+----|----+----|----+----|----+----|----+----|----+----|----+----| 1400
TTTTTTTTTGATAAAGACAATAGTCGACTGAAGAGGGATAGACAACTGAAGAGGGTCGTTTTCTAAGAATAAAATGTAAAATTGATGACGAGAGGGTGGGT

FIG. 13-2

FIG. 13-5

```
CCCTCCCATCCTTGGCCTCTGACCCTTTTTCCACAGGGGACCTACCCCTATTGGGGTCCTCCAGTCATCTTTCACCTCACCCCCTCCTCCTCCTTGG      260
---+----|----+----|----+----|----+----|----+----|----+----|----+----|----+----|----+----|----+----|
GGGAGGGTAGGAACCGGAGACTGGGAAAAAGGTGTCCCCTGGATGGGGATAACGCCAGGAGGTCGAGTAGAAAAGTGGAGTGGGGAGGAGGAGGAACC

CTTTAATTATGCTAATGTTGGAGGAGAATGAATAAAAGTGAATCTTTGCACCTGTGGTTTCTCCTCTTCCTCATTTAATAATTATTATCTGTTGTTT      270
---+----|----+----|----+----|----+----|----+----|----+----|----+----|----+----|----+----|----+----|
GAAATTAATACGATTACAACCTCCTCCTTACTTATTTATTTCACTTAGAAACGTGGACACCAAAGAGAGAAAGGAGTAAATTATTAATAGACAACAAA

TACCAACTACTCAATTTCTCTTATAAGGACTAAAATGTAGTCATCCTAAGGCGCATAACCATTTATAAAAATCATCCTTCATTCTATTTTACCCTATC      280
---+----|----+----|----+----|----+----|----+----|----+----|----+----|----+----|----+----|----+----|
ATGGTTGATGAGTTAAAGAGAATATTCCCTGATTATACATCAGTAGGATTCCCGCGTATTGGTAAATATTTTAGTAGGAAGTAAGATAAATGGATAG
                                                    NcoI
                                                    |‾‾|
ATCCTCTGCAATACAGTCCTCCCCTCAAACCCCACAAGCCTTCTGTCCTCACAGTCCCTGGGCCATGGTAGGAGACTTGCTTCCTTGTTTTCCCCTCCT     290
---+----|----+----|----+----|----+----|----+----|----+----|----+----|----+----|----+----|----+----|
TAGGAGACGTTATGTCAGGAGGAGTTTGGGTGTTCGGAAGACAGAGTGTCAGGGGACCCGGTACCATCCTCTCTGAACGAAGGAACAAAGGGAGGA

CAGCAAGCCCTCATAGTCCTTTTTAAGGGTGACAGGTCTTACAGTCATATATCCTTTGATTCAATTCCCTGAGAATCAACCAAAGCAAATTTTTCAAAAG    300
---+----|----+----|----+----|----+----|----+----|----+----|----+----|----+----|----+----|----+----|
GTCGTTCGGAGTATCAGGAAAAATTCCCACTGTCCAGATGTCAGTATATAGGAAACTAAGTTAAGGGACTCTTAGTGTTGGTTTCGTTAAAAGTTTTC

AAGAAACCTGCTATAAAGAGAATCATTCATTGCAACATGATATAAAATAACACACATGATATAAAATAACAAACAATTAAAATAAACAATAGGAAATGTTAAGT   310
---+----|----+----|----+----|----+----|----+----|----+----|----+----|----+----|----+----|----+----|
TTCTTTGGACGATATTTCTTAGTAAGAGTTGTACTATATTTTATTGTGTTGTTATTTCGTTAATTATTTGTTGTTGTTAATCCCTTTACAAATTCA

TCATCATGGTACTTAGACTTAATGGAATGTCATGCCCTTATTTACATTTTTAAACAGTACTGAGGACTCCTGTCTGCCAAGGGCCGTATTGAGTACTTT   320
---+----|----+----|----+----|----+----|----+----|----+----|----+----|----+----|----+----|----+----|
AGTAGTACCATGAATCTGAATTACCTTACAGTACGAATAAATGTAAAAATTTGTCATGACTCCCTGAGGACAGAGCGGTTCCCGGCATAACTCATGAAA

CCACAACCTAATTTAATCCACACTATACTGTGAGATTAAAAACATTCATTAAAAATGTTGCAAAGGTTCTATAAAGCTGAGAGACAAATATATTCTATAAC   330
---+----|----+----|----+----|----+----|----+----|----+----|----+----|----+----|----+----|----+----|
GGTGTTGGATTAAATTAGGTGTGATATGACACTCTAATTTTTGTAAGTAATTTACAACGTTTCCAAGATATATTCGACTCTCTGTTTATATAAGATATTG
```

FIG. 13-6

```
                                                                                                                                    340
TCAGCAATCCCACTTCTAGATGACTCAGTGTCCCCACCCACCAAAAAACTATGCAAGAATGTTCAAGCAGCTTTATTTACAAAAGCCAAAAATTGGAAA
----+----|----+----|----+----|----+----|----+----|----+----|----+----|----+----|----+----|----+----|
AGTCGTTAGGGTGAAGATCTACTGACTCACAGGGGTGGGTGGTTTTGATACGTTCTTACAAGTTCGTCGAAATAAATGTTTTCGGTTTTTAACCTTT
 Xbal
                                                                                                                                    350
TAGCCCGATTGTCCAACAATGAATGAGTTATTAAACTGTGGTATGTTTATACATTAGAATACCCAATGAGGAGAATTAACAAGCTACAACTATACCTAC
----+----|----+----|----+----|----+----|----+----|----+----|----+----|----+----|----+----|----+----|
ATCGGGCTAACAGGTTGTTACTTACTCAATAATTTGACACCATAAATCTTATGGGTTACTCCTCTTAATGTTCGATGTTGATATGGATG 360
TCACACAGATGAATCTCATAAAAATAATGTTACATAAGAGAAACTCAATGCAAAAGATATGTTCTGTATGTTTCATCCATATAAAGTTCAAAACCAGGT
----+----|----+----|----+----|----+----|----+----|----+----|----+----|----+----|----+----|----+----|
AGTGTCTACTTAGAGTATTTTTATTACAATGTATCTCTTTGAGTTACGTTTCTACAAGACATACAAAAGTAGGTATATTTCAAGTTTTGGTCCA 370
AAAAATAAAGTTAGAAATTTGGATGGAAATTACTCTTAGCTCCTGGGGGTGGGCGAGTTAGTGCCTGGGAGAGAAGAACAAGAAGGGGCTTCTGGGGTCTCTTGGTAA
----+----|----+----|----+----|----+----|----+----|----+----|----+----|----+----|----+----|----+----|
TTTTTATTTCAATCTTTAAACCTACCTTTAATGAGAATCGACCCCACCCGCTCAATCGGACCCCTCTTCTTGTTCTTCCCGAAGACCCCAGAACCATT
                                                 Bsgl
                                                                                                                                    380
TGTTCTCGTTCCTCGTGTGGGGTTGTGCAGTTATGATCTGTGCACTGTTCTGTATACACATTATGCTTCAAAATAACTTCACATAAAGAACATCTTATACC
----+----|----+----|----+----|----+----|----+----|----+----|----+----|----+----|----+----|----+----|
ACAAGACAAGGAGCACACCCCAACGTCAATACTAGACACGTGACAAGACATATGTAATACGAAGTTTTATTGAAGTGTATTCTTGTAGAATATGG
                                                                                   Pvull
                                                                                                                                    390
CAGTTAATAGAATAGAAGAGGAATAAGTAATAGGTCAAGACCATGCAGCTGGTAAGTGGGGGCCTGGATCAAATAGCTACCTGCCTAATCCTGCCCTC
----+----|----+----|----+----|----+----|----+----|----+----|----+----|----+----|----+----|----+----|
GTCAATTATCTATCTTCTCCTTATTCATTATCCAGTTCTGGTACGTCGACCATTCACCCCCCCGGACCCCTAGTTTATCGATGGACGGATTAGGACGGGAG
```

FIG. 13-7

FIG. 13-8

```
TGGAAATAGGGTCTCTTTGCAGAGGTAATCAAGTCATACTGAAAATTAGGTCATATACTGAAATGTTTGTGAGGATGCGGTGAAAATGGATCATTCATATATTGCTGGTG
-----+---------+---------+---------+---------+---------+---------+---------+---------+---------+---------+  480
ACCTTTATCCCAGAAACGTCTCCATTAGTTCAGTTTAATCCAGTTTTAACAAACTCCTACGCCACTTTACCCACTTTACCTAGTAAGTATATAACGACCAC

Xbal
GGAATATAAAGGGTATAGCTACTCTAGAAAATAGTTGTCAGTTCCTGAAAACTAAACAAAGACACCTACCATATGACCCAGGAATTGTACTCCTTG
-----+---------+---------+---------+---------+---------+---------+---------+---------+---------+  490
CCTTATATTTCCCATATCGATGAGATCTTTTATCAACAGTCAAAGACTTTTGATTTGTTTCTGTGGATGGTATACTGGGTCCTTAACATGAGGAAC GGAATTACCCCCAGGAAATAAAAACTTATGTCCACACAGAACCCATAGATGATTGTTCACAGCAGCTTTATTGTGTAGCCAAAGCTAGAAAGAGCCA
-----+---------+---------+---------+---------+---------+---------+---------+---------+---------+  500
CCTTAATGGGGGTCCTTTATTTTTGAATACAGGTGTCGTCGGGTATGTACTAACAAGTGTCGTCGAAATAAACAACATCGGTTTCGATCTTTCTCGGT ACCCATCCCTCAATAGGCAACTAGCCTAACAAATTGTAATATATCCATGCCATAGAATGCTATGAGGCAATAAAAAGGAACGAAGTGTTCATACAGAGAA
-----+---------+---------+---------+---------+---------+---------+---------+---------+---------+  510
TGGGTAGGGAGTTATCCGTTGATCGATTGTTTAACATTATATAGGTACGGTATCTTACGATACTCCGTTATTTTCCTTGCTCACAAGTATGCTCTT CTGGAGTGATTCTGAAGACTTCTACTGAGTGAAAAAAGCCAATCTGAAGGGTCACATACCATGTGATTCCTTTATGTAACATTGTTGAAGTGACAA
-----+---------+---------+---------+---------+---------+---------+---------+---------+---------+  520
GACCTCACTAAGACTTCCTGAAAGATGACTCACTTTTTTCGGTAGACTTCCCAGTGTATGGTACACTAAGGAAAATACATTGTAACAACTTCACTGTT
```

FIG. 13-9

```
                Xmnl                                                                                    Bglll
AATTATAGGGATAGAGAACAGATTCTGGTTGCCAGGGGTTAGGGTGGTGGAGAAAGAAGAGTAGGCGAAACTATAAAGGGAGATCTTTGTGATCATGGGA    530
---+---+---+---+---+---+---+---+---+---+---+---+---+---+---+---+---+---+---+---+---+---+---+---+---+
TTAATATCCCTATCTCTTGTCTAAGACCAACGGTCCCCAATCCCACCACCTCTTTCTTCTCATCGCTTTGATATTCCCTCTAGAAACACTAGTACCCT Xbal
TAAATCTGTATCTTGATTGCAGTGGTAGTTGCAGGCATCTAGACATGTGATAAAATGACATAGAACTGTACACACTTATTTTATCAATGTCAAATTCTTG   540
---+---+---+---+---+---+---+---+---+---+---+---+---+---+---+---+---+---+---+---+---+---+---+---+---+
ATTTAGACATAGAACTAACGTCACCATCAACGTCCGTAGATCTGTACACTATTTTACTGTATCTTGACATGTGTGAATAAAATAGTTACAGTTTAAGAAC Bsgl
GTTTTAATATCGTACTGTAATTACGTAAGAAGTAACCAACAGGAGAAACTGGGTGCAGGACACATCAGACCTCTGTGCTTTATATCCTGTCTTTGCTACT   550
---+---+---+---+---+---+---+---+---+---+---+---+---+---+---+---+---+---+---+---+---+---+---+---+---+
CAAAATTATAGCATGACATTCTTCATTGGTTGCTCCTCTTTGACCCAGTCCTGTGTAGTCTGGAGACACGAAATATAGGACAGAAACGATGA TTCTGTGAATCTATAATTATTCCAAATAATTTTTTAAACTTTTTTTTTATGCTGGATCG   5561
---+---+---+---+---+---+---+---+---+---+---+---+
AAGACACTTAGATATTAATAAGGTTTATTAAAAAATTTGAAAAAAAAATACGACCTAGC
```

```
                                                                                          110
TGCCCTAGAGTAGCCTGCATCCAGGGACAGGCCCCAGCGGGTGCTGACGTGCTTCCTCAGCACCTGAGTTCCTGGGGGACCATCA
---+---------+---------+---------+---------+---------+---------+---------+---------+
ACGGGATCTCATCGGACGTAGGTCCCTGTCCGGGGTCGCCCACGACTGCACGAAGGAGTCGTGGACTCAAGGACCCCCTGGTAGT
                                                      A  P  E  F  L  G  G  P  S
                                                                    CH2
                                                                                          120
GTCTTCCTGTTCCCCCCAAAACCCCAAGGACACTCTCATGATCTCCCGGACCCCTGAGGTCACGTGCGTGGTGGTGGACGTGAGC
---+---------+---------+---------+---------+---------+---------+---------+---------+
CAGAAGGACAAGGGGGGTTTTGGGGTTCCTGTGAGAGTACTAGAGGGCCTGGGGACTCCAGTGCACGCACCACCACCTGCACTCG
V  F  L  P  P  P  K  P  K  D  T  L  M  I  S  R  T  P  E  V  T  C  V  V  V  D  V  S
                                                           CH2
                                                                                          130
CAGGAAGACCCCGAGGTCCAGTTCAACTGGTACGTGGATGGCGTGGAGGTGCATAATGCCAAGACAAAGCCGCGGGAGGAGCAG
---+---------+---------+---------+---------+---------+---------+---------+---------+
GTCCTTCTGGGGCTCCAGGTCAAGTTGACCATGCACCTACCGCACCTCCACGTATTACGGTTCTGTTTCGGCGCCCTCCTCGTC
Q  E  D  P  E  V  Q  F  N  W  Y  V  D  G  V  E  V  H  N  A  K  T  K  P  R  E  E  Q
                                              CH2
                                                                                          140
TTCAACAGCACGTACCGTGTGGTCAGCGTCCTCACCGTCCTGCACCAGGACTGGCTGAACGGCAAGGAGTACAAGTGCAAGGTC
---+---------+---------+---------+---------+---------+---------+---------+---------+
AAGTTGTCGTGCATGGCACACCAGTCGCAGGAGTGGCAGGACGTGGTCCTGACCGACTTGCCGTTCCTCATGTTCACGTTCCAG
F  N  S  T  Y  R  V  V  S  V  L  T  V  L  H  Q  D  W  L  N  G  K  E  Y  K  C  K  V
                           CH2
                                                                                          150
TCCAACAAAGCCCTCCCGTCTCCCATCGAGAAAACCATCTCCAAAGCCAAAGGTGGGACCCACGGGGTGCGAGGGCCACAGTGTGTACC
---+---------+---------+---------+---------+---------+---------+---------+---------+
AGGTTGTTTCGGGAGGGCAGAGGGTAGCTCTTTTGGTAGAGGTTTCGGTTTCCACCCTGGGTGCCCCACGCTCCCGGTGTCACATGG
S  N  K  G  L  P  S  S  I  E  K  T  I  S  K  A  K
                     CH2                         CH┘
                                                                                          160
AAAGGTGGGACCCACGGGGTGCGAGGGCCACATGTGTCCACATGCCCACCGTGCCCAGGTAAGCCAGCCCAGGCCTCGCCCTCCAGCTCAAGGCGGGACAGGTGCCCTAGAGTAGCCTGCATCCAGGGACAGGCCCCAGCTGGGTGCTGACA
---+---------+---------+---------+---------+---------+---------+---------+---------+
TTTCCACCCTGGGTGCCCCACGCTCCCGGTGTACACAGGTGTACGGGTGGCACGGGTCCATTCGGTCGGGTCCGGAGCGGGAGGTCGAGTTCCGCCCTGTCCACGGGATCTCATCGGACGTAGGTCCCTGTCCGGGGTCGACCCACGACTGT
         K
         CH┘
GGGCAGCCCCGAGAGCCACAGGTGTACACCCTGCCCCCATCCCGGGAGGAGATGACCAAGAACCAGGTCAGCCTGACCTGCCTGGTCAAAGGCTTCTACC
---+---------+---------+---------+---------+---------+---------+---------+---------+
CCCGTCGGGGCTCTCGGTGTCCACATGTGGGACGGGGGTAGGGCCCTCCTCTACTGGTTCTTGGTCCAGTCGGACTGGACGGACCAGTTTCCGAAGATGG
G  Q  P  R  E  P  Q  V  Y  T  L  P  P  S  Q  E  E  M  T  K  N  Q  V  S  L  T  C  L  V  K  G  F  Y
                                          CH3

FIG. 14-3
```

METHODS OF TREATING AMYLOIDOSIS WITH HUMANIZED ANTI-BETA-AMYLOID ANTIBODIES

The present application is a continuation application of U.S. application Ser. No. 11/777,777, pending, filed on Jul. 13, 2007, now U.S. Pat. No. 7,892,544, which claims benefit of priority under 35 U.S.C. §119 to U.S. Provisional Application 60/943,499 filed Jun. 12, 2007 and to EP 06014730.3 filed Jul. 14, 2006, and to EP 06020765.1 filed Oct. 1, 2006.

The present invention is related to methods and compositions for diagnosis and treatment of amyloidosis, a group of disorders and abnormalities associated with amyloid protein such as Alzheimer's disease.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., 1994).

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes β and γ secretase leads to the release of a 39 to 43 amino acid Aβ peptide. The degradation of APPs likely increases their propensity to aggregate in plaques. It is especially the Aβ(1-42) fragment that has a high propensity of building aggregates due to two very hydrophobic amino acid residues at its C-terminus. The Aβ(1-42) fragment is therefore believed to be mainly involved and responsible for the initiation of neuritic plaque formation in AD and to have, therefore, a high pathological potential. There is therefore a need for agents to prevent the formation of amyloid plaques and to diffuse existing plaques in AD.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Mid-stage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Medications are also available to address the psychiatric manifestations of AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. Many of the drugs used in AD medication such as, for example, ChEIs also have side effects that include gastrointestinal dysfunction, liver toxicity and weight loss.

Another disease that is based on or associated with the accumulation and deposit of amyloid-like protein is macular degeneration.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Ongoing research continues with studies exploring environmental, genetic, and dietary factors that may contribute to AMD. New treatment strategies are also being explored, including retinal cell transplants, drugs that will prevent or slow down the progress of the disease, radiation therapy, gene therapies, a computer chip implanted in the retina that may help stimulate vision and agents that will prevent the growth of new blood vessels under the macula.

An important factor to consider when developing new drugs is the ease of use for the target patients. Oral drug delivery,—specifically tablets, capsules and softgels—, account for 70% of all dosage forms consumed because of patient convenience. Drug developers agree that patients prefer oral delivery rather than subjecting themselves to injections or other, more invasive forms of medicinal administration. Formulations resulting in low dosing intervals (i.e. once a day or sustained release) are also preferable. The ease of administering antibiotics in oral dosage forms results in an increase of patient compliance during treatment.

What is needed are effective methods and compositions for preventing or addressing the complications associated with amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration. In particular what is needed are agents capable of counteracting the physiological manifestations of the disease such as the formation of plaques associated with aggregation of fibers of the amyloid or amyloid-like peptide.

Anti-amyloid antibodies elicited by the inoculation of $A\beta_{1-42}$ mixed with Freund complete or incomplete adjuvant were reported to reduce the amyloid burden in transgenic mice for human Alzheimer disease (Schenk et al., 1999). Intraperitoneal inoculation of tetrapalmitoylated $A\beta_{1-16}$ reconstituted in liposomes to NORBA transgenic mice elicited significant titers of anti-amyloid antibodies, which were reported to solubilize amyloid fibers and plaques in vitro and in vivo. (Nicolau et al., 2002).

A possible mechanism by which the dissolution of amyloid plaques and fibres occurred was first suggested by Bard et al., (2000), who concluded that the antibodies opsonized the plaques, which were subsequently destroyed by the macrophages of the microglia. De Mattos et al., (2001) indicated that a mAb directed against the central domain of β-amyloid was able to bind and completely sequester plasma amyloid. They argued that the presence of these mAbs in circulation shifted the equilibrium of Aβ between brain and plasma, favoring the peripheral clearing and catabolism instead of deposition within the brain.

Prolonged human therapy with rodent antibodies may result in an antiglobulin response which is detectable at about 8-12 days after administration and reaches a peak at about 20-30 days. If such an antiglobulin response is encountered, the treatment must be discontinued after not more than about 10 days and re-treatment at a latter date is usually precluded because it will lead to rapid onset of a secondary antiglobulin response. Although rodent antibodies share a considerable degree of sequence conservation with that of human antibodies, there are many sequence differences between rodents and human antibodies sufficient for the rodent antibodies to be immunogenic in humans.

This problem may be overcome by generating antibodies directly in humans or by the creation of "humanized' (a.k.a. "reshaped' antibodies). Humanized antibodies have a variable region amino acid sequence that contains the rodent-derived CDRs interspersed into human or human-like framework sequences. Since the specificity of the humanized antibody is provided by the rodent-derived CDRs, their residues are to be used essentially unchanged with only minor modifications being allowable, which do not significantly interfere with the affinity and specificity of the antibody for its target antigen. Framework residues may be derived from any primate or, particularly, from any human variable region or may be a combination thereof and the resultant designed variable region would be considered reshaped.

To maximise the likelihood that affinity will be retained in the reshaped antibody it is important to make a proper selection of the framework region. It is known that the framework sequences serve to hold the CDRs in their correct spatial orientation for interaction with antigen, and that framework residues can sometimes even participate in antigen binding. In order to maintain the affinity of the antibody for its antigen it is advantageous to select human framework sequences that are most similar to the sequences of the rodent frameworks. It then may still be necessary to replace one or more amino acids in the human framework sequence with the corresponding residue in the rodent framework to avoid losses with the affinity. This replacement may be aided by computer modelling.

The present invention provides novel methods and compositions comprising highly specific and highly effective antibodies, particularly chimeric antibodies including fragments thereof, more particularly partially or fully humanized antibodies including fragments thereof, having the ability to specifically recognize and bind to specific epitopes from a range of β-amyloid antigens, which my be presented to the antibody in a monomeric, dimeric, trimeric, etc, a polymeric form, in form of an aggregate, fibers, filaments or in the condensed form of a plaque. The antibodies enabled by the teaching of the present invention are particularly useful for the treatment of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), Adult Onset Diabetes; senile cardiac amyloidosis; endocrine tumors, and others, including macular degeneration, to name just a few.

SUMMARY OF THE INVENTION

In one embodiment, the invention relates to a chimeric antibody or a fragment thereof, or a humanized antibody or a fragment thereof, which recognizes and binds to at least one distinct binding site, particularly to a least two distinct binding sites, and more particularly to at least three distinct binding sites on the β-amyloid protein wherein said one, said at least two and said at least three binding sites each comprise at least one or two consecutive amino acid residues predominantly involved in the binding of the antibody.

In particular, the chimeric antibody or a fragment thereof, or the humanized antibody or a fragment thereof according to the invention binds to at least two, particularly to at least three distinct binding sites on the β-amyloid protein wherein at least two of the three distinct binding sites comprise at least two consecutive amino acid residues predominantly involved in the binding of the antibody and at least one of the three distinct binding sites comprise at least one amino acid residue.

The at least two distinct binding sites comprising at least two consecutive amino acid residues predominantly involved in the binding of the antibody are located in close proximity to each other on the antigen, separated and/or flanked by at least one amino acid residue not involved in antibody binding or to a significantly smaller extent as compared to said at least two consecutive amino acid residues, thus forming a conformational discontinuous epitope.

The at least three distinct binding sites comprising at least two consecutive amino acid residues and at least one amino acid residue, respectively, which are predominantly involved in the binding of the antibody are located in close proximity to each other on the epitope, separated and/or flanked by at least one amino acid residue not involved in antibody binding or to a significantly smaller extent as compared to the amino acid residues, which are predominantly involved in the binding of the antibody, thus forming a conformational discontinuous epitope.

In particular, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said at least one or said at least two distinct binding sites each comprise at least two consecutive amino acid residues predominantly involved in the binding of the antibody, wherein the at least two consecutive amino acid residues representing a first binding site are -Phe-Phe- embedded within the following core sequence (SEQ ID NO: 9):

$$Xaa_3\text{-}Phe\text{-}Phe\text{-}Xaa_4\text{-}Xaa_5\text{-}Xaa_6,$$

wherein
$Xaa_3$ is an amino acid residue selected from the group consisting of Ala, Val, Leu, norleucine, Met, Phe, and Ile;
$Xaa_4$ is an amino acid residue selected from the group consisting of Ala, Val, Leu, Ser and Ile;

Xaa₅ is an amino acid residue selected from the group consisting of Glu and Asp, Xaa₆ is an amino acid residue selected from the group consisting of Glu and Asp, and wherein said amino acid residues Xaa₃ Xaa₄, Xaa₅ and Xaa₆ are not involved in antibody binding or to a significantly smaller extent as compared to the -Phe-Phe- binding site.

In another embodiment of the invention, a chimeric antibody or a fragment thereof, or a humanized antibody or a fragment thereof is provided, wherein Xaa₃ is Val or Leu, but particularly Val;
Xaa₄ is Ala or Val, but particularly Ala;
Xaa₅ is Glu or Asp, but particularly Glu;
Xaa₆ is Glu or Asp, but particularly Asp.

In particular, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least two consecutive amino acid residues representing a first binding site are -Phe-Phe- and the at least one amino acid residue is -His- embedded within the following core sequence:

-Xaa₁-His-Xaa₃-Xaa₄-Xaa₅-Xaa₆-Phe-Phe-Xaa₇-Xaa₈-Xaa₉-, wherein

Xaa₁ is an amino acid residue selected from the group consisting of His, Asn, Gln, Lys and Arg Xaa₃ is an amino acid residue selected from the group consisting of Asn and Gln Xaa₄ is an amino acid residue selected from the group consisting of His, Asn, Gln, Lys and Arg Xaa₅ is an amino acid residue selected from the group consisting of Ala, Val, Leu, Ser and Ile;

Xaa₆ is an amino acid residue selected from the group consisting of Ala, Val, Leu, norleucine, Met, Phe, and Ile Xaa₇ is an amino acid residue selected from the group consisting of Ala, Val, Leu and Ile Xaa₈ is an amino acid residue selected from the group consisting of Glu and Asp, Xaa₉ is an amino acid residue selected from the group consisting of Glu and Asp, and wherein said amino acid residues Xaa₁, Xaa₃, Xaa₆, Xaa₇, Xaa₈ and Xaa₉ are not involved in antibody binding or to a smaller to significantly smaller extent as compared to the -His- and the -Phe-Phe- binding site, respectively.

In another embodiment of the invention, a chimeric antibody or a fragment thereof, or a humanized antibody or a fragment thereof is provided, wherein Xaa₃ is Gln or Asn, but particularly Gln;
Xaa₄ is Lys
Xaa₅ is Leu
Xaa₆ is Val or Leu, but particularly Val;
Xaa₇ is Ala or Val, but particularly Ala;
Xaa₈ is Glu or Asp, but particularly Glu; and
Xaa₉ is Asp or Glu, but particularly Asp.

In another embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein, wherein said at least one or said at least two distinct binding sites each comprise at least two consecutive amino acid residues predominantly involved in the binding of the antibody, wherein the at least two consecutive amino acid residues representing a second binding site are -Lys-Leu- embedded within the following core sequence (SEQ ID NO: 10):

Xaa₁-Xaa₂-Lys-Leu-Xaa₃ wherein

Xaa₁ is an amino acid residue selected from the group consisting of His, Asn, Gln Lys, and Arg;

Xaa₂ is an amino acid residue selected from the group consisting of Asn and Gln;

Xaa₃ is an amino acid residue selected from the group consisting of Ala, Val, Leu, norleucine, Met, Phe, and Ile; and wherein said amino acid residues Xaa₂, Xaa₃, are not involved in antibody binding or to a smaller to significantly smaller extent as compared to the -Lys-Leu- binding site.

In another embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least one and the at least two consecutive amino acids, which are separated by at least one amino acid residue not involved in antibody binding or to a significantly smaller extent as compared to the amino acid residues predominantly involved in the binding of the antibody, are -His- and -Lys-Leu-, respectively, embedded within the following core sequence:

His-Xaa₂-Lys-Leu-Xaa₃-Xaa₄-Xaa₅-Xaa₆--Xaa₇-Xaa₈- wherein

Xaa₂ is an amino acid residue selected from the group consisting of Asn and Gln;

Xaa₃ is an amino acid residue selected from the group consisting of Ala, Val, Leu, norleucine, Met, Phe, and Ile;

Xaa₄ is an amino acid residue selected from the group consisting of Ala, Val, Leu, norleucine, Met, Phe, and Ile Xaa₅ is an amino acid residue selected from the group consisting of Ala, Val, Leu, norleucine, Met, Phe, and Ile Xaa₆ is an amino acid residue selected from the group consisting of Ala, Val, Leu, Ser and Ile;

Xaa₇ is an amino acid residue selected from the group consisting of Glu and Asp, Xaa₈ is an amino acid residue selected from the group consisting of Glu and Asp and wherein said amino acid residues Xaa₂, Xaa₃, Xaa₆, Xaa₇, Xaa₈, are not involved in antibody binding or to a smaller to significantly smaller extent as compared to the -His- and the -Lys-Leu- binding site, respectively.

In another embodiment of the invention, a chimeric antibody or a fragment thereof, or a humanized antibody or a fragment thereof is provided, wherein Xaa₂ is Gln or Asn, but particularly Gln;
Xaa₃ is Val or Leu, but particularly Val;
Xaa₄ is Phe
Xaa₅ is Phe Xaa₆ is Ala or Val, but particularly Ala;
Xaa₇ is Glu or Asp, but particularly Glu; and
Xaa₈ is Asp or Glu, but particularly Asp.

In another embodiment of the invention, a chimeric antibody or a fragment thereof, or a humanized antibody or a fragment thereof is provided, which recognizes and binds to at least two distinct binding sites on the β-amyloid protein wherein said at least two distinct binding sites each comprise at least two consecutive amino acid residues predominantly involved in the binding of the antibody, wherein the at least two consecutive amino acids are separated by at least one amino acid residue not involved in antibody binding or to a significantly smaller extent than said consecutive amino acid residues, which are -Phe-Phe and -Lys-Leu-, respectively, representing a first and second binding site embedded within the following core sequence:

(SEQ ID NO: 11)
Xaa₁-Xaa₂-Lys-Leu-Xaa₃-Phe-Phe-Xaa₄-Xaa₅-Xaa₆, wherein
Xaa₁ is an amino acid residue selected from the group consisting of His, Asn, Gln Lys, and Arg;
Xaa₂ is an amino acid residue selected from the group consisting of Asn and Gln;
Xaa₃ is an amino acid residue selected from the group consisting of Ala, Val, Leu, norleucine, Met, Phe, and Ile;
Xaa₄ is an amino acid residue selected from the group consisting of Ala, Val, Leu, Ser and Ile;
Xaa₅ is an amino acid residue selected from the group consisting of Glu and Asp,
Xaa₆ is an amino acid residue selected from the group consisting of Glu and Asp and wherein said amino acid residues Xaa₂, Xaa₃, Xaa₄, Xaa₅ and Xaa₆ are not involved in antibody binding or to a smaller to significantly smaller extent as compared to the -Lys-Leu- and -Phe-Phe- binding site, respectively.

In another embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least one and the at least two consecutive amino acids are separated by at least one amino acid residue not involved in antibody binding or to a significantly smaller extent as compared to the amino acid residues, which are predominantly involved in the binding of the antibody, and wherein said amino acid residues are -His- and -Phe-Phe- and -Lys-Leu-, respectively, embedded within the following core sequence:

(SEQ ID NO: 33)
His-Xaa₂-Lys-Leu-Xaa₃-Phe-Phe-Xaa₄_Xaa₅_Xaa₆, wherein
Xaa₂ is an amino acid residue selected from the group consisting of Asn and Gln;
Xaa₃ is an amino acid residue selected from the group consisting of Ala, Val, Leu, norleucine, Met, Phe, and Ile;
Xaa₄ is an amino acid residue selected from the group consisting of Ala, Val, Leu, Ser and Ile;
Xaa₅ is an amino acid residue selected from the group consisting of Glu and Asp,
Xaa₆ is an amino acid residue selected from the group consisting of Glu and Asp, and wherein said amino acid residues Xaa₂, Xaa₃, Xaa₄, Xaa₅, Xaa₆, are not involved in antibody binding or to a smaller to significantly smaller extent as compared to the -His-, the -Lys-Leu- and the -Phe-Phe- binding site, respectively.

In another embodiment of the invention, a chimeric antibody or a fragment thereof, or a humanized antibody or a fragment thereof is provided, wherein
Xaa₂ is Gln or Asn, but particularly Gln;
Xaa₃ is Val or Leu, but particularly Val;
Xaa₄ is Ala or Val, but particularly Ala;
Xaa₅ is Glu or Asp, but particularly Glu; and
Xaa₆ is Asp or Glu, but particularly Asp.

In another embodiment of the invention, a chimeric antibody or a fragment thereof, or a humanized antibody or a fragment thereof is provided, which recognizes and binds to at least two distinct binding sites on the β-amyloid protein wherein said at least two distinct binding sites each comprise at least two consecutive amino acid residues predominantly involved in the binding of the antibody, wherein the at least two consecutive amino acids are separated by at least one amino acid residue not involved in antibody binding or to a significantly smaller extent than said consecutive amino acid residues, which are -Phe-Phe and -Lys-Leu-, respectively, representing a first and second binding site embedded within the following core sequence:

(SEQ ID NO: 34)
Xaa₁-Xaa₂-Lys-Leu-Xaa₃-Phe-Phe-Xaa₄-Xaa₅-Xaa₆, wherein
Xaa₁ is an amino acid residue selected from the group consisting of His, Asn, Gln, Lys and Arg;
Xaa₂ is an amino acid residue selected from the group consisting of Asn and Gln;
Xaa₃ is an amino acid residue selected from the group consisting of Val, Ala, Leu, Met, Phe, norleucine and Ile
Xaa₄ is an amino acid residue selected from the group consisting of Ala, Val, Leu and Ile;
Xaa₅ is an amino acid residue selected from the group consisting of Glu and Asp,
Xaa₆ is an amino acid residue selected from the group consisting of Glu and Asp, and wherein said amino acid residues Xaa₂, Xaa₃, Xaa₄, Xaa₅, Xaa₆, are not involved in antibody binding or to a smaller to significantly smaller extent as compared to the -Lys-Leu- and the -Phe-Phe binding site, respectively.

In another embodiment of the invention, a chimeric antibody or a fragment thereof, or a humanized antibody or a fragment thereof is provided, wherein
Xaa₁ is His or Arg, but particularly His;
Xaa₂ is Gln or Asn, but particularly Gln;
Xaa₃ is Val or Leu, but particularly Val;
Xaa₄ is Ala or Val, but particularly Ala;
Xaa₅ is Glu or Asp, but particularly Glu; and
Xaa₆ is Asp or Glu, but particularly Asp.

In one embodiment of the invention, a chimeric antibody or a fragment thereof, or a humanized antibody or a fragment thereof is provided which recognizes and binds to at least two distinct binding sites on the β-amyloid protein wherein said at least two distinct binding sites each comprise at least two consecutive amino acid residues predominantly involved in the binding of the antibody, which are -Phe-Phe-Ala-Glu- (SEQ ID NO: 35), particularly -Phe-Phe-Ala-, but especially -Phe-Phe- and -Lys-Leu-, respectively, and wherein said at least two distinct binding sites exhibit amino acid sequence -Val-Phe-Phe-Ala-Glu-Asp- shown in SEQ ID NO: 7 and amino acid sequence His-Gln-Lys-Leu-Val- shown in SEQ ID NO: 8, respectively.

In one embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein the said at least one or said at least two distinct binding sites comprise at least one and at least two consecutive amino acid residues, respectively, predominantly involved in the binding of the antibody, which are -Phe-Phe- and -Lys-Leu-, and -His-, respectively, wherein said distinct binding sites are embedded in the amino acid sequence -Val-Phe-Phe-Ala-Glu- (residues 1-5 of SEQ ID NO: 7), and amino acid sequence -His-Gln-Lys-Leu-Val- (SEQ ID NO: 8), respectively.

In another embodiment of the invention, the chimeric antibody or a fragment thereof, or a humanized antibody or a fragment thereof comprises an antigen recognition and binding site which recognizes and binds to at least two distinct binding sites on the β-amyloid protein wherein said at least two distinct binding sites each comprise at least two consecutive amino acid residues within the amino acid sequence given in SEQ ID NOs: 7 and 8, respectively, wherein said consecutive amino acid residues, particularly -Phe-Phe- and -Lys-Leu-, are predominantly involved in the binding of the β-amyloid protein.

In a further specific embodiment of the invention, an antibody or a fragment thereof according to the invention is provided, which binds to 4 distinct binding sites on the β-amyloid protein wherein said 4 distinct binding sites include 2 binding sites each comprising one amino acid residue and 2 binding sites each comprising two consecutive amino acid residues, which residues are predominantly involved in the binding of the antibody, wherein said 4 distinct binding sites are located in close proximity to each other on the β-amyloid protein, and wherein said 4 binding sites are separated by at least one amino acid residue not involved in antibody binding or involved in binding but to a significantly smaller extent as compared to said one amino acid residue and said two consecutive amino acid residues of the 4 distinct binding sites thus forming a conformational discontinuous epitope.

In particular, the first of the two consecutive amino acid residues predominantly involved in the binding of the antibody is -Lys-Leu-, and the second of the at least two consecutive amino acid residues is -Phe-Phe-, the first of the single amino acid residues is -His- and the second of the single amino acid residues is -Asp- embedded within the following core sequence:

(SEQ ID NO: 36)
-Xaa$_1$-His-Xaa$_2$-Lys-Leu-Xaa$_3$-Phe-Phe-Xaa$_4$-Xaa$_5$-Asp,

-Xaa$_6$ wherein
Xaa$_1$ is an amino acid residue selected from the group consisting of His, Asn, Gln, Lys and Arg, but particularly His;
Xaa$_2$ is an amino acid residue selected from the group consisting of Asn and Gln, but particularly Gln;
Xaa$_3$ is an amino acid residue selected from the group consisting of Ala, Val, Leu, norleucine, Met, Phe, and Ile, particularly Val;
Xaa$_4$ is an amino acid residue selected from the group consisting of Ala, Val, Leu, Ser and Ile, particularly Ala;
Xaa$_5$ is an amino acid residue selected from the group consisting of Glu and Asp, particularly Glu;
Xaa$_6$ is an amino acid residue selected from the group consisting of Ala, Val, Leu, norleucine, Met, Phe, and Ile, particularly Val; and wherein said amino acid residues Xaa$_1$, Xaa$_2$, Xaa$_3$ Xaa$_4$, Xaa$_5$, Xaa$_6$, are not involved in antibody binding or are involved in binding but to a significantly smaller extent as compared to the -His-, -Asp-, the -Lys-Leu, and the -Phe-Phe- binding site.

In one embodiment, the invention relates to an antibody or a fragment thereof according to the invention, which binds to 4 distinct binding sites on the β-amyloid protein, wherein said 4 distinct binding sites include two binding sites each comprising one amino acid residue and two binding sites each comprising two consecutive amino acid residues, wherein the first of the two consecutive amino acid residues predominantly involved in the binding of the antibody is -Lys-Leu-, and the second of the at least two consecutive amino acid residues is -Phe-Phe-, the first of the single amino acid residues is -His- and the second of the single amino acid residues is -Asp- embedded within the following core sequence:

(SEQ ID NO: 36)
-Xaa$_1$-His-Xaa$_2$-Lys-Leu-Xaa$_3$-Phe-Phe-Xaa$_4$-Xaa$_5$-Asp,

-Xaa$_6$ wherein
Xaa$_1$ is an amino acid residue selected from the group consisting of His, Asn, Gln, Lys and Arg, but particularly His;
Xaa$_2$ is an amino acid residue selected from the group consisting of Asn and Gln, but particularly Gln;
Xaa$_3$ is an amino acid residue selected from the group consisting of Ala, Val, Leu, norleucine, Met, Phe, and Ile, particularly Val;
Xaa$_4$ is an amino acid residue selected from the group consisting of Ala, Val, Leu, Ser and Ile, particularly Ala;
Xaa$_5$ is an amino acid residue selected from the group consisting of Glu and Asp, particularly Glu;
Xaa$_6$ is an amino acid residue selected from the group consisting of Ala, Val, Leu, norleucine, Met, Phe, and Ile, particularly Val; and wherein said amino acid residues Xaa$_1$, Xaa$_2$, Xaa$_3$, Xaa$_4$, Xaa$_5$, Xaa$_6$, are not involved in antibody binding or are involved in binding but to a significantly smaller extent as compared to the -His-, -Asp-, the -Lys-Leu, and the -Phe-Phe- binding site.

In a specific embodiment of the invention, the recognition and binding sites as defined herein before are forming a conformational discontinuous epitope localized in a region of the β-amyloid protein between amino acid residue 12 to 24, particularly between residues 14 to 23, more particularly between amino acid residues 14 and 20, wherein the at least two distinct recognition and binding sites each comprising at least 2 amino acid residues, are located at position 16 and 17 and at position 19 and 20, respectively, and wherein the at least one distinct recognition and binding site comprising at least 1 amino acid residue is located at position 14, which residues are predominantly involved in the binding of the β-amyloid protein and wherein said distinct recognition and binding sites are at least on one side flanked by amino acid residues, particularly residues 21 and 22, and separated by one amino acid residue located at position 15 and 18, which amino acid residues are not directly involved in the binding of the antigen or, at least, to a substantially smaller extent.

In still another embodiment of the invention the said at least three distinct recognition and binding sites are flanked on both sides by amino acid residues, particularly residues 12 and 13, and residues 21 and 22 and are separated by one amino acid residue located at position 15 and 18, which amino acid residues are not directly involved in the binding of the antigen or, at least, to a substantially smaller extent.

In a specific embodiment, said consecutive amino acid residues, particularly -Lys-Leu- at position 16 and 17 and -Phe-Phe- at position 19 and 20, which are predominantly involved in the binding of the β-amyloid protein, are embedded into the following core region (SEQ ID NO: 37):

| Val- | His- | His- | Gln- | Lys- | Leu- | Val- | Phe- | Phe- | Ala- | Glu- | Asp |
|---|---|---|---|---|---|---|---|---|---|---|---|
| 12 | 13 | 14 | 15 | 16 | 17 | 18 | 19 | 20 | 21 | 22 | 23 |

In another specific embodiment, said amino acid residues, particularly -Lys-Leu- at position 16 and 17 and -Phe-Phe- at position 19 and 20, and -His- at position 14, which are predominantly involved in the binding of the β-amyloid protein, are embedded into the following core region (SEQ ID NO: 38):

| Val- | His- | His- | Gln- | Lys- | Leu- | Val- | Phe- | Phe- | Ala- | Glu- | Asp- | Val- | Gly- |
|---|---|---|---|---|---|---|---|---|---|---|---|---|---|
| 12 | 13 | 14 | 15 | 16 | 17 | 18 | 19 | 20 | 21 | 22 | 23 | 24 | 25 |

In another embodiment of the invention, a humanized antibody or a fragment thereof is provided which comprises in the light chain and heavy chain variable region, respectively, at least one CDR of non-human origin, particularly two CDRs of non-human origin, more particularly three CDR of non-human origin, embedded in one or more human- or primate-derived framework regions and, optionally, a constant region derived from a human or primate source antibody, which humanized antibody or fragment thereof is capable of specifically recognizing and binding β-amyloid protein, particularly a β-amyloid monomeric peptide, more particularly a β-amyloid polymeric peptide, even more particularly β-amyloid fibers, fibrils or filaments in isolation or as part of a β-amyloid plaque, at an epitope comprising the following amino acid sequence (SEQ ID NO: 11):

$Xaa_1$-$Xaa_2$-Lys-Leu-$Xaa_3$-Phe-Phe-$Xaa_4$_$Xaa_5$_$Xaa_6$, wherein
$Xaa_1$ is an amino acid residue selected from the group consisting of His, Asn, Gln, but particularly His;
$Xaa_2$ is an amino acid residue selected from the group consisting of Asn and Gln, but particularly Gln; and
$Xaa_3$ is an amino acid residue selected from the group consisting of Val, Leu, and Ile, but particularly Val;
$Xaa_4$ is an amino acid residue selected from the group consisting of Ala and Val, but particularly Ala;
$Xaa_5$ is an amino acid residue selected from the group consisting of Glu and Asp, but particularly Glu;

$Xaa_6$ is an amino acid residue selected from the group consisting of Glu and Asp, but particularly Asp.

In still another embodiment of the invention, a humanized antibody or a fragment thereof is provided which comprises in the light chain and heavy chain variable region, respectively, at least one CDR of non-human origin, particularly two CDRs of non-human origin, more particularly three CDR of non-human origin, embedded in one or more human- or primate-derived framework regions and, optionally, a constant region derived from a human or primate source antibody, which humanized antibody or fragment thereof is capable of specifically recognizing and binding β-amyloid protein, particularly a β-amyloid monomeric peptide, more particularly a β-amyloid polymeric peptide, even more particularly β-amyloid fibers, fibrils or filaments in isolation or as part of a β-amyloid plaque, at an epitope comprising the following amino acid sequence:

(SEQ ID NO: 39)
His-$Xaa_2$-Lys-Leu-$Xaa_3$-Phe-Phe-$Xaa_4$_$Xaa_5$_$Xaa_6$, wherein $Xaa_2$ is an amino acid residue selected from the group consisting of Asn and Gln, but particularly Gln; and
$Xaa_3$ is an amino acid residue selected from the group consisting of Val, Leu, and Ile, but particularly Val;
$Xaa_4$ is an amino acid residue selected from the group consisting of Ala and Val, but particularly Ala;
$Xaa_5$ is an amino acid residue selected from the group consisting of Glu and Asp, but particularly Glu;
$Xaa_6$ is an amino acid residue selected from the group consisting of Glu and Asp, but particularly Glu; and wherein said amino acid residues $Xaa_2$, $Xaa_3$, $Xaa_4$ $Xaa_5$, $Xaa_6$, are not involved in antibody binding or to a smaller extent as compared to the -His- and the -Lys-Leu- and the -Phe-Phe- binding site.

In a specific embodiment of the invention, the CDR of non-human origin is obtained from a donor antibody, but particularly from a murine donor antibody, raised against an antigen fragment which does not contain said distinct binding site. This shift in the epitopic region may have at least partially been caused by the use of a supramolecular antigenic construct comprising an antigenic peptide corresponding to the amino acid sequence of the β-amyloid peptide, particularly of β-amyloid peptide $A\beta_{1-16}$, modified with a hydrophilic moiety such as, for example, polyethylene glycol (PEG), wherein said hydrophilic moiety is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophilic moiety to the peptide fragment, as described herein below in the immunization process. When a PEG is used as the hydrophilic moiety, the free PEG termini are covalently bound to phosphatidylethanolamine or any other compound suitable to function as the anchoring element, for example, to embed the antigenic construct in the bilayer of a liposome as described herein.

In particular, the CDR of non-human origin is obtained from a murine donor antibody which exhibits the characteristic properties of ACI-01-Ab7C2 (also named "mC2" throughout the application) deposited 1 Dec. 2005 with the "Deutsche Sammlung von Mikroorganismen und Zellkulturen GmbH (DSMZ) in Braunschweig, Mascheroder Weg 1 B, 38124 Branuschweig, under the provisions of the Budapest Treaty under accession no DSM ACC2750).

In one embodiment of the invention, the CDR of non-human origin is obtained from murine donor antibody ACI-01-Ab7C2 (also named "mC2" throughout the application) deposited 1 Dec. 2005 with the "Deutsche Sammlung von Mikroorganismen und Zellkulturen GmbH (DSMZ) in Braunschweig, Mascheroder Weg 1 B, 38124 Branuschweig, under the provisions of the Budapest Treaty under accession no DSM ACC2750).

Also the use of lipid A as part of the immunization protocol may have contributed to a shift in the epitopic region.

In a specific embodiment, the invention relates to a humanized antibody or a fragment thereof comprising integrated into human- or primate-derived framework regions at least one peptide with an amino acid sequence selected from the group of sequences consisting of SEQ ID NO: 2 representing CDR2 and SEQ ID NO: 3 representing CDR3 of the Heavy Chain Variable Region (HCVR) and SEQ ID NO: 4 representing CDR1 of the Light Chain Variable Region (LCVR).

In another embodiment, the invention relates to a humanized antibody or a fragment thereof, wherein said humanized antibody comprises integrated into human- or primate-derived heavy chain framework regions at least one peptide with an amino acid sequence selected from the group of sequences consisting of SEQ ID NO: 2 representing CDR2 and SEQ ID NO: 3 representing CDR3 of the Heavy Chain Variable Region (HCVR).

In still another embodiment, the invention relates to a humanized antibody or a fragment thereof, wherein said humanized antibody comprises integrated into human- or primate-derived light chain framework regions a peptide with an amino acid sequence of SEQ ID NO: 4 representing CDR1 of the Light Chain Variable Region (LCVR).

In particular, the invention relates to a Light Chain Variable Region (LCVR) comprising integrated into human- or primate-derived framework regions at least one peptide with an amino acid sequence of SEQ ID NO: 4 representing CDR1 of the Light Chain Variable Region (LCVR).

In another specific embodiment, the invention relates to a Heavy Chain Variable Region (HCVR) comprising integrated into human- or primate-derived framework regions at least one peptide with an amino acid sequence selected from the group of sequences consisting of SEQ ID NO: 2 representing CDR2 and SEQ ID NO: 3 representing CDR3 of the Heavy Chain Variable Region (HCVR).

The invention further relates to a humanized antibody or a fragment thereof, which comprises integrated into human- or primate-derived framework regions at least two peptides, which peptides are different and exhibit an amino acid sequence selected from the group of sequences consisting of SEQ ID NO:1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR) wherein the same CDR cannot be present twice in the antibody. In particular, if the at least two CDRs present are both CDRs of the Light Chain Variable Region (LCVR), at least on of said CDRs must be CDR1 represented by SEQ ID NO: 4.

Also comprised by the invention is a humanized antibody or a fragment thereof comprising integrated into human- or primate-derived heavy chain framework regions at least two peptides with an amino acid sequence selected from the group of sequences consisting of SEQ ID NO: 1 representing CDR1, SEQ ID NO: 2 representing CDR2 and SEQ ID NO: 3 representing CDR3 of the Heavy Chain Variable Region (HCVR), but particularly a humanized antibody or a fragment thereof wherein the same CDR cannot be present twice in the antibody.

In particular, the invention relates to a Heavy Chain Variable Region (HCVR) comprising integrated into human- or primate-derived heavy chain framework regions at least two peptides with an amino acid sequence selected from the group of sequences consisting of SEQ ID NO: 1 representing CDR1, SEQ ID NO: 2 representing CDR2 and SEQ ID NO: 3 representing CDR3 of the Heavy Chain Variable Region (HCVR).

In a further embodiment, the invention relates to a humanized antibody or a fragment thereof, comprising integrated into human- or primate-derived light chain framework regions at least two peptides with an amino acid sequence selected from the group of sequences consisting of SEQ ID NO: 4 representing CDR1, SEQ ID NO: 5 representing CDR2 and SEQ ID NO: 6 representing CDR3 of the Light Chain Variable Region (LCVR).

In particular, the invention relates to a Light Chain Variable Region (LCVR), which has integrated into human- or primate-derived light chain framework regions at least two peptides with an amino acid sequence selected from the group of sequences consisting of SEQ ID NO: 4 representing CDR1, SEQ ID NO: 5 representing CDR2 and SEQ ID NO: 6 representing CDR3 of the Light Chain Variable Region (LCVR), wherein the same CDR cannot be present twice in the antibody and, in particular, at least on of said CDRs must be CDR1 represented by SEQ ID NO: 4.

The invention also relates to a humanized antibody or a fragment thereof, comprising integrated into human- or primate-derived heavy chain framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR), particularly in the order indicated above.

In particular, the invention relates to a Heavy Chain Variable Region (HCVR) comprising integrated into human- or primate-derived heavy chain framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR), particularly in the order indicated above.

Also comprised by the invention is a humanized antibody or a fragment thereof comprising integrated into human- or primate-derived light chain framework regions peptides with an amino acid sequence of SEQ ID NO: 4 representing CDR1, SEQ ID NO: 5 representing CDR2 and SEQ ID NO: 6 representing CDR3 of the Light Chain Variable Region (LCVR), particularly in the order indicated above.

In particular, the invention relates to a Light Chain Variable Region (LCVR) comprising integrated into human- or primate-derived light chain framework regions peptides with an amino acid sequence of SEQ ID NO: 4 representing CDR1, SEQ ID NO: 5 representing CDR2 and SEQ ID NO: 6 representing CDR3 of the Light Chain Variable Region (LCVR), particularly in the order indicated above.

The invention also relates to a humanized antibody or a fragment thereof, which comprises integrated into human- or primate-derived framework regions at least three peptides with an amino acid sequence selected from the group of sequences consisting of SEQ ID NO: 1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR), but particularly a humanized antibody or a fragment thereof wherein the same CDR cannot be present twice in the antibody.

In another embodiment the invention relates to a humanized antibody or a fragment thereof, which antibody comprises integrated into human- or primate-derived framework regions at least four peptides with an amino acid sequence selected from the group of sequences consisting of SEQ ID NO: 1 representing CDR1, SEQ ID NO: 2 representing CDR2 and SEQ ID NO:3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR), but particularly a humanized antibody or a fragment thereof wherein the same CDR cannot be present twice in the antibody.

In still another embodiment, the invention relates to a humanized antibody or a fragment thereof, which comprises integrated into human- or primate-derived framework regions at least five peptides with an amino acid sequence selected from the group of sequences consisting of SEQ ID NO: 1 representing CDR1, SEQ ID NO: 2 representing CDR2 and SEQ ID NO:3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR), but particularly a humanized antibody or a fragment thereof wherein the same CDR cannot be present twice in the antibody.

In still another embodiment, the invention relates to a humanized antibody or a fragment thereof, which comprises integrated into human- or primate-derived framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR).

In a specific embodiment, the invention relates to a humanized antibody, a Heavy Chain Variable Region (HCVR), or a fragment thereof, wherein said humanized antibody, Heavy Chain Variable Region (HCVR) or fragment thereof comprises integrated into human- or primate-derived heavy chain framework regions at least a peptide with an amino acid sequence of SEQ ID NO: 2 representing CDR2 of the Heavy Chain Variable Region (HCVR).

In another specific embodiment, the invention relates to a humanized antibody, a Heavy Chain Variable Region (HCVR) or a fragment thereof, wherein said humanized antibody, Heavy Chain Variable Region (HCVR) or fragment thereof comprises integrated into human- or primate-derived heavy chain framework regions at least a peptide with an amino acid sequence of SEQ ID NO: 3 representing CDR3 of the Heavy Chain Variable Region (HCVR).

In another specific embodiment, the invention relates to a humanized antibody, Heavy Chain Variable Region (HCVR) or a fragment thereof, which antibody, Heavy Chain Variable Region (HCVR) or fragment thereof comprises integrated into human- or primate-derived heavy chain framework regions at least two peptides with an amino acid sequence of SEQ ID NO: 1 representing CDR1 and SEQ ID NO: 2 representing CDR2 of the Heavy Chain Variable Region (HCVR).

In another specific embodiment, the invention relates to a humanized antibody, a Heavy Chain Variable Region (HCVR) or a fragment thereof, which antibody, Heavy Chain Variable Region (HCVR) or fragment thereof comprises integrated into human- or primate-derived heavy chain framework regions at least two peptides with an amino acid sequence of SEQ ID NO: 1 representing CDR1 and SEQ ID NO: 3 representing CDR3 of the Heavy Chain Variable Region (HCVR).

In another specific embodiment, the invention relates to a humanized antibody, a Heavy Chain Variable Region (HCVR) or a fragment thereof, which antibody, Heavy Chain Variable Region (HCVR) or fragment thereof comprises integrated into human- or primate-derived heavy chain framework regions at least two peptides with an amino acid sequence of SEQ ID NO: 2 representing CDR2 and SEQ ID NO: 3 representing CDR3 of the Heavy Chain Variable Region (HCVR).

In another specific embodiment, the invention relates to a humanized antibody, a Light Chain Variable Region (LCVR) or a fragment thereof, which antibody, Light Chain Variable Region (LCVR) or fragment thereof comprises integrated into human- or primate-derived heavy chain framework regions at least two peptides with an amino acid sequence of SEQ ID NO: 4 representing CDR1 and SEQ ID NO: 5 representing CDR2 of the Light Chain Variable Region (LCVR).

In another specific embodiment, the invention relates to a humanized antibody, a Light Chain Variable Region (LCVR) or a fragment thereof, which antibody, Light Chain Variable Region (LCVR) or fragment thereof comprises integrated into human- or primate-derived heavy chain framework regions at least two peptides with an amino acid sequence of SEQ ID NO: 4 representing CDR1 and SEQ ID NO: 6 representing CDR3 of the Light Chain Variable Region (LCVR).

Further comprised by the invention is a humanized antibody or a fragment thereof, wherein both the Heavy Chain Variable Region (HCVR) and the Light Chain Variable Region (LCVR) of the mouse C2 antibody each contributes at least one of its CDR regions to the at least two CDR regions of the humanized antibody. The resulting humanized antibody or a fragment thereof thus may comprise at least an amino acid sequence of SEQ ID NO: 1 representing CDR1 (HCVR) in combination with an amino acid sequence of SEQ ID NO: 4 representing CDR1 (LCVR);

at least an amino acid sequence of SEQ ID NO: 2 representing CDR2 (HCVR) in combination with an amino acid sequence of SEQ ID NO: 4 representing CDR1 (LCVR);

at least an amino acid sequence of SEQ ID NO: 3 representing CDR3 (HCVR) in combination with an amino acid sequence of SEQ ID NO: 4 representing CDR1 (LCVR);

at least an amino acid sequence of SEQ ID NO: 1 representing CDR1 (HCVR) in combination with an amino acid sequence of SEQ ID NO: 5 representing CDR2 (LCVR);

at least an amino acid sequence of SEQ ID NO: 2 representing CDR2 (HCVR) in combination with an amino acid sequence of SEQ ID NO: 5 representing CDR2 (LCVR);

at least an amino acid sequence of SEQ ID NO:2 representing CDR2 (HCVR) in combination with an amino acid sequence of SEQ ID NO: 6 representing CDR3 (LCVR);

at least an amino acid sequence of SEQ ID NO:1 representing CDR1 (HCVR) in combination with an amino acid sequence of SEQ ID NO: 6 representing CDR3 (LCVR);

at least an amino acid sequence of SEQ ID NO: 3 representing CDR3 (HCVR) in combination with an amino acid sequence of SEQ ID NO: 5 representing CDR2 (LCVR);

at least an amino acid sequence of SEQ ID NO: 3 representing CDR3 (HCVR) in combination with an amino acid sequence of SEQ ID NO: 6 representing CDR3 (LCVR).

In still another embodiment, the invention relates to a chimeric antibody or a fragment thereof, or a humanized antibody or a fragment thereof as described herein before, which antibody comprises a light chain and/or a heavy chain constant region of human or primate origin.

In a further embodiment, the invention relates to a chimeric antibody or a fragment thereof, or a humanized antibody or a fragment thereof, wherein at least one, particularly at least one but not more than 5, more particularly at least one but not more than 4, even more particularly at least one but not more than 3, but especially at least one but not more than 2, of the amino acids representative of the light chain and/or heavy chain CDR regions as given in SEQ ID NOs: 1-6 is changed through a conservative substitution such that the antibody maintains its full functionality.

In particular, the invention relates to a chimeric antibody or a fragment thereof, or a humanized antibody or a fragment thereof, wherein in CDR2 of the light chain variable region (LCVR) as given in SEQ ID NO: 5, the Lys at Kabat position 50 is replaced by an amino acid residue selected from the group consisting of Arg, Gln and Glu, particularly by Arg.

In particular, the invention relates to a light chain variable region (LCVR) wherein in CDR2 as given in SEQ ID NO: 5, the Lys at Kabat position 50 is replaced by an amino acid residue selected from the group consisting of Arg, Gln and Glu, particularly by Arg.

In another embodiment, the invention relates to a chimeric antibody or a fragment thereof, or a humanized antibody or a fragment thereof, wherein in CDR2 of the light chain variable region (LCVR) as given in SEQ ID NO: 5, the Ser at Kabat position 53 is replaced by an amino acid residue selected from the group consisting of Asn or Thr, but particularly by Asn.

In particular, the invention relates to a light chain variable region (LCVR) wherein in CDR2 as given in SEQ ID NO: 5, the Ser at Kabat position 53 is replaced by an amino acid residue selected from the group consisting of Asn or Thr, but particularly by Asn.

In one embodiment of the invention, a chimeric antibody or a fragment thereof, or a humanized antibody or a fragment thereof is provided, wherein the Heavy Chain Variable Region (HCVR) has an amino acid sequence that is 90%, particularly 95%, more particularly 98% identical to the sequence given in SEQ ID NO: 15 and 16, respectively.

In another embodiment of the invention, a chimeric antibody or a fragment thereof, or a humanized antibody or a fragment thereof is provided, wherein the Light Chain Variable Region (LCVR) has an amino acid sequence that is 90%, particularly 95%, more particularly 98% identical to the sequence given in SEQ ID NO: 12 and 13, respectively.

In still another embodiment of the invention, a humanized antibody or a fragment thereof is provided, wherein at least two, but especially three, of the CDR regions of the Heavy Chain Variable Region (HCVR) have an amino acid sequence that is 90%, particularly 95%, more particularly 98% identical to the corresponding CDR region as given in SEQ ID NO: 1-3.

In a further embodiment of the invention, a humanized antibody or a fragment thereof is provided, wherein at least two, but especially three, of the CDR regions of the Light Chain Variable Region (LCVR) have an amino acid sequence that is 90%, particularly 95%, more particularly 98% identical to the corresponding CDR region as given in SEQ ID NO: 4-6.

In still another embodiment, the invention relates to a chimeric antibody or a fragment thereof, or a humanized antibody or a fragment thereof according to the present invention as described herein before wherein the Heavy Chain Variable Region (HCVR) has an amino acid sequence that is 90%, 91%, 92%, 93%, 94%, 95%, 96%, 97%, 98% or 99% identical to the sequence given in SEQ ID NO: 15 and 16, respectively.

In still another embodiment, the invention relates to a chimeric antibody or a fragment thereof, or a humanized antibody or a fragment thereof according to the present invention as described herein before wherein the Light Chain Variable Region (LCVR) has an amino acid sequence that is 90%, 91%, 92%, 93%, 94%, 95%, 96%, 97%, 98% or 99% identical to the sequence given in SEQ ID NO: 12 and 13, respectively.

In still another embodiment, the invention relates to a chimeric antibody or a fragment thereof, or a humanized antibody or a fragment thereof according to the present invention as described herein before, wherein at least one, particularly at least two, but especially three, of the CDR regions of the Heavy Chain Variable Region (HCVR) have an amino acid sequence that is 90%, 91%, 92%, 93%, 94%, 95%, 96%, 97%, 98% or 99% identical to the corresponding CDR region as given in SEQ ID NO: 1-3.

In still another embodiment, the invention relates to a chimeric antibody or a fragment thereof, or a humanized antibody or a fragment thereof according to the present invention as described herein before, wherein at least one, particularly at least two, but especially three, of the CDR regions of the Light Chain Variable Region (LCVR) have an amino acid sequence that is 90%, 91%, 92%, 93%, 94%, 95%, 96%, 97%, 98% or 99% identical to the corresponding CDR region as given in SEQ ID NO: 4-6.

In still another embodiment, the invention relates to a humanized antibody according to the present invention and as described herein before, wherein at least one of the amino acids representative of the acceptor framework sequences obtained from human germline $V_H$ and $V_K$ sequences, respectively is changed through a substitution to an amino acid from the corresponding region of murine antibody ACI-01-Ab7C2 or a substitution conservative thereto.

In particular, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu such as shown in SEQ ID NO: 15.

The invention further relates to a Heavy Chain Variable Region and to a humanized antibody comprising this Heavy Chain Variable Region, respectively, wherein the Arg in Kabat position 94 in the acceptor framework sequence obtained from human germline $V_H$ sequences of KABAT subgroup $V_H$III of the Heavy Chain Variable Region is replaced by an amino acid selected from the group consisting of Ser and Thr, but especially by Ser such as shown in SEQ ID NO: 15 . . . .

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 is replaced by an amino acid selected from the group consisting of Ser and Thr, but especially by Ser such as shown in SEQ ID NO: 15.

The invention further relates to a Light Chain Variable Region and to a humanized antibody comprising this Light Chain Variable Region, respectively, wherein the Gln in Kabat position 45 in the acceptor framework sequence obtained from human germline $V_K$ sequences of KABAT subgroup $V_K$II of the Light Chain Variable Region is replaced by an amino acid selected from the group consisting of Lys, Arg, Gln, and Asn, particularly by Lys and Arg, but especially by Lys.

The invention further relates to a Light Chain Variable Region and to a humanized antibody comprising this Light Chain Variable Region, respectively, wherein the Tyr in Kabat position 87 in the acceptor framework sequence obtained from human germline $V_K$ sequences of KABAT subgroup $V_K$II of the Light Chain Variable Region is replaced by an amino acid selected from the group consisting of Phe, Leu, Val, Ile, and Ala, particularly by Leu and Phe, but especially by Phe.

The invention further relates to a Light Chain Variable Region and to a humanized antibody comprising this Light Chain Variable Region, respectively, wherein the Lys in Kabat position 50 in the CDR2 region obtained from a mouse monoclonal antibody, particularly murine antibody ACI-01-Ab7C2, such as shown in SEQ ID NO: 12 is replaced by an amino acid selected from the group consisting of Arg, Gln, His, and Asn, but especially by Arg In still another embodiment, the invention relates to a Light Chain Variable Region and to a humanized antibody comprising this Light Chain Variable Region, respectively, wherein the Asn in Kabat position 53 in the CDR2 region obtained from a mouse monoclonal antibody, particularly murine antibody ACI-01-Ab7C2, such as shown in SEQ ID NO: 12 is replaced by an amino acid selected from the group consisting of Ala, Val, Leu, Ser and Ile; but especially Ser.

In still another embodiment, the invention relates to a humanized antibody, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 in the acceptor framework sequence obtained from human germline $V_H$ sequences of KABAT subgroup $V_H$III of the Heavy Chain Variable Region is replaced by an amino acid selected from the group consisting of Ser and Thr, but especially by Ser as shown in SEQ ID NO: 15, and the Tyr in Kabat position 87 in the acceptor framework sequence obtained from human germline $V_K$ sequences of KABAT subgroup $V_K$II of the Light Chain Variable Region is replaced by an amino acid selected from the group consisting of Phe, Leu, Val, Ile, and Ala, particularly by Leu and Phe, but especially by Phe.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region as shown in SEQ ID NO: 15 is replaced by Leu.

In still another embodiment, the invention relates to a Heavy Chain Variable Region and to a humanized antibody comprising this Heavy Chain Variable Region, respectively, wherein the Arg in Kabat position 94 in the acceptor framework sequence obtained from human germline $V_H$ sequences of KABAT subgroup $V_H$III of the Heavy Chain Variable Region is replaced by Ser such as shown in SEQ ID NO: 15.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by Leu and Ile, but especially Leu and the Arg in Kabat position 94 in the acceptor framework sequence obtained from human germline $V_H$ sequences of KABAT subgroup $V_H$III of the Heavy Chain Variable Region is replaced by Ser such as shown in SEQ ID NO: 15.

In still another embodiment, the invention relates to a Light Chain Variable Region and to a humanized antibody comprising this Heavy Chain Variable Region, respectively, wherein the Tyr in Kabat position 87 in the acceptor framework sequence obtained from human germline $V_K$ sequences of KABAT subgroup $V_K$II of the Light Chain Variable Region is replaced by Phe.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by Leu and Ile, but especially Leu and the Arg in Kabat position 94 in the acceptor framework sequence obtained from human germline $V_H$ sequences of KABAT subgroup $V_H$III of the Heavy Chain Variable Region is replaced by Ser such as shown in SEQ ID NO: 15 and the Tyr in Kabat position 87 in the acceptor framework sequence obtained from human germline $V_K$ sequences of KABAT subgroup $V_K$II of the Light Chain Variable Region is replaced by Phe.

In one embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 is replaced by an amino acid selected from the group consisting of Ser and Thr, but especially by Ser such as shown in SEQ ID NO: 15 and wherein the Lys in Kabat position 50 in the CDR2 region obtained from a mouse monoclonal antibody, particularly murine antibody ACI-01-Ab7C2, is replaced by an amino acid selected from the group consisting of Arg, Gln, His, and Asn, but especially by Arg.

In one embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 is replaced by an amino acid selected from the group consisting of Ser and Thr, but especially by Ser such as shown in SEQ ID NO: 15 and wherein the Asn in Kabat position 53 in the CDR2 region obtained from a mouse monoclonal antibody, particularly murine antibody ACI-01-Ab7C2, is replaced by an amino acid selected from the group consisting of Ala, Val, Leu, Ser and Ile; but especially Ser.

In a specific embodiment, the invention relates to the light chain variable region of SEQ ID NO: 12.

In another specific embodiment of the invention, a humanized antibody is provided, which comprises the light chain variable region of SEQ ID NO: 12.

In a specific embodiment, the invention relates to the light chain variable region including signal sequences as shown in SEQ ID NO: 13.

In another specific embodiment of the invention, a humanized antibody is provided, which comprises the complete light chain variable region including signal sequences as shown in SEQ ID NO: 13.

In another specific embodiment of the invention, a humanized antibody is provided, which comprises the light chain variable region of SEQ ID NO: 12 and the light chain constant region of SEQ ID NO: 14.

In another specific embodiment of the invention, a humanized antibody is provided, which comprises the complete light chain variable region of SEQ ID NO: 13 and the light chain constant region of SEQ ID NO: 14.

In a specific embodiment, the invention relates to the heavy chain variable region of SEQ ID NO: 15.

In another specific embodiment of the invention, a humanized antibody is provided, which comprises the heavy chain variable region of SEQ ID NO: 15.

In a specific embodiment, the invention relates to the heavy chain variable region including signal sequences as shown in SEQ ID NO: 16.

In another specific embodiment of the invention, a humanized antibody is provided, which comprises the complete heavy chain variable region including signal sequences as shown in SEQ ID NO: 16.

In another specific embodiment of the invention, a humanized antibody is provided, which comprises the heavy chain variable region of SEQ ID NO: 15 and the heavy chain constant region of SEQ ID NO: 17.

In another specific embodiment of the invention, a humanized antibody is provided, which comprises the heavy chain variable region of SEQ ID NO: 16 and the heavy chain constant region of SEQ ID NO: 17.

In one embodiment the humanized antibody according to the invention and as described herein, upon co-incubation with an Aβ monomeric peptide having at least 30, particularly at least 35, more particularly at least 38, even more particularly at least 40 amino acid residues and/or an Aβ polymeric soluble amyloid peptide comprising a plurality of said Aβ monomeric units, but especially with an $Aβ_{1-42}$ monomeric and/or an Aβ polymeric soluble amyloid peptide comprising a plurality of said $Aβ_{1-42}$ monomeric units, particularly at a molar concentration ratio of antibody to Aβ1-42 of up to 1:1000, particularly of up to 1:500, more particularly of up to 1:300, even more particularly of up to 1:200, but especially at a molar concentration ratio of between 1:10 and 1:100, inhibits the aggregation of the Aβ monomers to high molecular polymeric fibrils.

In particular, the co-incubation of the antibody according to the invention with amyloid monomeric and/or polymeric soluble amyloid peptides is carried out for 24 hours to 60 hours, particularly for 30 hours to 50 hours, more particularly for 48 hours, but especially 24 hours, at a temperature of between 28° C. and 40° C., particularly of between 32° C. and 38° C., more particularly at 37° C.

In a specific embodiment of the invention, co-incubation with amyloid monomeric and/or polymeric soluble amyloid peptides is accomplished for 24 hours at a temperature of 37° C.

In particular, the antibody, particularly the humanized antibody according to the invention including any functionally equivalent antibody or functional parts thereof binds to $Aβ_{1-42}$ monomeric peptide and/or Aβ polymeric soluble amyloid peptide comprising a plurality of said $Aβ_{1-42}$ monomeric units and, upon co-incubation with $Aβ_{1-42}$ monomeric peptide and/or Aβ polymeric soluble amyloid peptide comprising a plurality of said $Aβ_{1-42}$ monomeric units inhibits the aggregation of the Aβ monomers and/or polymers to high molecular polymeric fibrils.

In one embodiment, the antibody, particularly the humanized antibody according to the invention including any functionally equivalent antibody or functional parts thereof inhibits the aggregation of the Aβ monomers and/or Aβ soluble polymers comprising a plurality of said Aβ monomeric units to high molecular polymeric fibrils by at least 50%, particularly by at least 60%, particularly by at least 65%, more particularly by at least 75%, even more particularly by at least 80%, but especially by at least 85%-90%, or more as compared to the respective amyloid peptide monomers incubated in buffer (control), at a molar concentration ratio of antibody to Aβ1-42 of up to 1:1000, particularly at a molar concentration ratio of between 1:10 and 1:100, but especially at a molar concentration ratio of 1:10.

In a specific embodiment of the invention, the antibody, particularly the humanized antibody according to the invention including any functionally equivalent antibody or functional parts thereof inhibits the aggregation of the Aβ monomers and/or Aβ soluble polymers comprising a plurality of said Aβ monomeric units to high molecular polymeric fibrils by at least 30% at a molar concentration ratio of antibody to Aβ1-42 of 1:100.

In another specific embodiment of the invention, the antibody, particularly the humanized antibody according to the invention including any functionally equivalent antibody or functional parts thereof inhibits the aggregation of the Aβ monomers and/or Aβ soluble polymers comprising a plurality of said Aβ monomeric units to high molecular polymeric fibrils by at least 80% at a molar concentration ratio of antibody to Aβ1-42 of 1:10.

Binding of the antibodies according to the invention and as described herein to amyloidogenic monomeric and/or polymeric peptides but, particularly, to the amyloid form (1-42) leads to inhibition of the aggregation of monomeric and/or polymeric amyloidogenic peptides to high molecular fibrils or filaments. Through the inhibition of the aggregation of amyloidogenic monomeric and/or polymeric peptides the antibodies according to the present invention are capable of preventing or slowing down the formation of amyloid plaques, particularly the amyloid form (1-42), which is know to become insoluble by change of secondary conformation and to be the major part of amyloid plaques in brains of diseased animals or humans.

The aggregation inhibition potential of the antibody according to the invention may be determined by any suitable method known in the art, particularly by density-gradient ultracentrifugation followed by a SDS-PAGE sedimentation analysis on a preformed gradient and/or by a thioflavin T (Th-T) fluorescent assay.

In one embodiment, the invention relates to an antibody, particularly a humanized antibody as described herein including any functionally equivalent antibody or functional parts thereof, which antibody, upon co-incubation, particularly at a molar concentration ratio of between 1:5 and 1:1000, particularly of between 1:10 and 1:500, more particularly at a ratio of 1:10 to 1:300, even more particularly at a ratio of between 1:10 and 1:100, with preformed high molecular polymeric amyloid fibrils or filaments formed by the aggregation of Aβ monomeric peptides having at least 30, particularly at least 35, more particularly at least 38, even more particularly at least 40 amino acid residues and, but especially $A\beta_{1-42}$ monomeric peptides, is capable of disaggregating the preformed polymeric fibrils or filaments by at least 20%, particularly by at least 30%, more particularly by at least 35%, even more particularly by at least 40%, but especially by at least 50% or more.

In a specific embodiment of the invention, the aggregation inhibition and the disaggregation potential of the antibody, respectively, is determined by density-gradient ultracentrifugation followed by a SDS-PAGE sedimentation analysis on a preformed gradient.

In another specific embodiment of the invention, the aggregation inhibition and the disaggregation potential of the antibody, respectively, is determined by thioflavin T (Th-T) fluorescent assay.

In another specific embodiment, the antibody according to the invention is co-incubated with amyloid preformed high molecular polymeric amyloid fibrils or filaments for 12 hours to 36 hours, particularly for 18 hours to 30 hours, more particularly for 24 hours at a temperature of between 28° C. and 40° C., particularly of between 32° C. and 38° C., more particularly at 37° C.

In particular, the co-incubation with preformed high molecular polymeric amyloid fibrils or filaments is done for 24 hours at a temperature of 37° C.

In a specific embodiment of the invention, the antibody, particularly the humanized antibody according to the invention including any functionally equivalent antibody or functional parts thereof is capable of disaggregating the preformed polymeric fibrils or filaments by at least 24% at a molar concentration ratio of antibody to Aβ1-42 of 1:100.

In another specific embodiment of the invention, the antibody, particularly the humanized antibody according to the invention including any functionally equivalent antibody or functional parts thereof is capable of disaggregating the preformed polymeric fibrils or filaments by at least 32% at a molar concentration ratio of antibody to Aβ1-42 of 1:10.

Through the disaggregation of amyloidogenic polymeric fibrils or filaments the antibodies according to the present invention are capable of preventing or slowing down the formation of amyloid plaques which leads to an alleviation of the symptoms associated with the disease and a delay or reversal of its progression.

Accordingly, it is a further embodiment of the invention to provide an antibody, particularly a humanized antibody, including any functionally equivalent antibody or functional parts thereof as described herein, which antibody is capable of decreasing the total amount of Aβ in the brain of an animal, particularly a mammal, but especially a human suffering from a disease or condition leading to increased concentration of Aβ in the brain.

In another embodiment, the invention relates to a humanized antibody according to the invention and as described herein before, which antibody is bi-effective in that it exhibits both an aggregation inhibition property as well as a disaggregation property, particularly paired with a high degree of conformational sensitivity.

In particular, the invention relates to a chimeric antibody or a fragment thereof, or a humanized antibody or a fragment thereof according to the invention and as described herein before, which antibody, upon co-incubation with amyloid monomeric and/or polymeric soluble amyloid peptides, particularly with β-amyloid monomeric peptides such as, for example, Aβ monomeric peptides 1-39; 1-40, 1-41, or 1-42, and/or a polymeric soluble β-amyloid peptide comprising a plurality of said Aβ monomeric units, but especially with an $A\beta_{1-42}$ monomeric and/or an Aβ polymeric soluble amyloid peptide comprising a plurality of said $A\beta_{1-42}$ monomeric units, inhibits the aggregation of the Aβ monomers into high molecular polymeric fibrils or filaments and, in addition, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, or 1-42, but especially $A\beta_{1-42}$ monomeric peptides, is capable of disaggregating the pre-formed polymeric fibrils or filaments.

In another aspect, the invention relates to a chimeric antibody or a fragment thereof, or a humanized antibody or a fragment thereof according to the present invention and as described herein before, which antibody is capable of inducing a transition of the β-sheet conformation towards an α-helix and/or a random coil conformation, but particularly a random coil conformation, even more particularly a random coil conformation at a given location in the molecule, especially in the environment of Tyr 10 and Val 12 of the Aβ protein, which leads to an increase of the random coil conformation at the expense of the β-sheet conformation and an improved solubilization of the preformed high molecular polymeric amyloid fibrils or filaments. In particular the decrease of the β-sheet conformation amounts to at least 30%, particularly to at least 35%, and more particularly to at least 40% and more as compared to the respective preformed amyloid polymeric fibrils or filaments incubated in buffer (control).

The antibody's potential in inducing a transition in the secondary structure is determined by solid state 13C NMR spectroscopy but, in particular, by measuring the integral intensities of the conformations of Tyr 10 and Val 12 Cβ in the $A\beta_{1-42}$ peptide.

In a further embodiment of the invention, a chimeric antibody or a fragment thereof, or a humanized antibody or a fragment thereof according to the present invention and as described herein before, is provided comprising at least one light chain or a fragment thereof or at least one heavy chain or a fragment thereof, wherein said antibody or fragment binds to an Aβ monomer with a high binding affinity with a $K_D$ in a range of between at least about $1\times10^{-7}$ M to at least about $1\times10^{-12}$ M, particularly of at least about $1\times10^{-8}$ M to at least about $1\times10^{-11}$ M, more particularly of at least about $1\times10^{-9}$ M to at least about $1\times10^{-10}$ M, even more particularly of at least about $1\times10^{-8}$ M to at least about $2\times10^{-8}$ M but, preferably, does not show any significant cross-reactivity with amyloid precursor protein (APP).

In another embodiment of the invention, a chimeric antibody or a fragment thereof, or a humanized antibody or a fragment thereof according to the present invention and as described herein before, is provided comprising at least one light chain or a fragment thereof or at least one heavy chain or a fragment thereof, wherein said antibody or fragment binds to an Aβ fiber, fibril or filament with a high binding affinity with a $K_D$ in a range of between at least about $1\times10^{-7}$ M to at least about $1\times10^{-12}$M, particularly of at least about $1\times10^{-8}$ M to at least about $1\times10^{-11}$ M, more particularly of at least about $1\times10^{-9}$ M to at least about $1\times10^{-10}$ M, even more particularly of at least about $2\times10^{-9}$ M to at least about $5\times10^{-9}$ M, but, preferably, does not show any significant cross-reactivity with amyloid precursor protein (APP).

In another embodiment, the antibody according to the invention and as described herein before or a fragment thereof, exhibits an binding affinity to an Aβ fiber, fibril or filament which is at least 2 times, particularly at least 4 times, particularly at least 10 times, particularly at least 15 times, more particularly at least 20 times, but especially at least 25 times higher than the binding affinity to an Aβ monomer.

In still another embodiment, a chimeric antibody or a fragment thereof, or a humanized antibody or a fragment thereof is provided as described herein before, which antibody substantially binds to aggregated Aβ, including Aβ plaques, in the mammalian, particularly the human brain but, preferably, does not show any significant cross-reactivity with amyloid precursor protein (APP).

In another aspect of the invention, the chimeric antibody or a fragment thereof, or a humanized antibody or a fragment thereof is provided as described herein before, which antibody substantially binds to soluble polymeric amyloid, particularly amyloid β(Aβ), including Aβ monomers, in the mammalian, particularly the human brain but, preferably, does not show any significant cross-reactivity with amyloid precursor protein (APP).

Further provided is a chimeric antibody or a fragment thereof, or a humanized antibody or a fragment thereof according to the invention and as described herein before, which antibody significantly reduces Aβ plaque burden in the mammalian, particularly the human brain. This can be achieved by either binding of the antibody to the plaque or by shifting the equilibrium between amyloid, particularly amyloid β(Aβ), in its insoluble and aggregated state towards its soluble form by disaggregating fibers to soluble poly- and monomeric forms by inducing a shift in conformation and binding and stabilizing the disaggregated and solubilized amyloid forms, particularly amyloid β(Aβ) forms, in the tissue and/or body fluids, particularly the brain. Through the activity of the antibody according to the invention the peripheral clearing and catabolism is thus favored rather than deposition within the tissue and/or body fluids, particularly the brain. The beneficial effect of the antibody according to the invention can thus be obtained without binding of the antibody to the plaque.

Through this stabilizing activity, the antibody according to the invention is able to neutralize the toxic effects of the polymeric and less aggregated soluble amyloid protein, particularly amyloid β(Aβ) protein, in the tissue and/or body fluids. In a specific embodiment of the invention the antibody according to the invention may thus achieve its beneficial effects without necessarily binding aggregated amyloid beta in the brain.

In a further aspect of the invention a humanized antibody or a fragment thereof according to the present invention and as described herein before, is provided comprising at least one light chain or a fragment thereof or at least one heavy chain or a fragment thereof incorporating at least one, particularly two and more particularly three CDR regions obtained form a mouse donor antibody, particularly from mouse antibody ACI-01-Ab7C2 (named "mC2" and hC2 for the humanized C2 antibody, throughout the application) deposited 1 Dec. 2005 with the "Deutsche Sammlung von Mikroorganismen und Zellkulturen GmbH (DSMZ) in Braunschweig, Mascheroder Weg 1 B, 38124 Braunschweig, under accession no DSM ACC2750, wherein said antibody or fragment thereof has an affinity to the Aβ antigen which is at least 5 times, particularly at least 8 times, more particularly at least 10 times, but especially at least 15 times higher than that of the mouse donor antibody.

The antibody of this invention can be, in one embodiment, a whole antibody (e.g., with two full length light chains and two full length heavy chains) of any isotype and subtype (e.g., IgM, IgD, IgG1, IgG2, IgG3, IgG4, IgE, IgA1 and IgA2); but especially an antibody of the IgG4 isotype; alternatively, in another embodiment, it can be an antigen-binding fragment (e.g., Fab, F(ab')$_2$, and Fv) of a whole antibody.

The invention thus also relates to antigen-binding fragments of the antibodies described herein. In one embodiment of the invention, the fragment is selected from the group consisting of a Fab fragment, a Fab' fragment, a F(ab)$_2$ fragment, and a F$_v$ fragment, including the products of an Fab immunoglobulin expression library and epitope-binding fragments of any of the antibodies and fragments mentioned above.

In another embodiment, the antibody or antigen-binding fragment of the invention is conjugated to polyethylene glycol. In yet another embodiment, the constant region of the antibody of the invention is modified to reduce at least one constant region-mediated biological effector function relative to an unmodified antibody. In still another embodiment, the antibody or antigen-binding fragment of the invention comprises a Fc region having an altered effector function.

The invention further relates to a nucleotide molecule comprising a nucleotide sequence encoding a chimeric antibody or a fragment thereof, or a humanized antibody or a fragment thereof according to the invention and as disclosed herein before.

In particular, the invention relates to a nucleotide molecule comprising a nucleotide sequence encoding a stretch of contiguous amino acid molecules as given in SEQ ID NO: 2 and 3, respectively, or the complementary sequence, representing the Complementarity Determining Regions (CDRs) 2 and 3 of the Heavy Chain Variable Region (HCVR).

More particularly, the invention relates to a nucleotide molecule comprising a nucleotide sequence encoding a stretch of contiguous amino acid molecules as given in SEQ ID NO: 4, or the complementary sequence, representing the Complementarity Determining Regions (CDRs) 1 of the Light Chain Variable Region (LCVR).

In another embodiment of the invention a nucleotide molecule is provided comprising a nucleotide sequence as given in SEQ ID NO: 18 and SEQ ID NO: 19, or the complementary sequence, encoding the amino acid sequence of CDR 2 and CDR 3, respectively, of the Heavy Chain Variable Region (HCVR).

In another embodiment of the invention a nucleotide molecule is provided comprising a nucleotide sequence as given in SEQ ID NO: 20, or the complementary sequence, encoding the nucleotide sequence of CDR 1 of the Light Chain Variable Region (LCVR).

In another embodiment of the invention a nucleotide molecule is provided comprising a nucleotide sequence of SEQ ID NO: 21, or the complementary sequence, encoding the light chain variable region.

In another embodiment of the invention a nucleotide molecule is provided comprising a nucleotide sequence of SEQ ID NO: 22, or the complementary sequence, encoding the complete light chain variable region including signal sequences.

In another embodiment of the invention a nucleotide molecule is provided comprising a nucleotide sequence encoding the light chain variable region of SEQ ID NO: 22 and the light chain constant region of SEQ ID NO: 23. The invention also comprises the complementary strand of said nucleotide molecule.

In another embodiment of the invention a nucleotide molecule is provided comprising a nucleotide sequence of SEQ ID NO: 24 encoding the heavy chain variable region. The invention also comprises the complementary strand of said nucleotide molecule.

In another embodiment of the invention a nucleotide molecule is provided comprising a nucleotide sequence of SEQ ID NO: 25 encoding the complete heavy chain variable region including signal sequences. The invention also comprises the complementary strand of said nucleotide molecule.

In another embodiment of the invention a nucleotide molecule is provided comprising a nucleotide sequence encoding the heavy chain variable region of SEQ ID NO: 25 and the heavy chain constant region of SEQ ID NO: 26. The invention also comprises the complementary strand of said nucleotide molecule.

Also comprised by the present invention is a nucleotide sequence which hybridizes to one of the above-described antibody-encoding nucleotide sequences of the invention, particularly to the complementary strand thereof, either in isolation or as part of larger nucleotide molecule.

In particular, the invention relates to a nucleotide sequence that hybridizes under conventional hybridization conditions, particularly under stringent hybridization conditions, to any of the nucleotide sequences given in SEQ ID NOs: 18-26 and 29-32, particularly to the complementary strand thereof.

In another embodiment of the invention an expression vector is provided comprising the nucleic acid molecule according to the invention and as mentioned herein before.

In another embodiment of the invention a cell is provided comprising an expression vector comprising the nucleic acid according to the invention and as mentioned herein before.

In still another embodiment, the invention relates to a composition comprising the antibody according to the invention, but particularly a chimeric antibody or a fragment thereof, or a humanized antibody or a fragment thereof according to the invention and as described herein before including any functionally equivalent antibody or any derivative or functional parts thereof, in a therapeutically effective amount, in particular a composition which is a pharmaceutical composition optionally further comprising a pharmaceutically acceptable carrier.

In another embodiment of the invention, said composition comprises the antibody in a therapeutically effective amount.

Further comprised by the invention is a mixture comprising an antibody, particularly a monoclonal antibody according to the invention, but particularly a chimeric antibody or a fragment thereof, or a humanized antibody or a fragment thereof according to the invention and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the invention relates to a mixture, wherein the further biologically active substance is a compound used in the medication of amyloidosis, a group of diseases and disorders associated with amyloid or amyloid-like protein such as the Aβ protein involved in Alzheimer's disease.

In another embodiment of the invention, the other biologically active substance or compound may also be a therapeutic agent that may be used in the treatment of amyloidosis caused by amyloid β or may be used in the medication of other neurological disorders.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

More particularly, the invention relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements, and nutritive supplements, together with an antibody according to the present invention and, optionally, a pharmaceutically acceptable carrier and/or a diluent and/or an excipient.

The invention further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the invention may comprise niacin or memantine together with an antibody according to the present invention and, optionally, a pharmaceutically acceptable carrier and/or a diluent and/or an excipient.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the invention, but particularly a chimeric antibody or a fragment thereof, or a humanized antibody or a fragment thereof according to the invention and as described herein and, optionally, a pharmaceutically acceptable carrier and/or a diluent and/or an excipient.

In a specific embodiment of the invention, the compositions and mixtures according to the invention and as described herein before comprise the antibody and the biologically active substance, respectively, in a therapeutically effective amount.

Other compounds that can be suitably used in mixtures in combination with the antibody according to the present invention are described in WO 2004/058258 (see especially pages 16 and 17) including therapeutic drug targets (page 36-39), alkanesulfonic acids and alkanolsulfuric acids (pages 39-51), cholinesterase inhibitors (pages 51-56), NMDA receptor antagonists (pages 56-58), estrogens (pages 58-59), non-steroidal anti-inflammatory drugs (pages 60-61), anti-oxidants (pages 61-62), peroxisome proliferators-activated receptor (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference.

In another embodiment, the invention relates to a mixture comprising the antibody, particularly a monoclonal antibody according to the invention, but particularly a chimeric antibody or a fragment thereof, or a humanized antibody or a fragment thereof according to the invention and as described herein before and/or the biologically active substance in a therapeutically effective amount.

The invention further relates to the use of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody, for the preparation of a medicament for treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Also comprised by the present invention is a method for the preparation of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody and/or a functional part thereof, particularly in a therapeutically effective amount, for use in a method of preventing, treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration comprising formulating an antibody, particularly a monoclonal antibody according to the invention, but particularly a chimeric antibody or a fragment thereof, or a humanized antibody or a fragment thereof according to the invention in a pharmaceutically acceptable form.

Further comprised by the present invention is a method for preventing, treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration by administering an antibody and/or a functional part thereof, but particularly a humanized antibody and/or a functional part thereof, or a composition or mixture comprising such an antibody and/or a functional part thereof, to a an animal or a human affected by such a disorder comprising administering the antibody in a therapeutically effective amount.

It is also an object of the invention to provide a method for the treatment of amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity by administering to an animal, particularly a mammal or a human, an antibody, particularly a pharmaceutical composition according to the invention and as described herein.

In a specific embodiment the invention provides a method for retaining or increasing cognitive memory capacity but, particularly, for restoring the cognitive memory capacity of an animal, particularly a mammal or a human, suffering from memory impairment by administering to an animal, particularly a mammal or a human, an antibody, particularly a pharmaceutical composition according to the invention and as described herein before.

It is a further object of the invention to provide a therapeutic composition and a method of producing such a composition as well as a method for the treatment of amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity, using an antibody according to the invention and as described herein before.

In particular, the invention relates to the treatment of an animal, particularly a mammal or a human, suffering from an amyloid-associated condition characterized by a loss of cognitive memory capacity leads to the retention of cognitive memory capacity.

The invention further relates to a method of diagnosis of an amyloid-associated disease or condition in a patient comprising detecting the immunospecific binding of an antibody or an active fragment thereof to an epitope of the amyloid protein in a sample or in situ which includes the steps of (a) bringing the sample or a specific body part or body area suspected to contain the amyloid protein into contact with an antibody, particularly a monoclonal antibody according to the invention, but particularly a chimeric antibody or a fragment thereof, or a humanized antibody or a fragment thereof according to the invention and as described herein before, and/or a functional part thereof, which antibody binds an epitope of the amyloid protein;

(b) allowing the antibody and/or a functional part thereof, to bind to the amyloid protein to form an immunological complex;

(c) detecting the formation of the immunological complex; and (d) correlating the presence or absence of the immunological complex with the presence or absence of amyloid protein in the sample or specific body part or area.

Also comprised is a method of determining the extent of amyloidogenic plaque burden in a tissue and/or body fluids comprising (a) obtaining a sample representative of the tissue and/or body fluids under investigation;

(b) testing said sample for the presence of amyloid protein with an antibody, particularly a monoclonal antibody according to the invention, but particularly a chimeric antibody or a fragment thereof, or a humanized antibody or a fragment thereof according to the invention and as described herein before, and/or a functional part thereof;

(c) determining the amount of antibody bound to the protein; and (d) calculating the plaque burden in the tissue and/or body fluids.

In particular, the invention relates to a method of determining the extent of amyloidogenic plaque burden in a tissue and/or body fluids, wherein the formation of the immunological complex in step c) is determined such that presence or absence of the immunological complex correlates with presence or absence of amyloid protein.

In another embodiment of the invention, a test kit for detection and diagnosis of amyloid-associated diseases and conditions is provided comprising an antibody, particularly a monoclonal antibody according to the invention, but particularly a chimeric antibody or a fragment thereof, or a humanized antibody or a fragment thereof according to the invention and as described herein before, and/or a functional part thereof.

In particular, the invention relates to a test kit for detection and diagnosis of amyloid-associated diseases and conditions comprising a container holding one or more antibodies according to the present invention, and/or a functional part thereof, and instructions for using the antibodies for the purpose of binding to amyloid protein to form an immunological complex and detecting the formation of the immunological complex such that presence or absence of the immunological complex correlates with presence or absence of amyloid protein.

In another aspect, the invention provides an antibody comprising a variable region as recited in SEQ ID NO: 27, or a variant thereof. In one embodiment, a cell line expressing the antibody.

In another aspect, the invention provides an antibody gene comprising a variable region as recited in SEQ ID NO: 29, or a variant thereof. In one embodiment, a cell line expresses the antibody.

In another aspect, the invention provides a method for disaggregating preformed beta-amyloid fibers, comprising interacting an hC2 antibody with preformed beta-amyloid fibers.

In another aspect, the invention provides a humanized antibody or a fragment thereof according to any of the preceding claims, wherein said antibody or fragment thereof protects neurons from Abeta-induced degradation.

In another aspect, the invention provides a method of preventing Abeta-induced neuron degradation comprising treating neurons with an effective amount of a humanized antibody or a fragment thereof according to the disclosure herein.

In another aspect, the invention provides use of a humanized antibody or a fragment thereof according to the description herein for the preparation of a medicament for preventing degeneration of neurons upon exposure to Abeta oligomer.

These and other objects, features and advantages of the present invention will become apparent after a review of the following detailed description of the disclosed embodiment and the appended claims.

BRIEF DESCRIPTION OF FIGURES AND SEQUENCES

FIG. 1 (Example 2): Expression Cassette of the mouse light chain variable region of the Chimeric Antibody (SEQ ID NOS 58 & 59)

FIG. 2 (Example 2): Expression Cassette of the mouse heavy chain variable region of the Chimeric Antibody (SEQ ID NOS 60 & 61)

Figures 3, 13:
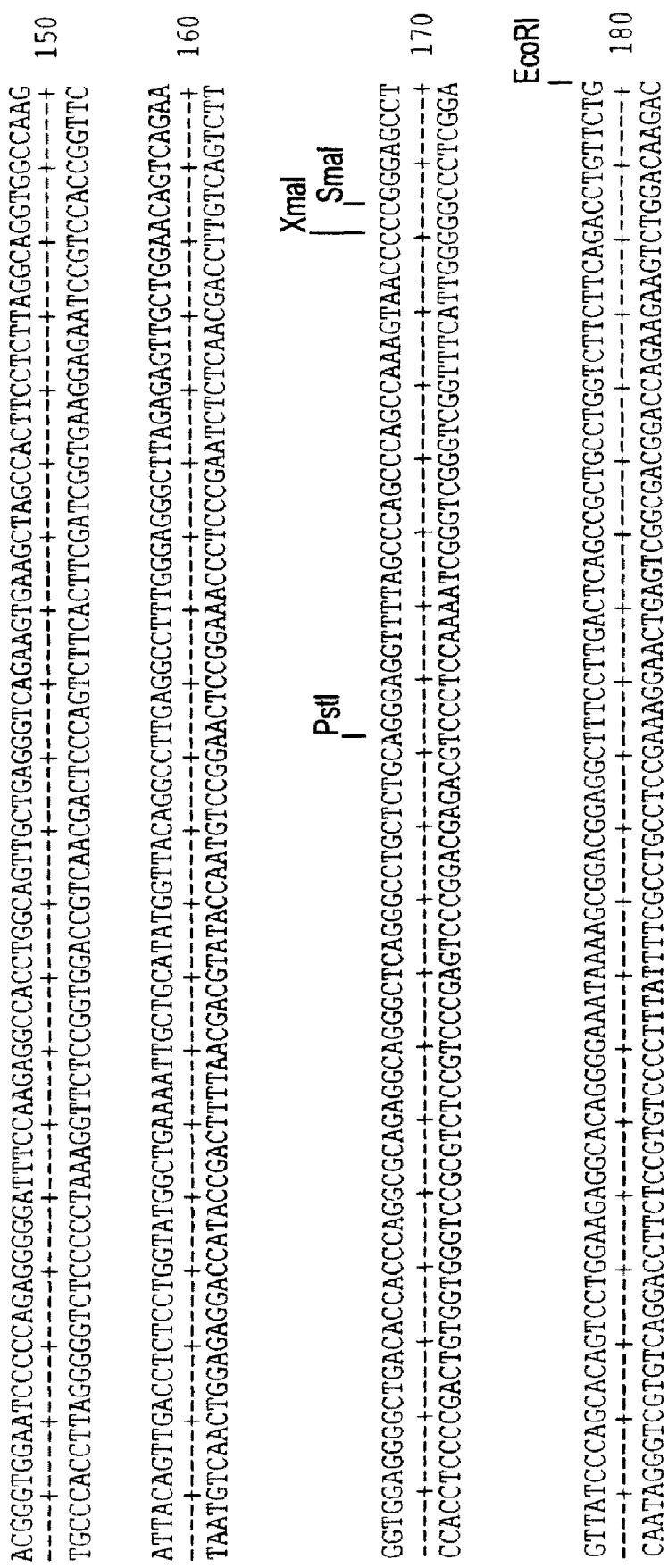
Figures 4, 13:

FIG. 3 (Example 5.2): Comparison of the mouse heavy chain variable region to the closest murine germ line sequence (SEQ ID NOS 28 & 62)

Figure 4:
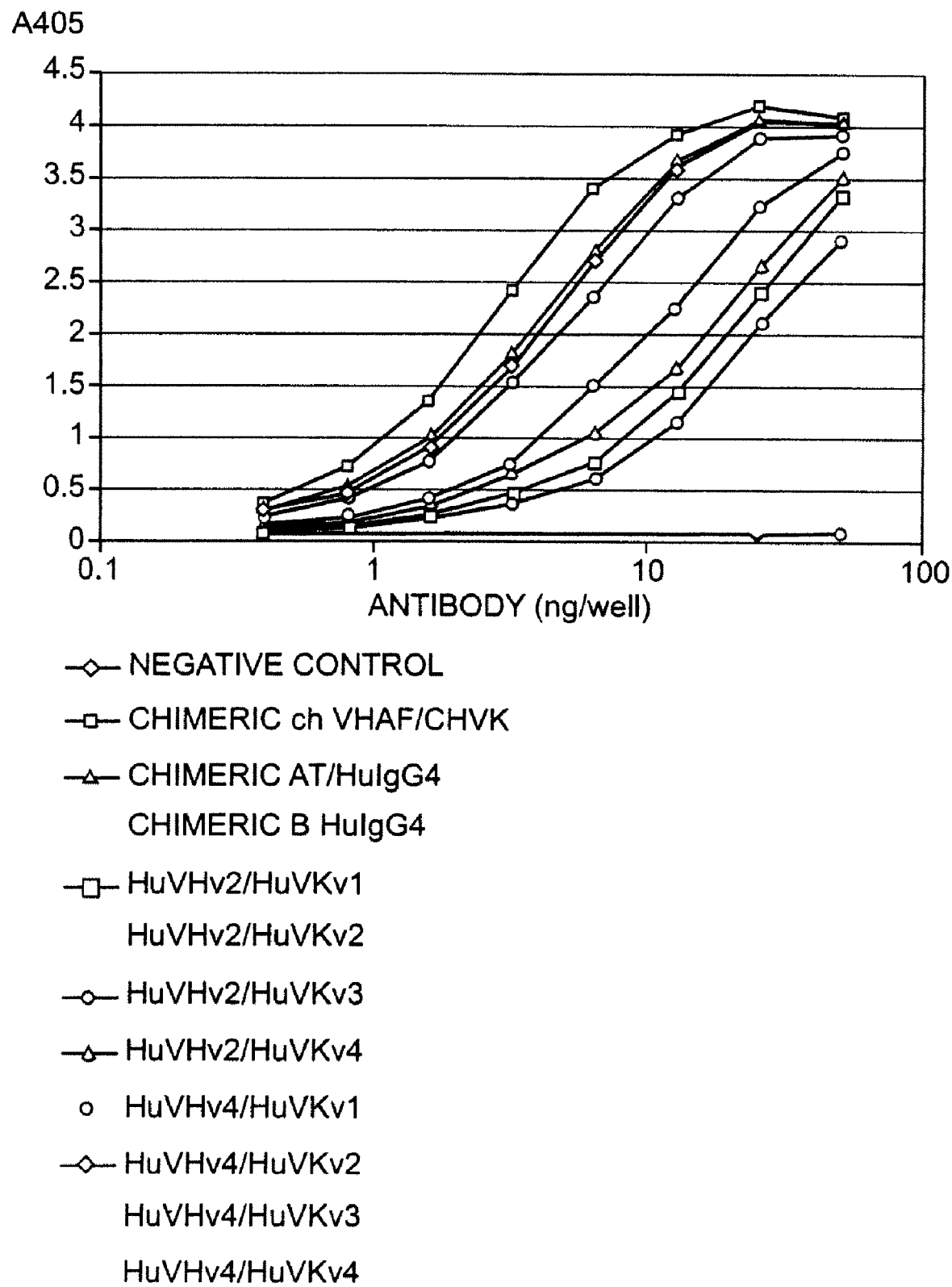

FIG. 4 (Example 8): Activity of purified humanized C2 antibodies

Figure 5:
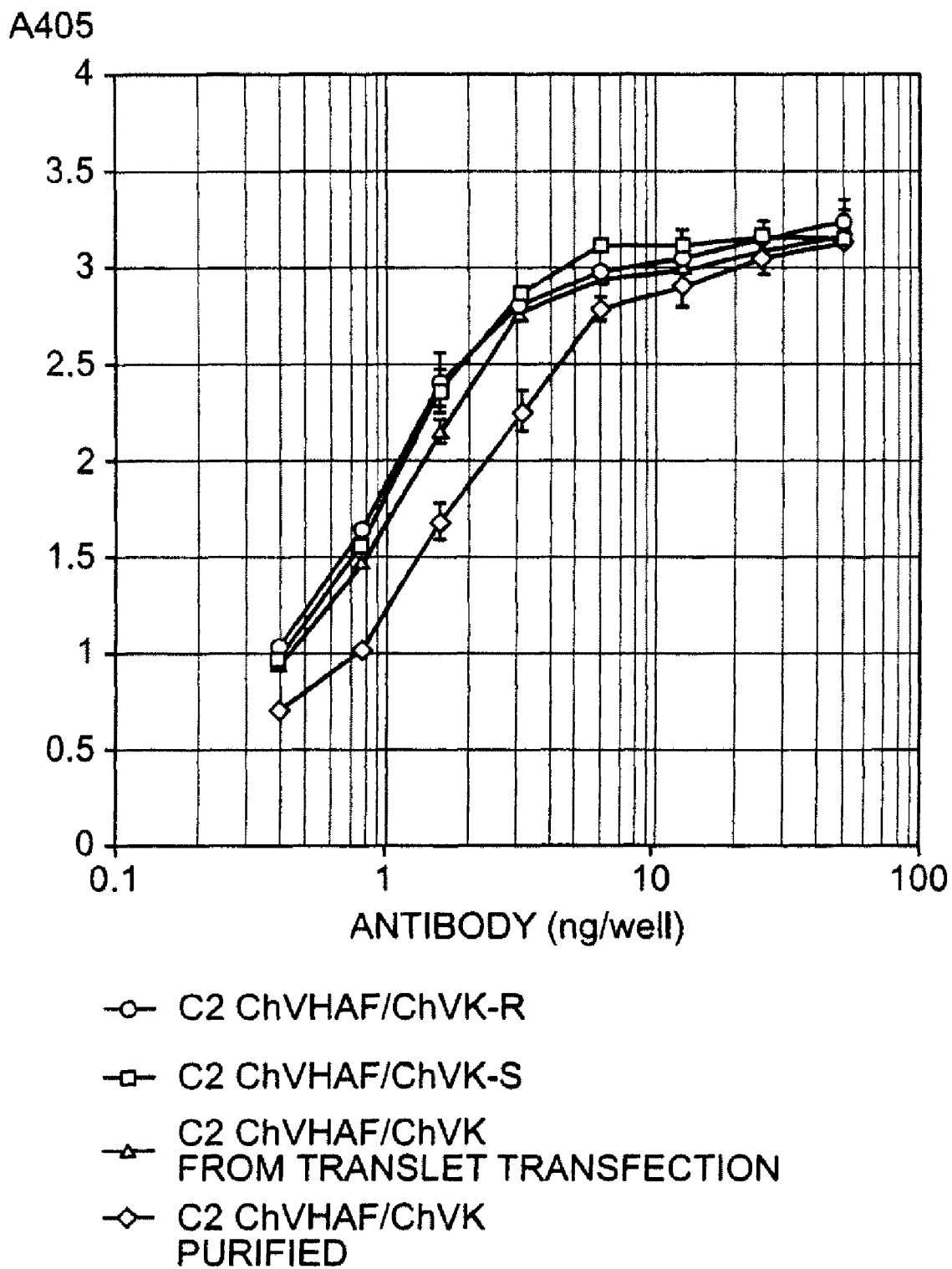

FIG. 5 (Example 9): Binding activity of antibodies produced by transient expression of C2 modified CDRL2 constructs in conjunction with C2 chimeric heavy chain, compared to chimeric antibody C2ChVHAF/ChVK, produced by transient transfection and purified antibody.

Figure 6:
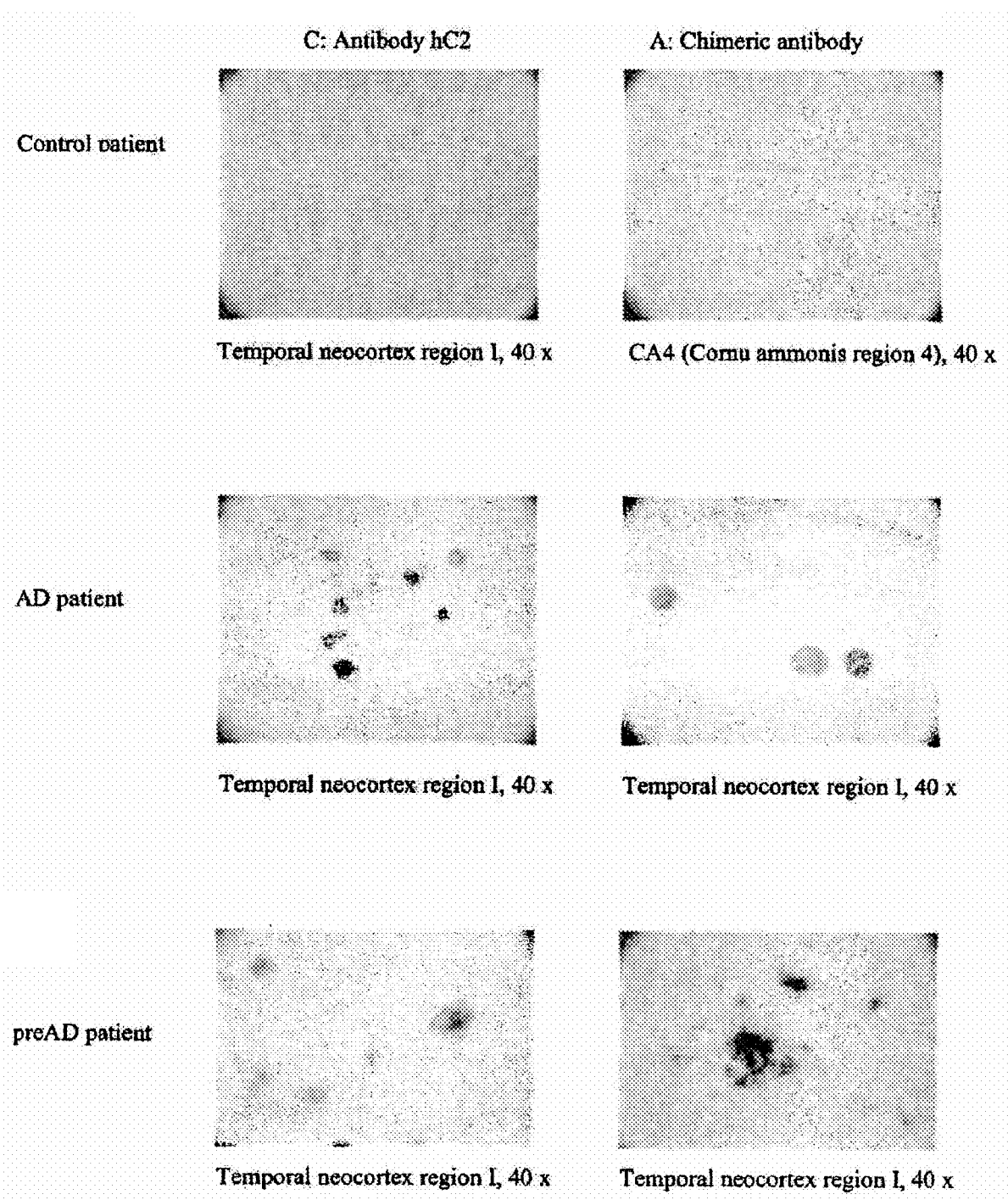

FIG. 6 (Example 11): Results of Immunohistochemical Binding Assay with chimeric antibody AF and humanized antibody H4K1.

Figures 7A, 7B:
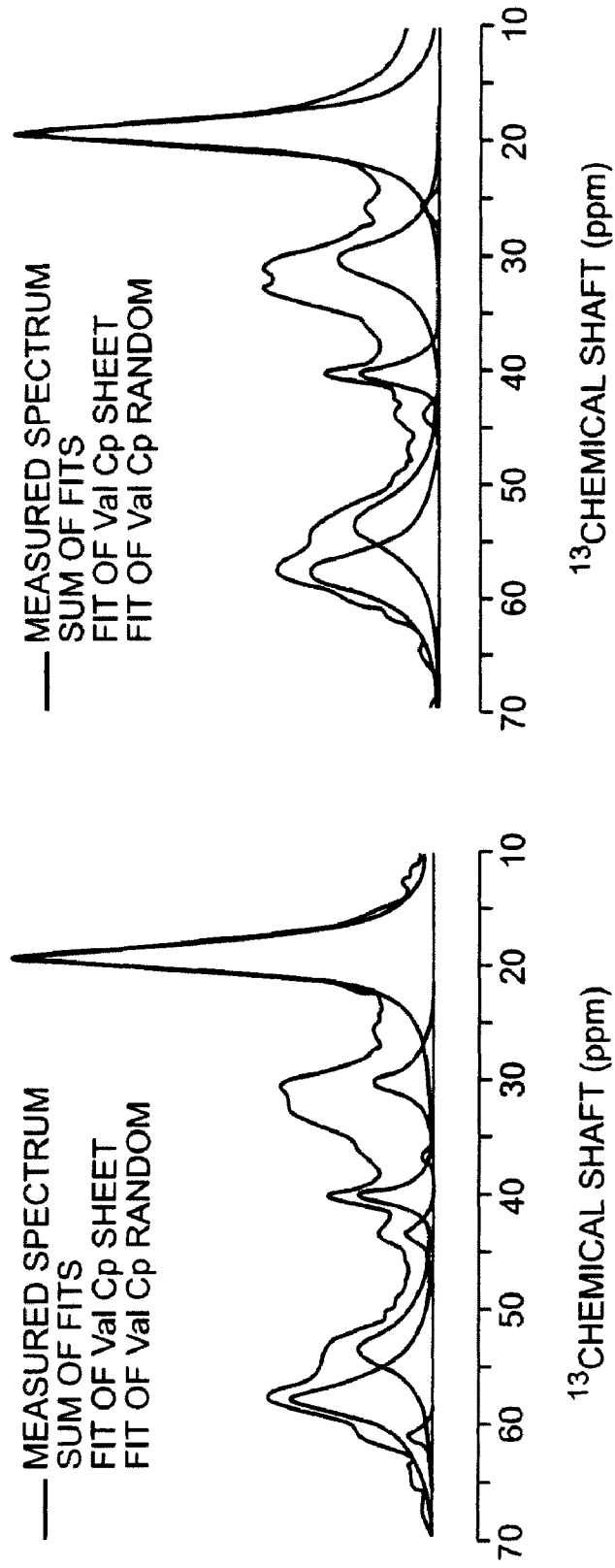

FIG. 7A-B (Example 12): Functionality of mC2 on Amyloid fibers. FIG. 7A is the comparison of $^{13}$C CPMAS spectra and fits for U-$^{13}$C Tyr10 and Val12 lableled amyloid β 1-42 fibres incubated with PBS (left; served as control) or AC1-7 C2 (right) for 24 hrs and then lyophilized. The fits for the two conformations of Val12 Cβ are shown in sheet and random coil. The peak at c33 ppm corresponds to the beta sheet conformation of the fibres whilst that at 30 ppm is a result of random coil conformation. FIG. 7B is the comparison of the fitted parameters for the two conformations of Val12 Cβ. The fitted chemical shifts for the two conformations are quite similar but the integral intensities are very different, reflecting a reduction in the original beta sheet conformation by approx 35% (1−(53.5/81.7)). This is in very close agreement with the value we obtained from the fluorescence measurement.

Figure 8:
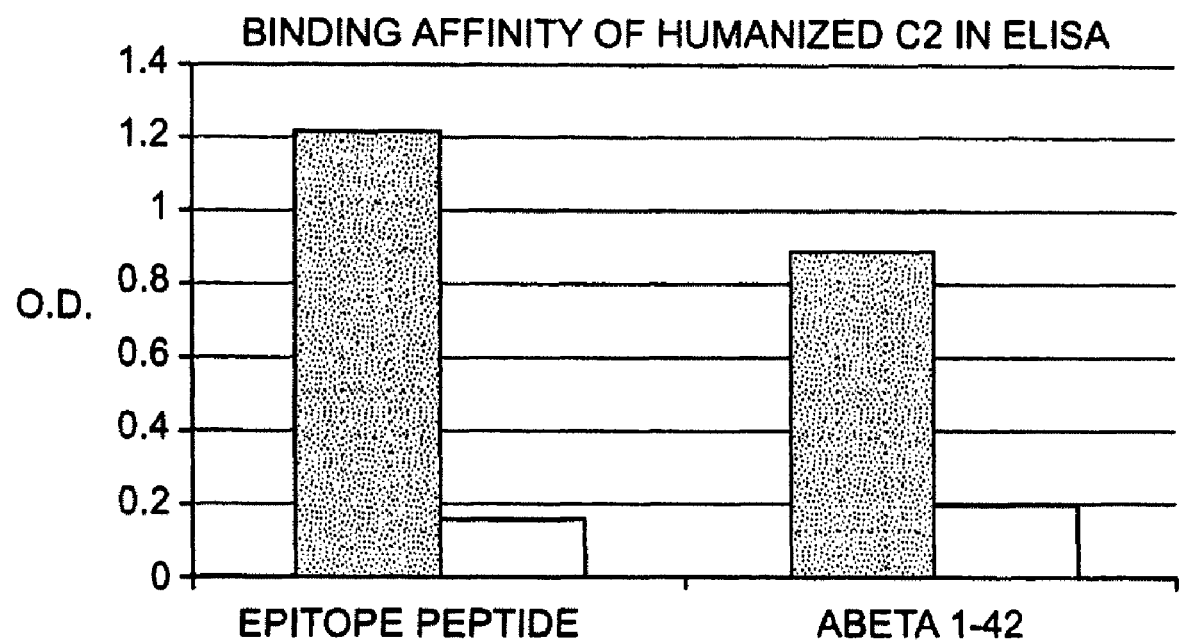

FIG. 8 (Example 12): Binding Affinity of humanized C2 in ELISA.

Figure 9:
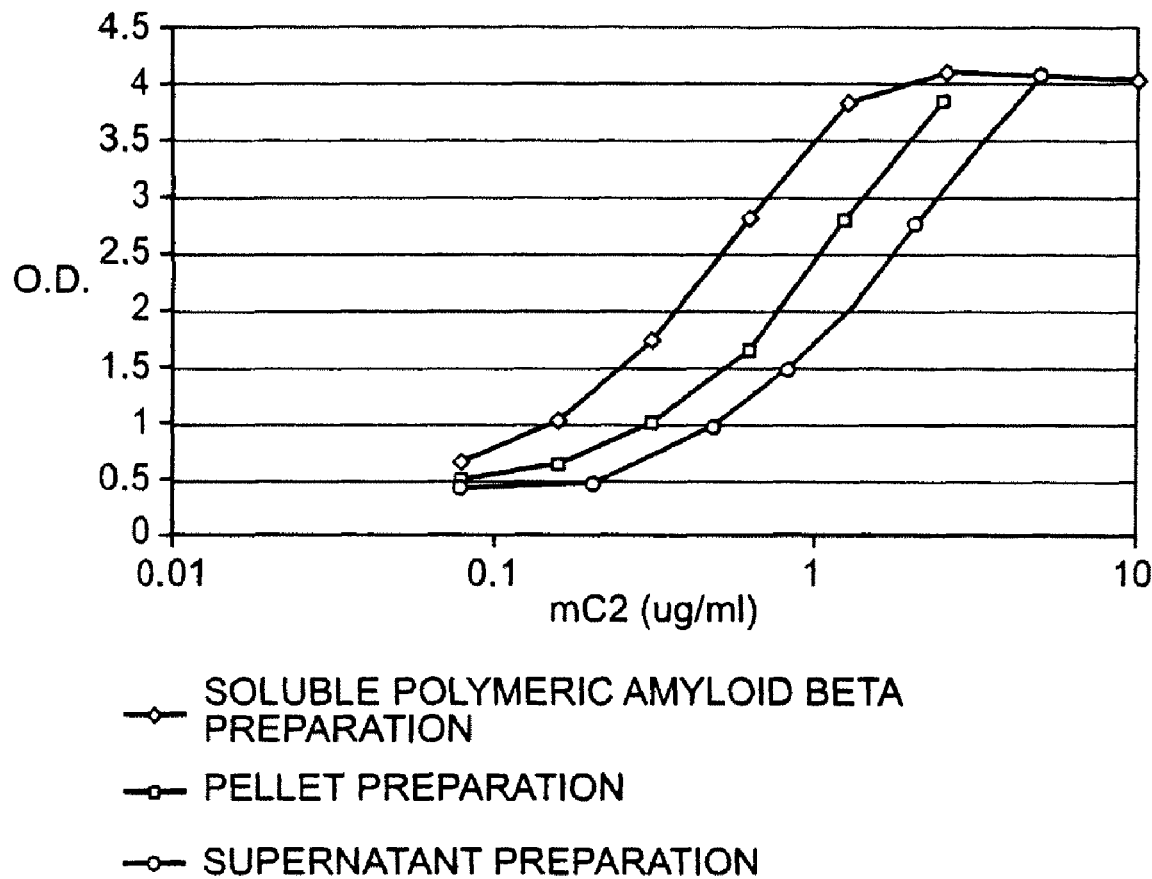

FIG. 9 (Example 14): Conformation specific binding of mC2 to different classes of amyloid protein. Pellet preparation in the legend to this figure refers to $A\beta_{1-42}$ fibers, supernatant preparation refers to amyloid monomers.

FIG. 10: Humanized C2 VK sequences compared to murine sequence and human acceptor sequences DPK15 AND $J_K1$ (SEQ ID NOS 27, 12 & 63-67 respectively in order of appearance)

FIG. 11: Humanized C2 VH sequences compared to murine sequence and human acceptor sequences DP54 AND $J_H6$ (SEQ ID NOS 68-71, 15 & 72-73 respectively in order of appearance)

Figures 1, 12:
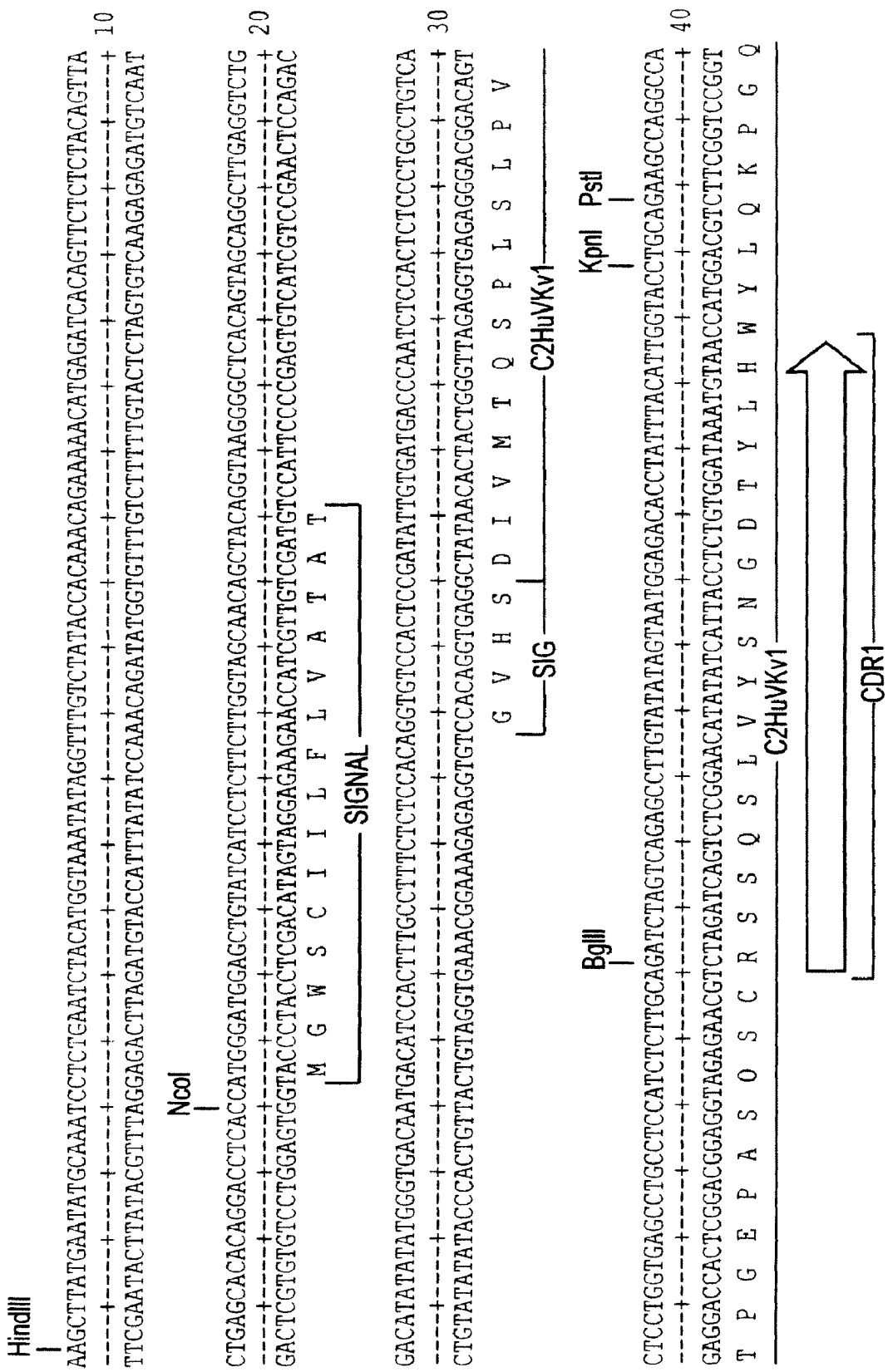
Figures 2, 12:
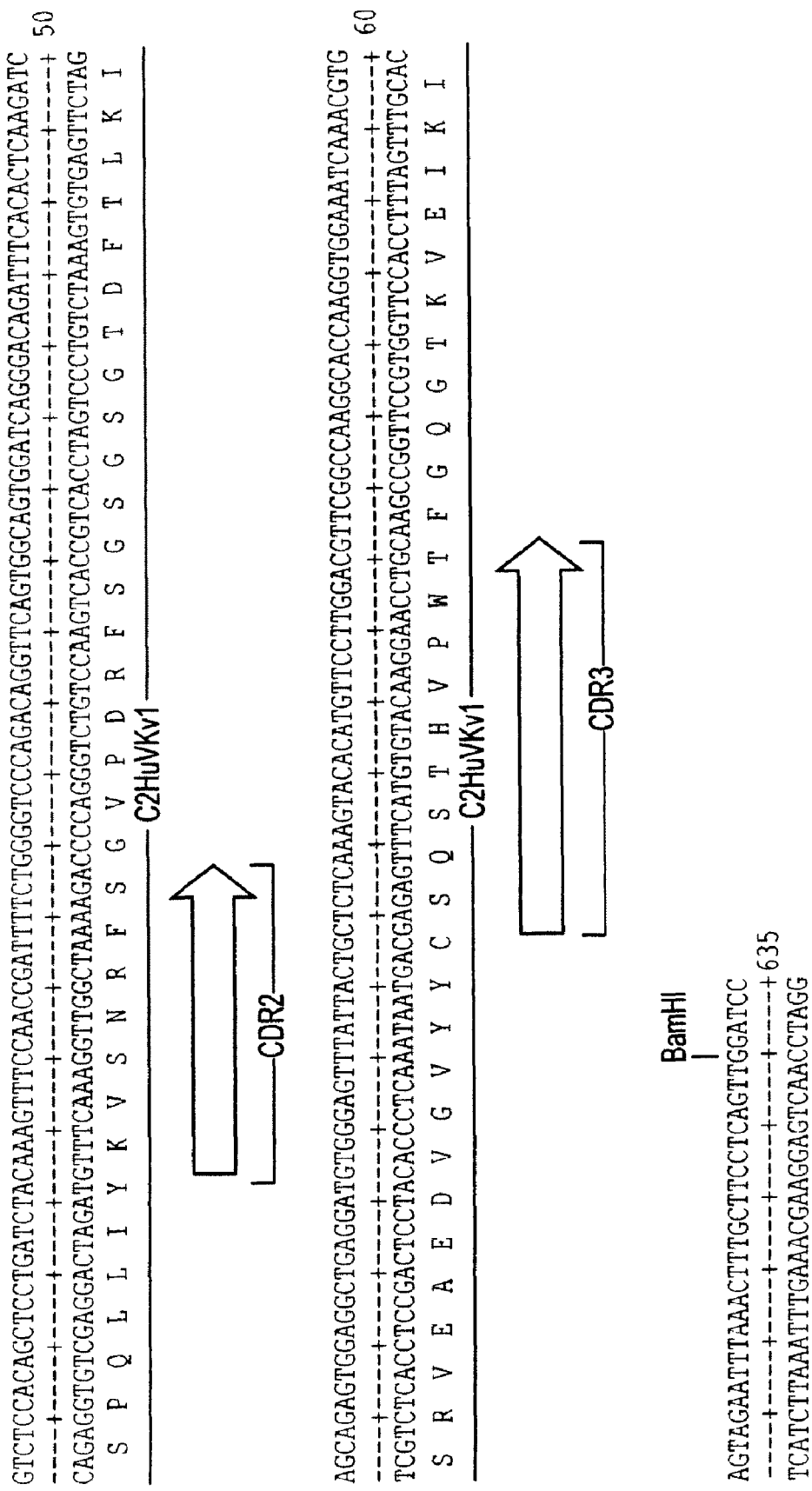

FIG. 12: Complete DNA and protein sequence of light chain variable region of C2 humanized antibody, C2HuVK1 (SEQ ID NOS 74 & 75)

FIG. 13: Complete DNA and protein sequence of light chain constant region (human C Kappa) of humanized C2 antibody (SEQ ID NOS 76 & 77)

Figures 4, 14:
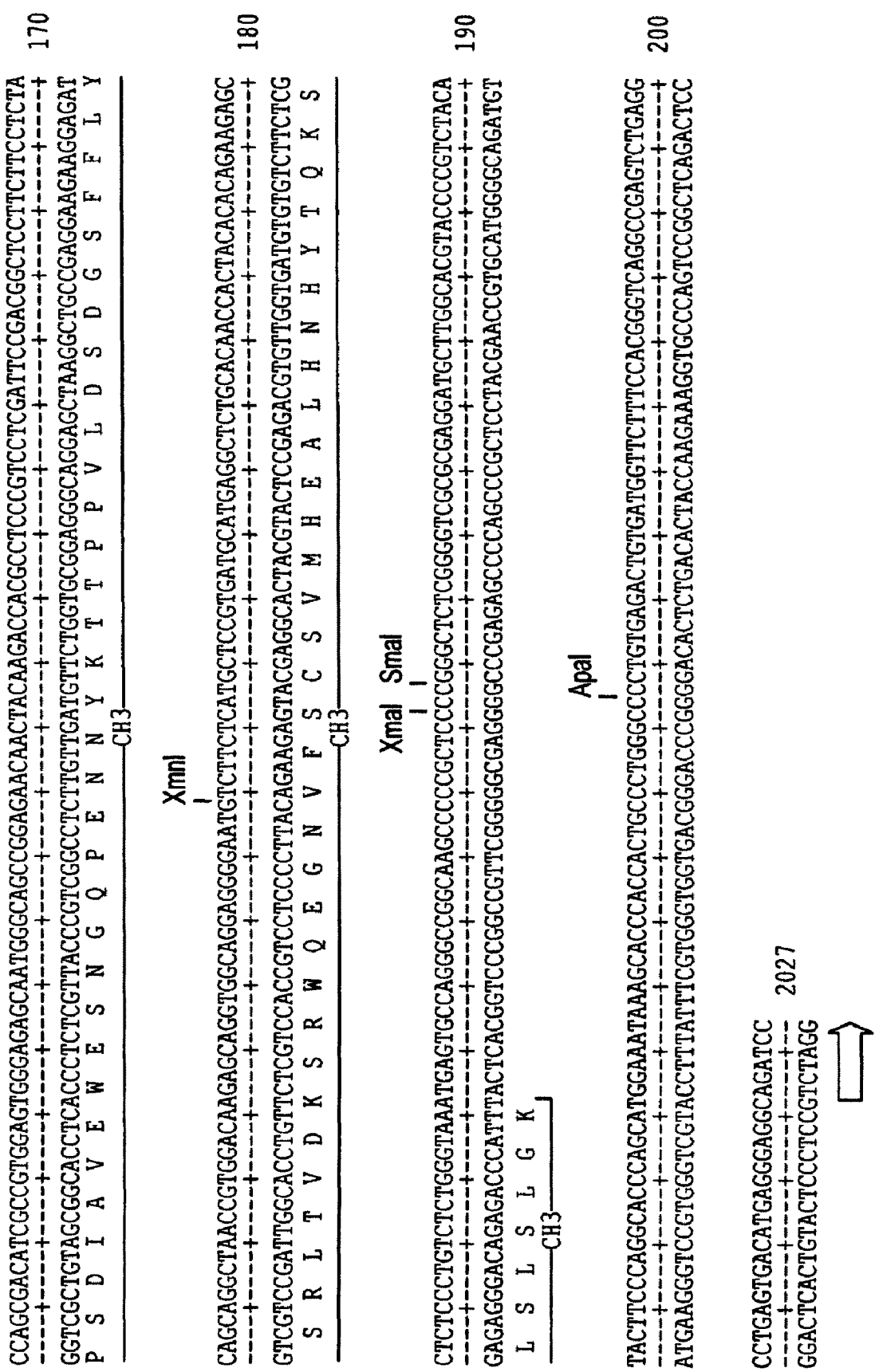

FIG. 14: Complete DNA and protein sequence of heavy chain constant region (human IgG4 ser228-pro) of humanized C2 antibody (SEQ ID NOS 78 & 79)

Figure 15A:
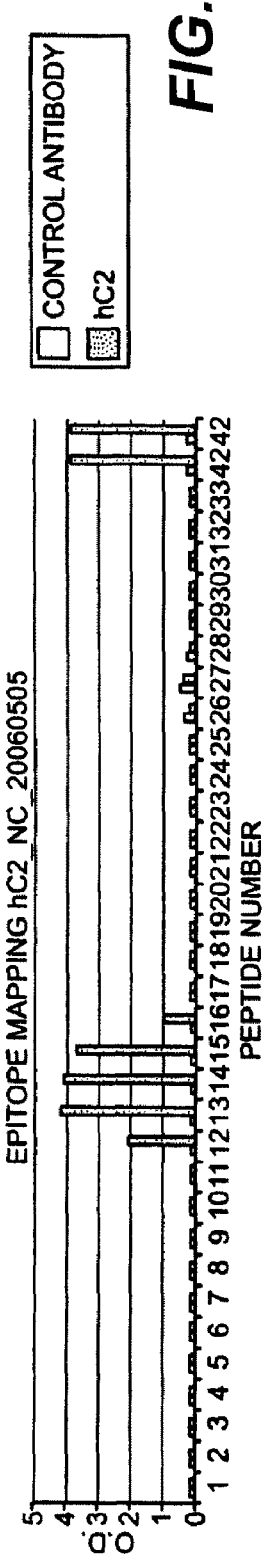
Figure 15B:
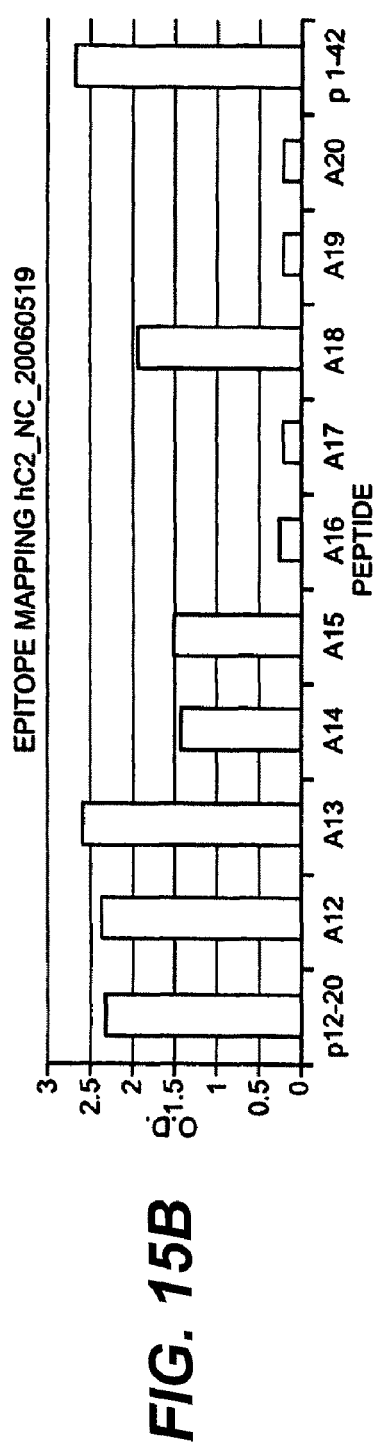
Figure 15C:
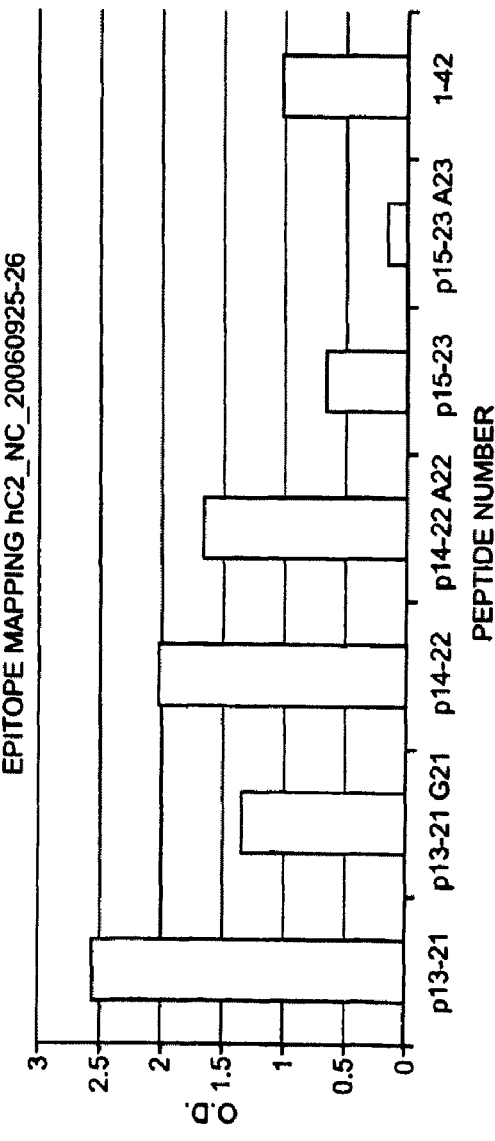

FIG. 15A-C (Example 15): Results of Epitope Mapping experiments. FIG. 15A: hC2 binds to peptides 12, 13, 14, 15 and 16 of the $A\beta1$-42 peptide library. Binding of hC2 to overlapping peptides of $A\beta1$-42 was analyzed by ELISA. Binding to the complete $A\beta1$-42 and binding of a non-binding chimeric antibody (control antibody) was used as positive and negative controls respectively. The peptide number corresponds to the amino acid in the $A\beta1$-42 sequence on which the peptide starts. Results are expressed as O.D. FIG. 15B: hC2 binding to is $A\beta12$-20 completely dependent on amino acids 16, 17, 19 and 20 and partially dependent on amino acids 14, 15 and 18. Binding of hC2 to $A\beta12$-20 and alanine substituted $A\beta12$-20 was analyzed by ELISA. Binding to the complete $A\beta1$-42 was used as positive control. The number corresponds to the amino acid that is substituted by alanine. Results are expressed as O.D. FIG. 15C: hC2 binding to $A\beta15$-23 as dependent on amino acid 23 and partially on amino acid 21 and slightly dependent on amino acid 22. Binding of hC2 to $A\beta13$-21, 14-22 or 15-23 and to 13-21G21, 14-22A22 or 15-23A23 was analyzed by ELISA. Binding to the complete $A\beta1$-42 was used as positive control. Results are expressed as O.D.

Figure 16:
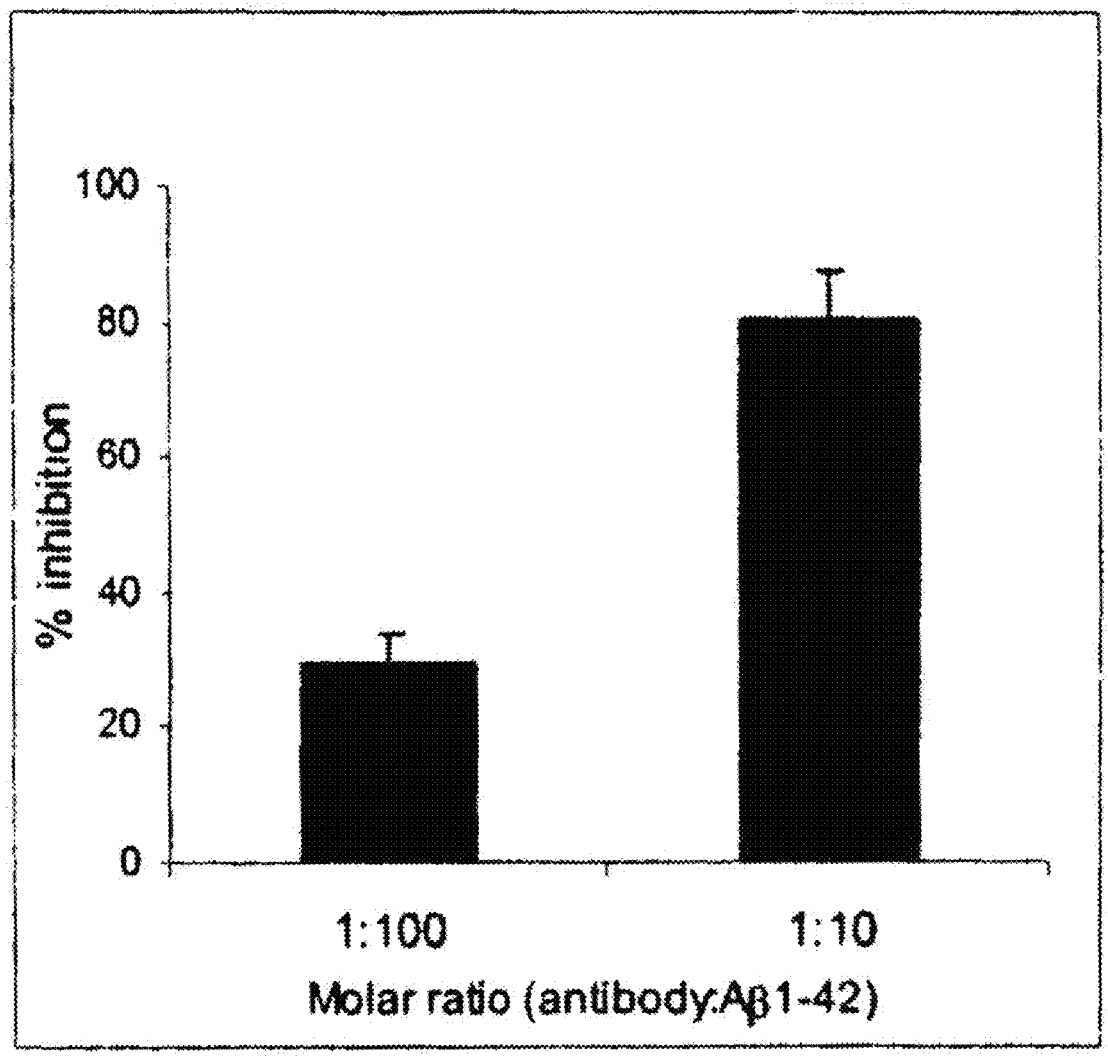

FIG. 16 (Example 13): Results of aggregation assay experiments

Figure 17:
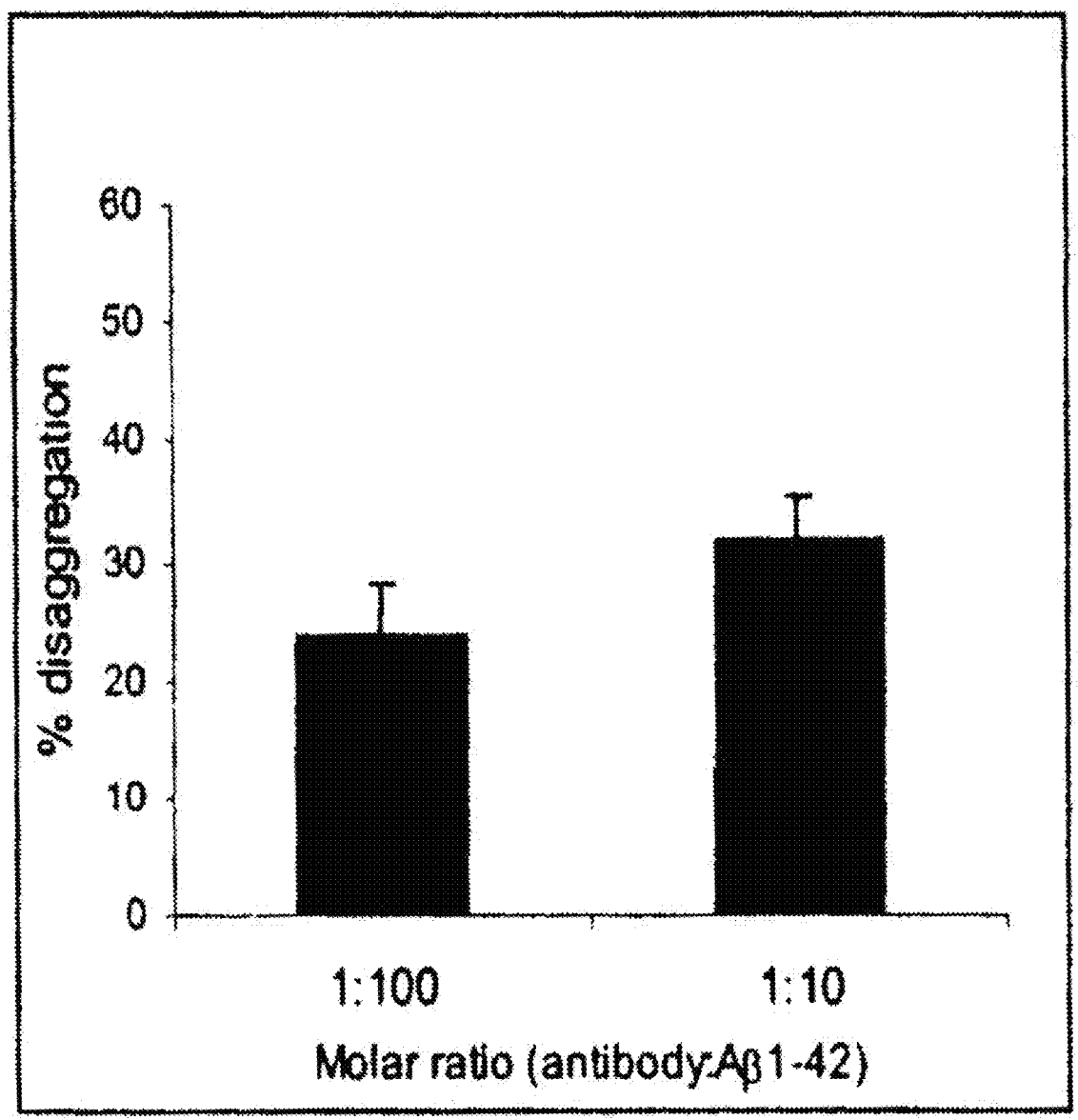

FIG. 17 (Example 13): Results of disaggregation assay experiments

Figure 18:
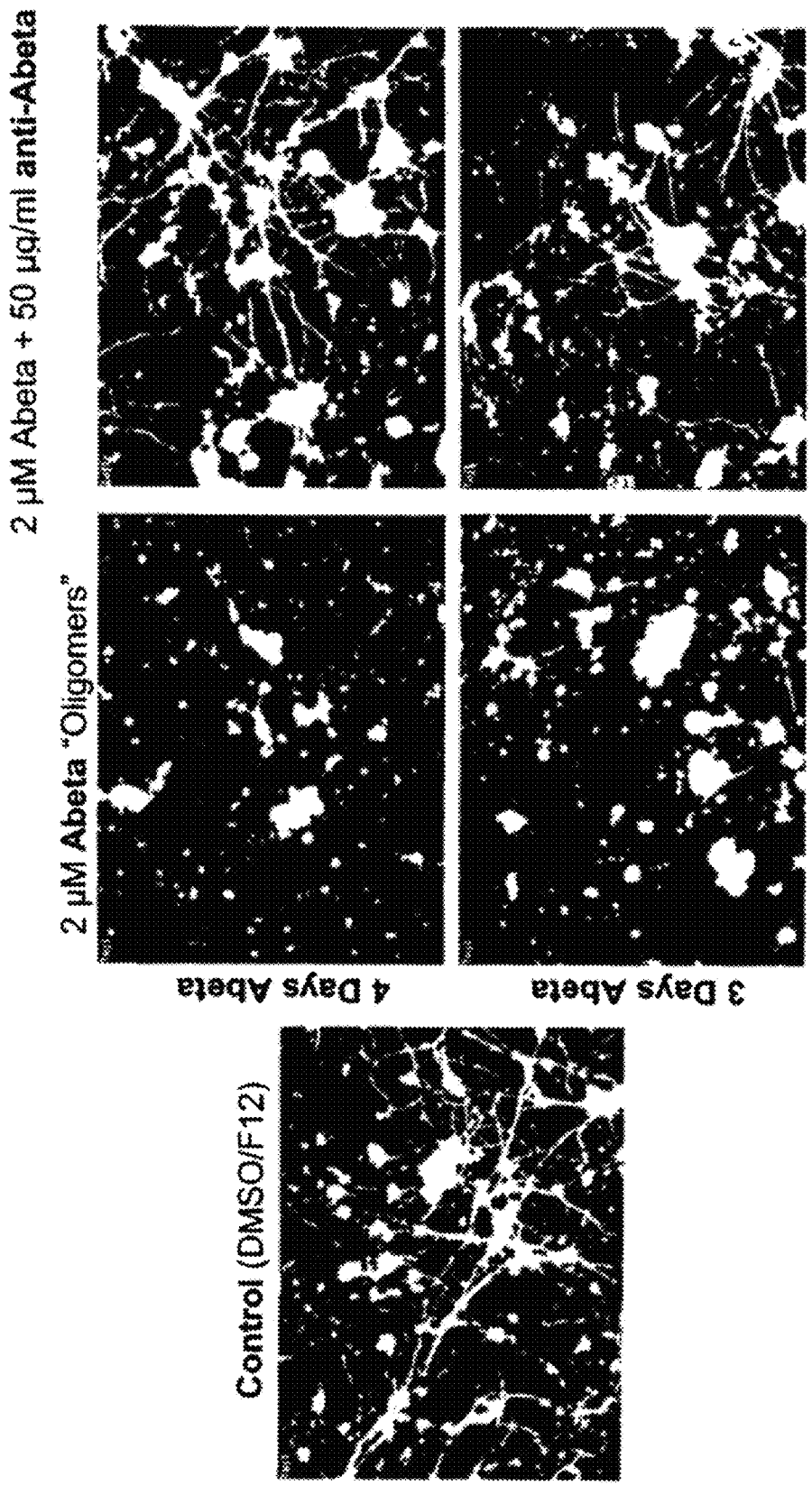

FIG. 18: (Example 16): Results of neuroprotection experiments with humanized antibody C2.

SEQ ID NO: 1 Amino acid sequence of C2 HuVH AF 4 humanized heavy chain variable region (CDR1)

SEQ ID NO: 2 Amino acid sequence of C2 HuVH AF 4 humanized heavy chain variable region (CDR2)

SEQ ID NO: 3 Amino acid sequence of C2 HuVH AF 4 humanized heavy chain variable region (CDR3)

SEQ ID NO: 4 Amino acid sequence of C2 HuVK 1 humanized light chain variable region (CDR1)

SEQ ID NO: 5 Amino acid sequence of C2 HuVK 1 humanized light chain variable region (CDR2)

SEQ ID NO: 6 Amino acid sequence of C2 HuVK 1 humanized light chain variable region (CDR3)

SEQ ID NO: 7 Amino acid sequence of Aβ epitope region 2

SEQ ID NO: 8 Amino acid sequence of Aβ epitope region 1

SEQ ID NO: 9 Amino acid sequence of Aβ epitope region 2 modified

SEQ ID NO: 10 Amino acid sequence of Aβ epitope region 1 modified

SEQ ID NO: 11 Amino acid sequence of Epitope region modified complete

SEQ ID NO: 12 Amino acid sequence of C2 HuVK 1 humanized light chain variable region SEQ ID NO: 13 Amino acid sequence of C2 humanized light chain SEQ ID NO: 14 Amino acid sequence of humanized C2 light chain constant region SEQ ID NO: 15 Amino acid sequence of C2 HuVH AF 4 humanized heavy chain variable region SEQ ID NO: 16 Amino acid sequence of C2 humanized heavy chain SEQ ID NO: 17: Amino acid sequence of IG GAMMA-4 CHAIN C REGION-modified SEQ ID NO: 18: Nucleotide sequence of CDR2 of C2 HuVH AF 4 humanised heavy chain variable region SEQ ID NO: 19: Nucleotide sequence of CDR3 of C2 HuVH AF 4 humanised heavy chain variable region SEQ ID NO: 20: Nucleotide sequence of CDR1 of C2 HuVK 1 humanised light chain variable region SEQ ID NO: 21: Nucleotide sequence of C2 HuVK 1 humanized light chain variable region SEQ ID NO: 22: Nucleotide sequence of C2 humanized light chain SEQ ID NO: 23: Nucleotide sequence of C2 humanized light chain constant region SEQ ID NO: 24: Nucleotide sequence of C2 HuVH AF 4 humanized heavy chain variable region SEQ ID NO: 25: Nucleotide sequence of C2 humanized heavy chain SEQ ID NO: 26: Nucleotide sequence of C2 humanized heavy chain constant region SEQ ID NO: 27: Amino acid sequence of Mouse C2 Light Chain Variable Region SEQ ID NO: 28: Amino acid sequence of Mouse C2 Heavy Chain Variable Region SEQ ID NO: 29: Nucleotide sequence of Mouse C2 Light Chain Variable Region SEQ ID NO: 30: Nucleotide sequence of Mouse C2 Light Chain SEQ ID NO: 31: Nucleotide sequence of Mouse C2 Heavy Chain Variable Region SEQ ID NO: 32: Nucleotide sequence of Mouse C2 Heavy Chain

DEFINITIONS

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes, and senile cardiac amyloidosis; and various eye diseases including macular degeneration, drusen-related optic neuropathy, and cataract due to beta-amyloid deposition.

The terms "detecting" or "detected" as used herein mean using known techniques for detection of biologic molecules such as immunochemical or histological methods and refer to qualitatively or quantitatively determining the presence or concentration of the biomolecule under investigation.

"Polymeric soluble amyloid" refers to multiple aggregated monomers of amyloid peptides, or of amyloid-like peptides, or of modified or truncated amyloid peptides or of other derivates of amyloid peptides forming oligomeric or polymeric structures which are soluble in the mammalian or human body more particularly in the brain, but particularly to multiple aggregated monomers of amyloid β(Aβ) or of modified or truncated amyloid β(Aβ) peptides or of derivatives thereof, which are soluble in the mammalian or human body more particularly in the brain.

"Amyloid β, Aβ or β-amyloid" is an art recognized term and refers to amyloid β proteins and peptides, amyloid β precursor protein (APP), as well as modifications, fragments and any functional equivalents thereof. In particular, by amyloid β as used herein is meant any fragment produced by proteolytic cleavage of APP but especially those fragments which are involved in or associated with the amyloid pathologies including, but not limited to, $A\beta_{1-38}$, $A\beta_{1-39}$, $A\beta_{1-40}$, $A\beta_{1-41}$ $A\beta_{1-42}$ and $A\beta_{1-43}$.

The structure and sequences of the amyloid β peptides as mentioned above are well known to those skilled in the art and methods of producing said peptides or of extracting them from brain and other tissues are described, for example, in Glenner and Wong, Biochem Biophys Res Comm 129, 885-890 (1984). Moreover, amyloid β peptides are also commercially available in various forms.

By "isolated" is meant a biological molecule free from at least some of the components with which it naturally occurs.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecules, i.e molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to $V_H$-$CH_1$ by a disulfide bond. The F(ab')$_2$ may be reduced under mild conditions to break the disulfide linkage in the hinge region thereby converting the F(ab')$_2$ dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include monoclonal antibodies, polyclonal antibodies, chimeric, single chain, bispecific, simianized, human and humanized antibodies as well as active fragments thereof. Examples of active fragments of molecules that bind to known antigens include separated light and heavy chains, Fab, Fab/c, Fv, Fab', and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Recombinantly made antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. For example, antibody CDRs may be identified as the hypervariable regions originally defined by Kabat et al. (see, "Sequences of Proteins of Immunological Interest," E. Kabat et al., U.S. Department of Health and Human Services; Johnson, G and Wu, T T (2001) Kabat Database and its applications: future directions. Nucleic Acids Research, 29: 205-206; http://immuno.bme.nwa.edu). The positions of the CDRs may also be identified as the structural loop structures originally described by Chothia and others, (see Chothia and Lesk, J. Mol. Biol. 196, 901 (1987), Chothia et al., Nature 342, 877 (1989), and Tramontano et al., J. Mol. Biol. 215, 175 (1990)). Other methods include the "AbM definition" which is a compromise between Kabat and Chothia and is derived using Oxford Molecular's AbM antibody modeling software (now Accelrys) or the "contact definition" of CDRs by Macallum et al., ("Antibody-antigen interactions: contact analysis and binding site topography," J Mol. Biol. 1996 Oct. 11; 262(5):732-45). The following chart identifies CDRs based upon various known definitions.

| Loop | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B | H26--H35B | H26--H32 . . . 34 | H30--H35B (Kabat Numbering) |
| H1 | H31--H35 | H26--H35 | H26--H32 | H30--H35 (Chothia Numbering) |
| H2 | H50--H65 | H50--H58 | H52--H56 | H47--H58 |
| H3 | H95--H102 | H95--H102 | H95--H102 | H93--H101 |

General guidelines by which one may identify the CDRs in an antibody from sequence alone are as follows:
LCDR1:
Start—Approximately residue 24.
Residue before is always a Cys.
Residue after is always a Trp. Typically TRP is followed with TYR-GLN, but also may be followed by LEU-GLN, PHE-GLN, or TYR-LEU.
Length is 10 to 17 residues.
LCDR2:
Start—16 residues after the end of L1.
Sequence before is generally ILE-TYR, but also may be VAL-TYR, ILE-LYS, or ILE-PHE.
Length is generally 7 residues.
LCDR3:
Start—generally 33 residues after end of L2.
Residue before is a Cys.
Sequence after is PHE-GLY-X-GLY.
Length is 7 to 11 residues.
HCDR1:
Start—at approximately residue 26 (four residues after a CYS) [Chothia/AbM definition] Kabat definition starts 5 residues later.
Sequence before is CYS-X-X-X.
Residues after is a TRP, typically followed by VAL, but also followed by ILE, or ALA.
Length is 10 to 12 residues under AbM definition while Chothia definition excludes the last 4 residues.
HCDR2:
Start—15 residues after the end of Kabat/AbM definition of CDR-H1.
Sequence before typically LEU-GLU-TRP-ILE-GLY (SEQ ID NO. 1), but a number of variations are possible.
Sequence after is LYS/ARG-LEU/ILE/VAL/PHE/THR/ALA-THR/SER/ILE/ALA Length is 16 to 19 residues under Kabat definition (AbM definition ends 7 residues earlier).
HCDR3:
Start—33 residues after end of CDR-H2 (two residues after a CYS).
Sequence before is CYS-X-X (typically CYS-ALA-ARG).
Sequence after is TRP-GLY-X-GLY.
Length is 3 to 25 residues.

The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al., (1988) Nature, 332; 323-327.

Chimeric antibodies are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al., Proc. Natl. Acad. Sci. USA (1998) 95:8910-8915), molecular modeling strategies (U.S. Pat. No. 5,639,641), and the like.

A "humanized antibody" as used herein in the case of a two chain antibody is one where at least one chain is humanized.

A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity.

The humanized antibody may further comprise constant regions (e.g., at least one constant region or portion thereof, in the case of a light chain, and preferably three constant regions in the case of a heavy chain). The constant regions of a humanized antibody if present generally are human.

Methods to obtain "humanized antibodies" are well known to those skilled in the art. (see, e.g., Queen et al., Proc. Natl. Acad Sci USA, 86:10029-10032 (1989), Hodgson et al., Bio/Technology, 9:421 (1991)).

A "humanized antibody" may also be obtained by a novel genetic engineering approach that enables production of affinity-matured human-like polyclonal antibodies in large animals such as, for example, rabbits and mice. See, e.g. U.S. Pat. No. 6,632,976.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably of the kappa type. In one embodiment the light chain constant region is the human kappa constant chain (Heiter et al. (1980) Cell 22:197-207) and the heavy constant chain is the human IgG4 constant chain.

The term "monoclonal antibody" is also well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

For the purpose of the present invention, "monoclonal antibody" is also to be understood to comprise antibodies that are produced by a mother clone which has not yet reached full monoclonality.

"Functionally equivalent antibody" is understood within the scope of the present invention to refer to an antibody which substantially shares at least one major functional property with an antibody mentioned above and herein described comprising: binding specificity to the β-amyloid protein, particularly to the $A\beta_{1-42}$ protein, and more particularly to the 16-21 epitope region of the $A\beta_{1-42}$ protein, immunoreactivity in vitro, inhibition of aggregation of the $A\beta_{1-42}$ monomers into high molecular polymeric fibrils and/or disaggregation of preformed $A\beta_{1-42}$ polymeric fibrils, and/or a β-sheet breaking property and alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, when administered prophylactically or therapeutically. The antibodies can be of any class such as IgG, IgM, or IgA, etc or any subclass such as IgG1, IgG2a, etc and other subclasses mentioned herein above or known in the art, but particularly of the IgG4 class. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and an Fc region from different species.

The term "hybridize" as used refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution see Sambrook et al. loc. cit.). Stringent hybridization conditions as for instance described in Sambrook et al, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

The antibody according to the invention may be an immunoglobulin or antibody, which is understood to have each of its binding sites identical (if multivalent) or, in the alternative, may be a "bispecific" or "bifunctional antibody".

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments, See, e.g., Songsivilai & Lachmann, *Clin. Exp. Immunol.* 79:315-321 (1990); Kostelny et al., *J. Immunol.* 148, 1547-1553 (1992).

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies.

"Fragment" also refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

The term "antigen" refers to an entity or fragment thereof which can bind to an antibody. An immunogen refers to an antigen which can elicit an immune response in an organism, particularly an animal, more particularly a mammal including a human. The term antigen includes regions known as antigenic determinants or epitopes which refers to a portion of the antigen (which are contacted or which play a significant role in supporting a contact reside in the antigen responsible for antigenicity or antigenic determinants.

As used herein, the term "soluble" means partially or completely dissolved in an aqueous solution.

Also as used herein, the term "immunogenic" refers to substances which elicit the production of antibodies, T-cells and other reactive immune cells directed against an antigen of the immunogen.

An immune response occurs when an individual produces sufficient antibodies, T-cells and other reactive immune cells against administered immunogenic compositions of the present invention to moderate or alleviate the disorder to be treated.

The term immunogenicity as used herein refers to a measure of the ability of an antigen to elicit an immune response (humoral or cellular) when administered to a recipient. The present invention is concerned with approaches that reduce the immunogenicity of the subject human chimeric or humanized antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis. Suitable antigen binding assays are described in this application.

A "back mutation" is a mutation introduced in a nucleotide sequence which encodes a humanized antibody, the mutation results in an amino acid corresponding to an amino acid in the parent antibody (e.g., donor antibody, for example, a murine antibody). Certain framework residues from the parent antibody may be retained during the humanization of the antibodies of the invention in order to substantially retain the binding properties of the parent antibody, while at the same time minimizing the potential immunogenicity of the resultant antibody. In one embodiment of the invention, the parent antibody is of mouse origin. For example, the back mutation changes a human framework residue to a parent murine residue. Examples of framework residues that may be back mutated include, but are not limited to, canonical residues, interface packing residues, unusual parent residues which are close to the binding site, residues in the "Vernier Zone" (which forms a platform on which the CDRs rest) (Foote & Winter, 1992, *J. Mol. Biol.* 224, 487-499), and those close to CDR H3.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. Those of ordinary skill in the art will be able to predict which amino acid substitutions can be made while maintaining a high probability of being conformationally and antigenically neutral. Such guidance is provided, for example in Berzofsky, (1985) *Science* 229:932-940 and Bowie et al. (1990) *Science* 247:1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to microcomplement fixation methods (Wasserman et al. (1961) J. Immunol. 87:290-295; Levine et al. (1967) Meth. Enzymol. 11:928-936) and through binding studies using conformation-dependent monoclonal antibodies (Lewis et al. (1983) Biochem. 22:948-954).

Further, the term "therapeutically effective amount" refers to the amount of antibody which, when administered to a human or animal, which is sufficient to result in a therapeutic effect in said human or animal. The effective amount is readily determined by one of skill in the art following routine procedures.

As used herein, the terms "treat," "prevent," "preventing," and "prevention" refer to the prevention of the recurrence or onset of one or more symptoms of a disorder in a subject resulting from the administration of a prophylactic or therapeutic agent.

Construction of Humanized Antibodies

The present invention may be understood more readily by reference to the following detailed description of specific embodiments included herein. Although the present invention has been described with reference to specific details of certain embodiments, thereof, it is not intended that such details should be regarded as limitations upon the scope of the invention.

The present invention provides novel methods and compositions comprising highly specific and highly effective antibodies having the ability to specifically recognize and bind to specific epitopes from a range of β-amyloid antigens. The antibodies enabled by the teaching of the present invention are particularly useful for the treatment of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), Adult Onset Diabetes; senile cardiac amyloidosis; endocrine tumors, and others, including macular degeneration, to name just a few.

A fully humanized or reshaped variable region according to the present invention may be created within the scope of the invention by first designing a variable region amino acid sequence that contains non-human-, particularly rodent-derived CDRs, but especially CDRs derived from murine antibody ACI-01-Ab7C2 (named "mC2" throughout the application and deposited 1 Dec. 2005 with the "Deutsche Sammlung von Mikroorganismen und Zellkulturen GmbH (DSMZ) in Braunschweig, Mascheroder Weg 1 B, 38124 Branuschweig, under the provisions of the Budapest Treaty and given accession no DSM ACC2750) embedded in human-derived framework sequences. The non-human-, particularly the rodent-derived CDRs, which may be obtained from the antibody according to the present invention, provide the desired specificity. Accordingly, these residues are to be included in the design of the reshaped variable region essentially unchanged. Any modifications should thus be restricted to a minimum and closely watched for changes in the specificity and affinity of the antibody. On the other hand, framework residues in theory can be derived from any human variable region.

In order to create a reshaped antibody which shows an acceptable or an even improved affinity, a human framework sequences should be chosen, which is equally suitable for creating a reshaped variable region and for retaining antibody affinity.

In order to achieve this goal, the best-fit strategy was developed. As it is known that the framework sequences serve to hold the CDRs in their correct spatial orientation for interaction with antigen, and that framework residues can sometimes even participate in antigen binding, this strategy aims at minimizing changes that may negatively effect the three-dimensional structure of the antibody by deriving the human framework sequence used for antibody reshaping from the human variable region that is most homologous or similar to the non-human-, particularly the rodent-derived variable region. This will also maximise the likelihood that affinity will be retained in the reshaped antibody.

At its simplest level, the "best fit" strategy involves comparing the donor rodent V-region with all known human V-region amino acid sequences, and then selecting the most homologous to provide the acceptor framework regions for the humanization exercises. In reality there are several other factors which should be considered, and which may influence the final selection of acceptor framework regions. Molecular modelling predictions may be used in this regard prior to any experimental work in an attempt to maximise the affinity of the resultant reshaped antibody. Essentially, the goal of the modelling is to predict which key residues (if any) of the most homologous human framework should be left as in the rodent to obtain the best affinity in the reshaped antibody.

In one embodiment of the invention, the CDRs are obtainable from mouse monoclonal antibody, particularly from mouse monoclonal antibody ACI-01-Ab7C2 (named "mC2" throughout the application) described in co-pending application EP 05 02 7092.5 filed Dec. 12, 2005, the disclosure of which is incorporated herein by reference.

Hybridoma cells FP-12H3-C2, producing mouse monoclonal antibody ACI-01-Ab7C2 (named "mC2" and hC2 for the humanized C2 antibody, throughout the application) were deposited 1 Dec. 2005 in co-pending application no EP05027092.5 with the "Deutsche Sammlung von Mikroorganismen und Zellkulturen GmbH (DSMZ) in Braunschweig, Mascheroder Weg 1 B, 38124 Braunschweig, under the provisions of the Budapest Treaty and given accession no DSM ACC2750.

The mouse antibody may be raised against a supramolecular antigenic construct comprising an antigenic peptide corresponding to the amino acid sequence of the β-amyloid peptide, particularly of β-amyloid peptide $A\beta_{1-15}$, $A\beta_{1-16}$ and $A\beta_{1-16(\Delta 14)}$, modified with a hydrophobic moiety such as, for example, palmitic acid or a hydrophilic moiety such as, for example, polyethylene glycol (PEG) or a combination of both, wherein the hydrophobic and hydrophilic moiety, respectively, is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophobic and hydrophilic moiety to the peptide fragment. When a PEG is used as the hydrophilic moiety, the free PEG termini is covalently bound to phosphatidylethanolamine or any other compound suitable to function as the anchoring element, for example, to embed the antigenic construct in the bilayer of a liposome.

In particular, a mouse antibody may be raised against a supramolecular antigenic construct comprising an antigenic peptide corresponding to the amino acid sequence of the β-amyloid peptide A$β_{1-16}$ modified with a hydrophilic moiety such as, for example, polyethylene glycol (PEG) hydrophilic moiety is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophobic and hydrophilic moiety to the peptide fragment. When a PEG is used as the hydrophilic moiety, the free PEG termini are covalently bound to phosphatidylethanolamine or any other compound suitable to function as the anchoring element, for example, to embed the antigenic construct in the bilayer of a liposome.

In an embodiment of the invention, a chimeric antibody or a fragment thereof, or a humanized antibody or a fragment thereof is provided which comprises in the variable region at least one CDR of non-human origin embedded in one or more human- or primate-derived framework regions and combined with a constant region derived from a human or primate source antibody, which chimeric antibody or a fragment thereof, or a humanized antibody or a fragment thereof is capable of specifically recognizing and binding β-amyloid monomeric peptide.

The CDRs contain the residues most likely to bind antigen and must be retained in the reshaped antibody. CDRs are defined by sequence according to Kabat et al., Sequence of Proteins of Immunological Interest, 5$^{th}$ Edition, The United States Department of Health and Human Services, The United States Government Printing Office, 1991. CDRs fall into canonical classes (Chothia et al, 1989 *Nature,* 342, 877-883) where key residues determine to a large extent the structural conformation of the CDR loop. These residues are almost always retained in the reshaped antibody.

In the process for preparing a humanized antibody according to the invention, the amino acid sequences of the C2 heavy chain and light chain variable regions ($V_H$ and $V_K$) are compared to rodent antibody $V_H$ and $V_K$ sequences in the NCBI and Kabat databases.

The closest match mouse germ line gene to C2 $V_K$ is bb1, Locus MMU231201, (Schable et al, 1999). A comparison reveals that two amino acids differ from this germ line sequence, both located within CDRL1. Mature murine antibodies with similar, but not identical, sequence can be found. Several have an identical CDRL2 and identical CDRL3, but the CDRL1 of C2 seems to be unique. Comparison with human germ line $V_K$ sequences shows that genes from subgroup $V_K$II are the best match for C2 $V_K$ (Cox et al, 1994). C2 $V_K$ can thus be assigned to Kabat subgroup MUV$_K$II.Sequence.

DPK15 together with the human J region HuJ$_K$1 may be selected to provide the acceptor framework sequences for the humanized $V_K$.

The residues at the interface between the variable light and heavy chains have been defined (Chothia et al, 1985 *J. Mol. Biol.,* 186, 651-663). These are usually retained in the reshaped antibody. The Phe at position 87 of mouse C2 $V_K$ is unusual at the interface, where a Tyr is more common in the $V_K$II subgroup, indicating that this framework residue may be important for antibody activity. Tyr 87 is present in the human germline and humanized C2VK.

The humanized $V_K$ sequences thus may be designed such that the C2HuVK1 consists of mouse C2 $V_K$ CDRs with frameworks from DPK 15 and human J$_K$1. In a specific embodiment of the invention, murine residues may be substituted in the human framework region at positions 45, and/or 87. In the CDR2 region obtainable from a mouse monoclonal antibody, particularly murine antibody ACI-01-Ab7C2, amino acid substitutions may be made at Kabat positions 50 and/or 53. Residue 45 may be involved in supporting the conformation of the CDRs. Residue 87 is located at the interface of the $V_H$ and $V_K$ domains. Therefore these residues may be critical for maintenance of antibody binding.

The closest match mouse germ line gene to C2 $V_H$ AF is VH7183, Locus AF120466, (Langdon et al, 2000). Comparison with human germ line $V_H$ sequences shows that genes from subgroup $V_H$III are the best match for C2 $V_H$. C2 $V_H$ AF can be assigned to Kabat subgroup MuV$_H$IIID. Sequence DP54 together with the human J region HuJ$_H$6 can be selected to provide the acceptor framework sequences for the humanized $V_H$.

The comparison shows that there are nine amino acid differences between the C2 VH sequences and the human acceptor germ line sequence DP54 and J$_H$6, most being located within CDRH2. Mature murine antibodies with identical or similar (one residue different) CDRH1 or with similar CDRH2 (one residue different) are found, but none with all three CDRs identical to C2 $V_H$ AF. CDRH3 of C2 antibody is unusually short, consisting of only three residues. However, other antibodies are found in the database with CDRH3 of this length. Residue 47 of C2 $V_H$ is Leu rather than the more common Trp, and residue 94 is Ser rather than the normal Arg, indicating that these framework residues may be important for antibody activity.

Various humanized $V_H$ sequences may be designed. C2HuVH1 consists of C2 $V_H$ AF CDRs with frameworks from DP54 and HuJ$_H$6. In a specific embodiment of the invention, murine residues may be substituted in the human framework region at positions 47 or 94 or both. Residue 47 in framework 2 makes contact both with the CDRs and with the $V_K$ domain. Residue 94 may be involved in supporting the conformation of the CDRs. Therefore these residues may be critical for maintenance of antibody binding.

Different HCVR and LCVR regions may be designed which comprise the non-human CDRs obtainable from the donor antibody, for example, a murine antibody, embedded into the native or modified human- or primate-derived framework regions. The modification may particularly concern an exchange of one or more amino acid residues within the framework region by non-human residues, particularly murine residues, more commonly found in this position in the respective subgroups or by residues which have similar properties to the ones more commonly found in this position in the respective subgroups.

The modification of the framework region the framework sequences serve to hold the CDRs in their correct spatial orientation for interaction with antigen, and that framework residues can sometimes even participate in antigen binding. In one embodiment of the invention measures are taken to further adapt the selected human framework sequences to make them most similar to the sequences of the rodent frameworks in order to maximise the likelihood that affinity will be retained in the reshaped antibody.

Accordingly, murine residues in the human framework region may be substituted. In particular, murine residues may be substituted in the human framework region of the Heavy Chain Variable (HCVR) region at positions 47 or 94 or both and in the human framework region of the Light Chain Variable (LCVR) region at positions 45 and/or 87. In the CDR2 region obtainable from a mouse monoclonal antibody, particularly murine antibody ACI-01-Ab7C2, amino acid substitutions may be made at Kabat positions 50 and/or 53.

The residues found in the above indicated positions in the human framework region may be exchanged by murine residues more commonly found in this position in the respective subgroups. In particular, the Trp in Kabat position 47 in the human- or primate-derived framework region of the Heavy Chain Variable Region as shown in SEQ ID NO: 15 may be replaced by an Leu or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Trp in Kabat position 47 in the human- or primate-derived framework region of the Heavy Chain Variable Region as shown in SEQ ID NO: 15 may further be replaced by an amino acid selected from the group consisting of norleucine, Ile, Val, Met, Ala, and Phe, particularly by Ile. Alternative conservative substitutions may be contemplated which are conformationally and antigenically neutral.

The Arg in Kabat position 94 in the human- or primate-derived framework region of the Heavy Chain Variable Region as shown in SEQ ID NO: 15 may be replaced by Ser or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Arg in Kabat position 94 in the human- or primate-derived framework region of the Heavy Chain Variable Region as shown in SEQ ID NO: 15 may alternatively be replaced by Thr.

In another embodiment of the invention, both residues may be replaced in the humanized antibody.

The Gln in Kabat position 45 in the human- or primate-derived framework region of the Light Chain Variable Region as shown in SEQ ID NO: 12 may be replaced by Lys or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Gln in Kabat position 45 in the human- or primate-derived framework region of the Light Chain Variable Region as shown in SEQ ID NO: 12 may be replaced by an amino acid selected from the group consisting of Arg, Gln, and Asn, particularly by Arg.

The Leu in Kabat position 50 in the human- or primate-derived framework region of the Light Chain Variable Region as shown in SEQ ID NO: 12 may be replaced by Lys or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Leu in Kabat position 50 in the human- or primate-derived framework region of the Light Chain Variable Region as shown in SEQ ID NO: 12 may be replaced by an amino acid selected from the group consisting of Arg, Gln, and Asn, particularly by Arg.

The Asn in Kabat position 53 in the human- or primate-derived framework region of the Light Chain Variable Region as shown in SEQ ID NO: 12 may be replaced by His and Gln or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Asn in Kabat position 53 in the human- or primate-derived framework region of the Light Chain Variable Region as shown in SEQ ID NO: 12 may be replaced by an amino acid selected from the group consisting of Gln, His, Lys and Arg.

The Thr in Kabat position 87 in the human- or primate-derived framework region of the Light Chain Variable Region as shown in SEQ ID NO: 12 may be replaced by Phe or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Tyr in Kabat position 87 in the human- or primate-derived framework region of the Light Chain Variable Region as shown in SEQ ID NO: 12 may be replaced by an amino acid selected from the group consisting of Leu, Val, Ile, and Ala, particularly by Leu.

The so obtained variable region comprising at least one CDR of non-human origin embedded in one or more human- or primate-derived framework regions may then be combined with a constant region derived from a human or primate source antibody, particularly with human IgG4 or κ constant regions respectively. The IgG4 constant region may be modified by, for example, changing Serine at position 228 in the hinge region to Proline (HuIgG4 Ser-Pro). This mutation stabilizes the interchain disulphide bond and prevents the formation of half molecules that may occur in native human IgG4 preparations. The IgG4 constant region may be further modified by deletion of the terminal Lys in position 439 as shown in SEQ ID NO: 16.

The modified variable regions may be constructed by method known in the art such as, for example overlapping PCR recombination. The expression cassettes for the chimeric antibody, C2 ChV$_H$ AF and C2 ChV$_K$, may be used as templates for mutagenesis of the framework regions to the required sequences. Sets of mutagenic primer pairs are synthesized encompassing the regions to be altered. The humanized $V_H$ and $V_K$ expression cassettes produced may be cloned into appropriate cloning vectors know in the art such as, for example, pUC19. After the entire DNA sequence is confirmed to be correct for each $V_H$ and $V_K$, the modified heavy and light chain V-region genes can be excised from the cloning vector as expression cassettes. These can then be transferred to appropriate expression vectors such as pSVgpt and pSVhyg which include human IgG4 Ser-Pro or κ constant regions respectively.

Expression Vectors

Expression vector pSVgpt is based on pSV$_2$gpt (Mulligan and Berg, 1980) and includes the ampicillin resistance gene for selection in bacterial cells, the gpt gene for selection in mammalian cells, the murine heavy chain immunoglobulin enhancer region, genomic sequence encoding the constant region gene and SV40 poly A sequences. The heavy chain variable region for expression is inserted as a HindIII to BamHI fragment.

Expression vector pSVhyg includes the ampicillin resistance gene for selection in bacterial cells, the hyg gene for selection in mammalian cells, the murine heavy chain immunoglobulin enhancer region, genomic sequence encoding the kappa constant region gene and including the kappa enhancer and SV40 poly A sequences. The light chain variable region for expression is inserted as a HindIII to BamHI fragment.

The DNA sequence is then to be confirmed to be correct for the humanized $V_H$ and $V_K$ in the expression vectors.

For antibody production the humanized heavy and light chain expression vectors may be introduced into appropriate production cell lines know in the art such as, for example, NS0 cells. Introduction of the expression vectors may be accomplished by co-transfection via electroporation or any other suitable transformation technology available in the art. Antibody producing cell lines can then be selected and expanded and humanized antibodies purified. The purified antibodies can then be analyzed by standard techniques such as SDS-PAGE.

Antibody with Improved Affinity, Specificity, Stability

The CDRL2 sequence ("KVSNRFS") (SEQ ID NO: 5) of the mouse C2 antibody maybe modified slightly without adversely affecting antibody activity. Conservative substitutions may be made through exchange of R for K at position 50 and S for N at position 53. The two alternative CDRL2 sequences are therefore "RVSNRFS" (SEQ ID NO: 40) and "KVSSRFS" (SEQ ID NO: 41), respectively. These are incorporated into the murine VK sequence with no other changes, as C2 VK-R and C2 VK-S, respectively.

The affinity, specificity and stability of an antibody according to the invention as described herein before or a fragment thereof can be modified by change of its glycosylation profile or pattern resulting in improved therapeutic values.

To achieve this change in glycosylation pattern, host cells may be engineered such that they are capable of expressing a preferred range of a glycoprotein-modifying glycosyl transferase activity which increases complex N-linked oligosaccharides carrying bisecting GIcNAc. Further, modified glycoforms of glycoproteins may be obtained, for example antibodies, including whole antibody molecules, antibody fragments, or fusion proteins that include a region equivalent to the Fc region of an immunoglobulin, having an enhanced Fc-mediated cellular cytotoxicity.

Methods of obtaining antibodies with modified glycosylation pattern are known to those skilled in the art and described, for example, in EP1071700, US2005272128, Ferrara et al (2006) J Biol Chem 281(8), 5032-5036); Ferrara et al (2006) Biotechnology and Bioengineering 93(5), 851-861.

Pharmaceutical Preparation and Administration

The antibodies according to the invention, but particularly a monoclonal antibody according the invention, can be prepared in a physiologically acceptable formulation and may comprise a pharmaceutically acceptable carrier, diluent and/ or excipient using known techniques. For example, the antibody according to the invention and as described herein before including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well know to those skilled in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine, M1 agonists and other drugs including any amyloid or tau modifying drug and nutritive supplements such as, for example, vitamin B12, cysteine, a precursor of acetylcholine, lecithin, choline, *Ginkgo biloba*, acetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, eg intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the antibody or active fragment thereof to traverse the blood-brain barrier. Certain neurodegenerative diseases are associated with an increase in permeability of the blood-brain barrier, such that the antibody or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or active fragment thereof across the blood-brain barrier include, but are not limited to, encapsulating the antibody or active fragment thereof in liposomes that are coupled to antibody binding fragments that bind to receptors on the vascular endothelium of the blood-brain barrier (see, e.g., U.S. Patent Application Publication No. 20020025313), and coating the antibody or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Detection/Diagnosis

In a further embodiment the present invention provides methods and kits for the detection and diagnosis of amyloid-associated diseases or conditions. These methods include known immunological methods commonly used for detecting or quantifying substances in biological samples or in an in situ condition.

Diagnosis of an amyloid-associated disease or condition in a patient may be achieved by detecting the immunospecific binding of a monoclonal antibody or an active fragment thereof to an epitope of the amyloid protein in a sample or in situ, which includes bringing the sample or a specific body part or body area suspected to contain the amyloid protein into contact with an antibody which binds an epitope of the amyloid protein, allowing the antibody to bind to the amyloid protein to form an immunological complex, detecting the formation of the immunological complex and correlating the presence or absence of the immunological complex with the presence or absence of amyloid protein in the sample or specific body part or area.

Biological samples that may be used in the diagnosis of an amyloid-associated disease or condition are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the amyloid protein in a sample any immunoassay known to those of ordinary skill in the art. (See Harlow and Lane, Antibodies: A Laboratory Manual (Cold Spring Harbor Laboratory, New York 1988 555-612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the antibody or any active and functional part thereof may be administered to the organism to be diagnosed by methods known in the art such as, for example, intravenous, intranasal, intraperitoneal, intracerebral, intraarterial injection such that a specific binding between the antibody according to the invention with an eptitopic region on the amyloid protein may occur. The antibody/antigen complex may be detected through a label attached to the antibody or a functional fragment thereof.

The immunoassays used in diagnostic applications typically rely on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antibody may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein. The antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system often referred to as fast format systems because they are adapted to rapid determinations of the presence of an analyte, may also be employed within the scope of the present invention. The system requires high affinity between the antibody and the analyte. According to one embodiment of the present invention, the presence of the amyloid protein is determined using a pair of antibodies, each specific for amyloid protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting amyloid protein in a sample of biological fluid. In this method, the analyte (amyloid protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The present invention also relates to a diagnostic kit for detecting amyloid protein in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of amyloid-associated diseases and conditions comprising antibodies according to the present invention. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to amyloid protein to form an immunological complex and detecting the formation of the immunological complex such that presence or absence of the immunological complex correlates with presence or absence of amyloid protein.

EXAMPLES

Materials

The development and preparation of mouse monoclonal antibody ACI-01-Ab7C2 (named "mC2" and hC2 for the humanized C2 antibody, throughout the application) is described in co-pending application EP 05 02 7092.5 filed Dec. 12, 2005, the disclosure of which is incorporated herein by reference.

Hybridoma cells FP-12H3-C2, producing mouse monoclonal antibody ACI-01-Ab7C2 (named "mC2" and hC2 for the humanized C2 antibody, throughout the application) were deposited 1 Dec. 2005 in co-pending application no EP05027092.5 with the "Deutsche Sammlung von Mikroorganismen und Zellkulturen GmbH (DSMZ) in Braunschweig, Mascheroder Weg 1 B, 38124 Braunschweig, under the provisions of the Budapest Treaty and given accession no DSM ACC2750.

Hybridoma cells were cultured in Dulbecco's modified Eagle Medium (DMEM) supplemented with 10% foetal bovine serum and antibiotics (Penicillin/Streptomycin). The isotype of the antibody produced was checked and found to be mouse IgG2b/kappa, as expected.

Assay

An ELISA for binding to Amyloid Beta provided a reliable measure of the potency of C2 antibodies. Positive control antibodies, murine FP-12H3-C2 antibody (Genovac Lot No: AK379/01), and standard Chemicon antibody 1560 (Lot no: 0508008791).

Choice of Human Constant Regions

As immune system recruitment is not desirable for the clinical antibody candidate, the selected human constant region for the heavy chain was human IgG4, modified to change Serine at position 228 in the hinge region to Proline (HuIgG4 Ser-Pro). This mutation stabilizes the interchain disulphide bond and prevents the formation of half molecules that may occur in native human IgG4 preparations. The antibody expressed from the production cell lines will also have the terminal lysine removed. The sequences of human constant regions HuIgG4 Ser-Pro and human Kappa are given in SEQ ID NO: 17 and 14, respectively.

Example 1

Cloning and Sequencing of Antibody Variable Regions

Total RNA was prepared from $3 \times 10^6$ hybridoma cells (one T175 flask) using the Qiagen RNeasy mini kit (Cat No: 74104). RNA was eluted in 50 μL water and checked on a 1.2% agarose gel. The conditioned medium from the cells was retained and a sample used for testing in the antibody activity assay.

$V_H$ and $V_K$ cDNAs were prepared using reverse transcriptase with mouse IgG and κ constant region primers. The first strand cDNAs were amplified by PCR using a large set of signal sequence primers. The amplified DNAs were gel-purified and cloned into the vector pGem® T Easy (Promega). The $V_H$ and $V_K$ clones obtained were screened for inserts of the expected size by PCR and the DNA sequence of selected clones determined by automated DNA sequencing. The locations of the complementarity determining regions (CDRs) in the sequences were determined with reference to other antibody sequences (Kabat E A et al., 1991). The numbering convention of Kabat for antibody variable regions is used throughout this application; hence residue numbers may differ from the strict linear number.

The DNA sequence and deduced amino acid sequence for mC2 $V_K$ is shown in SEQ ID NO: 29 and 27, respectively. Four clones gave this identical productive sequence. A non-productive aberrant $V_K$ sequence that arises from the hybridoma fusion partner was also found in a number of clones.

For mC2 $V_H$, two different productive sequences were isolated. The mC2 $V_H$ AF sequence (see SEQ ID NO: 30) was found in a total of 29 clones, with 14 single base pair changes in individual clones. The mC2 $V_H$ B sequence was found in a total of 8 clones. Five of these represented the majority sequence, with the other 3 clones being variations on this. It is possible that these similar $V_H$ B sequences arose as an artifact of the PCR amplification. A non-productive aberrant $V_H$ was also obtained from the C2 hybridoma and is attributed to defective V-D-J joining.

In order to determine which is the correct active mC2 $V_H$, two chimeric antibodies were prepared with the two different $V_H$ sequences, AF and B, combined with the mC2 $V_K$, to be tested for the correct antibody activity.

Example 2

Construction of Chimeric Antibody Genes

A human chimeric antibody in its most common form consists of human constant regions linked to murine (or other non-human) variable regions. A chimeric antibody provides a very useful tool, firstly for confirmation that the correct variable regions have been identified, secondly for use as a control antibody in antigen binding assays with the same effector functions and utilizing the same secondary detection reagents as a humanized or engineered antibody, and also may be used to investigate the pharmacokinetic and other properties of the human constant regions with reference to the particular target for the antibody.

Two chimeric heavy chain expression vectors were constructed consisting of mC2 $V_H$ AF or mC2 $V_H$ B variable regions linked to HuIgG4 (Ser-Pro) constant region in the expression vector pSVgpt. This is based on pSV$_2$gpt (Mulligan and Berg, 1980) and includes the ampicillin resistance gene for selection in bacterial cells, the gpt gene for selection in mammalian cells, the murine heavy chain immunoglobulin enhancer region, genomic sequence encoding the constant region gene and SV40 poly A sequences. The heavy chain variable region for expression is inserted as a HindIII to BamHI fragment.

A chimeric light chain vector was constructed consisting of C2 VK linked to human C Kappa constant region in the expression vector pSVhyg. (Hieter P A et al, 1980) pSVhyg includes the ampicillin resistance gene for selection in bacterial cells, the hyg gene for selection in mammalian cells, the murine heavy chain immunoglobulin enhancer region, genomic sequence encoding the kappa constant region gene and including the kappa enhancer and SV40 poly A sequences. The light chain variable region for expression is inserted as a HindIII to BamHI fragment.

Expression cassettes for the murine C2 VH and VK sequences were constructed by addition of 5' flanking sequence including the leader signal peptide, leader intron and the murine immunoglobulin promoter, and 3' flanking sequence including the splice site and intron sequence, using the vectors VH-PCR1 and VK-PCR1 as templates (Riechmann et al., 1988). The DNA sequence was confirmed to be correct for the VH and VK in the chimeric expression vectors. The DNA and amino acid sequences of the VH and VK genes in the expression cassettes are shown in FIGS. 1 and 2.

Example 3

Expression of Chimeric Antibodies 3.1 Expression in Stable Cell Lines

The host cell line for antibody expression was NS0, a non-immunoglobulin producing mouse myeloma, obtained from the European Collection of Animal Cell Cultures, Porton UK (ECACC No 85110503). The heavy and light chain expression vectors were co-transfected into NS0 cells by electroporation. Colonies expressing the gpt gene were selected in Dulbecco's Modified Eagle's Medium (DMEM) supplemented with 10% foetal bovine serum (FBS), 0.8 μg/ml mycophenolic acid and 250 μg/ml xanthine. Transfected cell clones were screened for production of human antibody by ELISA for human IgG. Cell lines secreting antibody were expanded and the highest producers selected and frozen down in liquid nitrogen. The best producing cell lines for each antibody were expanded in medium as above but with only 5% FBS. Chimeric antibodies were purified using Prosep®-A (Bioprocessing Ltd). The concentration was determined by ELISA for human IgGκ antibody. The antibodies were also analyzed by SDS-PAGE.

3.2 Transient Expression of Chimeric Antibodies

To expedite the testing of the different chimeric antibodies, transient expression was used to produce quickly small quantities of cell supernatant containing recombinant antibody for testing. The mC2 $V_H$ and $V_K$ expression cassettes were transferred to vectors based on pcDNA3.1 (Invitrogen) for transient expression. The heavy chain vector included a human IgG constant region. The light chain vector included a human kappa constant region. Both mC2 $V_H$ AF and mC2 $V_H$ B were transfected with mC2 $V_K$ into human embryonic kidney (HEK 298) cells with Lipofectamine 2000 reagent (Invitrogen Cat No: 11668) according to the protocol supplied by the manufacturer. Conditioned medium was harvested from cells 3 days after transfection. The amount of antibody produced was determined by ELISA for human IgGκ antibody.

Example 4

Activity of Chimeric C2 Antibodies 4.1 Activity of Chimeric C2 Antibodies Produced by Transient Transfection Samples of conditioned medium from transient transfection for the two different chimeric antibodies were tested in the ELISA for binding to Amyloid Beta. The results clearly indicate that the C2 VHAF is the correct sequence. The C2 $V_H$ AF/C2 $V_K$ chimeric antibody binds well in the assay, but the C2 $V_H$ B/C2 $V_K$ does not show any binding at all. The Chemicon 1560 murine control antibody showed good binding, but binding by the purified murine C2 antibody supplied was low. It should be noted that a different secondary antibody was employed for the murine antibodies with the mouse constant regions compared to the chimeric antibodies with human constant regions, so the results are not directly comparable. Conditioned medium from the C2 hybridoma was later found to give a good result in the assay.

4.2 Activity of Purified Chimeric C2 Antibodies

The two different C2 chimeric antibodies were purified from stable NS0 cell lines as described and tested using the Amyloid Beta ELISA. The results obtained are in accordance with the results obtained with transiently expressed antibody. The C2 ChVH AF/ChVK antibody binds well in the ELISA and the C2 ChVH B/ChVK antibody does not bind at all.

Example 5

Design of Humanized C2 Antibody Genes

The mC2 $V_H$ and $V_K$ amino acid sequences were compared to rodent antibody $V_H$ and $V_K$ sequences in the NCBI and Kabat databases.

5.1 Light Chain Variable Region

The closest match mouse germ line gene to mC2 $V_K$ is bb1, Locus MMU231201, (Schable et al, 1999). Only two amino acids differ from this germ line sequence, both located within CDRL1. Mature murine antibodies with similar, but not identical, sequence are found. Several have an identical CDRL2 and identical CDRL3, but the CDRL1 of mC2 seems to be unique. mC2 $V_K$ can be assigned to Kabat subgroup Mu$V_K$II-Position 87 of mC2 $V_K$ is F rather than the Y that is more common in the subgroup, indicating that this framework residue may be important for antibody activity. Comparison with human germ line $V_K$ sequences shows that genes from subgroup $V_K$II are the best match for mC2 $V_K$ (Cox et al, 1994). Sequence DPK15 together with the human J region HuJ$_K$1 were selected to provide the acceptor framework sequences for the humanized $V_K$.

Four humanized $V_K$ sequences were designed. C2HuVK1 consists of mC2 $V_K$ CDRs with frameworks from DPK 15 and human J$_K$1. In versions 2, 3 and 4 murine residues have been substituted in the framework at positions 45 or 87 or both. Residue 45 may be involved in supporting the conformation of the CDRs. Residue 87 is located at the interface of the $V_H$ and $V_K$ domains. Therefore these residues may be critical for maintenance of antibody binding.

The positions and changes that have been made in the light chain framework regions are shown in Table 6. A comparison of the humanized sequences with mC2 $V_K$ sequence, and with DPK15 and human J$_K$1

5.2 Heavy Chain Variable Region

The closest match mouse germ line gene to mC2 $V_H$ AF is VH7183, Locus AF120466, (Langdon et al, 2000). The comparison is shown in FIG. 3. Nine amino acids differ from this germ line sequence, most being located within CDR2. Mature murine antibodies with identical or similar (one residue different) CDR1 or with similar CDR2 (one residue different) are found, but none with all three CDRs identical to mC2 $V_H$ AF. CDR3 of mC2 antibody is unusually short, consisting of only three residues. However, other antibodies are found in the database with CDR3 of this length. mC2 $V_H$ AF can be assigned to Kabat subgroup Mu$V_H$IIID. Residue 47 of mC2 $V_H$ is L rather than the more common W, and residue 94 is S rather than the normal R, indicating that these framework residues may be important for antibody activity. Comparison with human germ line $V_H$ sequences shows that genes from subgroup $V_H$III are the best match for mC2 $V_H$. Sequence DP54 together with the human J region HuJ$_H$6 was selected to provide the acceptor framework sequences for the humanized $V_H$.

Four humanized $V_H$ sequences were designed. C2HuVH1 consists of mC2 $V_H$ AF CDRs with frameworks from DP54 and HuJ$_H$6. In versions 2, 3 and 4 murine residues have been substituted in the framework at positions 47 or 94 or both. Residue 47 in framework 2 makes contact both with the CDRs and with the $V_K$ domain. Residue 94 may be involved in supporting the conformation of the CDRs. Therefore these residues may be critical for maintenance of antibody binding.

The positions and changes that have been made in the heavy chain framework regions are shown in Table 7.

Example 6

Construction of Humanized Antibody Genes

The modified variable regions were constructed by the method of overlapping PCR recombination. The expression cassettes for the chimeric antibody, C2 Ch$V_H$ AF and C2 Ch$V_K$, were used as templates for mutagenesis of the framework regions to the required sequences. Sets of mutagenic primer pairs were synthesized encompassing the regions to be altered. The humanized $V_H$ and $V_K$ expression cassettes produced were cloned into pUC19 and the entire DNA sequence was confirmed to be correct for each $V_H$ and $V_K$. The modified heavy and light chain V-region genes were excised from pUC19 as HindIII to BamHI expression cassettes. These were transferred to the expression vectors pSVgpt and pSVhyg which include human IgG4 Ser-pro or K constant regions respectively, as for the chimeric antibody vectors. The DNA sequence was confirmed to be correct for the humanized $V_H$ and $V_K$ in the expression vectors.

Example 7

Expression of Humanized Antibodies 7.1 Expression in Stable Cell Lines

The humanized heavy and light chain expression vectors were co-transfected into NS0 cells by electroporation, as for the expression of chimeric antibodies. Antibody producing cell lines were selected and expanded and humanized antibodies purified, exactly as for the chimeric antibody. The purified antibodies were analyzed by SDS-PAGE.

7.2 Transient Expression of Humanized Antibodies

To expedite testing of the different humanized $V_H$ and $V_K$ constructs, the C2 humanized $V_H$ and $V_K$ expression cassettes were also transferred to the vectors for transient expression described in section 7.2. The four humanized C2 $V_K$ constructs were co-transfected with the chimeric C2 $V_H$ construct into HEK293 cells. Similarly, the four humanized C2 $V_H$ constructs were co-transfected with the chimeric C2 $V_K$ construct into HEK293 cells. Conditioned medium was harvested from cells three days after transfection. The amount of antibody produced was determined by ELISA for human IgGκ antibody.

Example 8

Activity of Humanized C2 Antibodies 8.1 Activity of Humanized C2 Antibodies Produced by Transient Transfection Samples of conditioned medium from the transient transfection were tested in the Amyloid Beta ELISA. The results obtained clearly indicate that the humanized VH constructs C2 HuVH AF versions 2 and 4 are functional when combined with the chimeric C2 kappa chain, and are comparable to the chimeric C2 antibody in the assay. In contrast, the antibodies containing C2 HuVH AF versions 1 and 3 combined with the chimeric C2 kappa chain show no binding at all in the assay. This indicates that the substitution of the murine residue at position 94 is essential for antibody activity. Antibodies containing the chimeric C2 heavy chain combined with the four humanized C2 kappa chains all showed good binding, comparable to the chimeric antibody, in the ELISA.

8.2 Activity of Purified Humanized C2 Antibodies

Eight different humanized C2 antibodies comprising all combinations of two humanized heavy chains and four humanized light chains were purified from stable NS0 cell lines as described and tested using the Amyloid Beta ELISA (FIG. 4).

The results obtained clearly indicate that C2 HuVH4 antibodies perform better in the assay than C2 HuVH2 antibodies. Of the C2 HuVH2 antibodies, C2 HuVH2/HuVK3 shows the best binding activity, but this is approximately 2 fold reduced compared to the chimeric control antibody C2 ChVHAF/ChVK. C2 HuVH2/HuVK2 activity is four to five fold reduced compared to the control. The activities of the antibodies comprising C2HuVH4 with the four different humanized light chains are similar. The highest activity is observed for C2HuVH4/HuVK1 and all four antibodies are close to the control chimeric antibody in the assay.

Example 9

Modifications to CDRL2

9.1 Design Light Chain with Modified CDR 2

As noted above, many antibodies share the same CDRL2 sequence ("KVSNRFS") (SEQ ID NO: 5) as the C2 antibody. It was decided to test whether CDRL2 could be modified slightly without adversely affecting antibody activity. Two conservative substitutions were selected: R for K at position 50 and S for N at position 53. The two alternative CDRL2 sequences are therefore "RVSNRFS" (SEQ ID NO: 40) and "KVSSRFS" (SEQ ID NO: 41). These were incorporated into the murine VK sequence with no other changes, as mC2 VK-R and mC2 VK-S respectively.

9.2 Transient Expression of Modified CDRL2 Antibody

The two C2 light chain constructs with modified CDRL2 described in Section 11.2.1 were cloned into the light chain vector for transient expression. Each was co-transfected with the chimeric C2 $V_H$ vector into HEK293 cells. Conditioned medium was harvested from cells three days after transfection. The amount of antibody produced was determined by ELISA for human IgGκ antibody.

9.3 Activity of C2 Antibody with Modified CDRL2

Samples of conditioned medium from the transient transfection of mC2 $V_K$s with modified CDRL2 combined with mC2 $V_H$ were tested in the Amyloid Beta ELISA. (FIG. 5) Both the VK-R and the VK-S antibodies are comparable to the chimeric C2 antibody, indicating that the individual modifications to CDRL2 chosen do not markedly affect the activity of the antibody in the assay.

Example 10

Affinity Determination

To assess the binding specificity and affinity of mouse (ACI-01-Ab-7-C2) chimeric (AF) and humanized antibodies (H4K1; H4K4), BIACORE® analysis was performed using amyloid beta 1-42 monomers and fibers as antigen immobilized on a CM5 chip. BIACORE® technology utilizes changes in the refractive index at the surface layer upon binding of the antibody to the antigen immobilized on the layer. Binding is detected by surface plasmon resonance (SPR) of laser light refracting from the surface. Analysis of the signal kinetics on rate and off rate allows the discrimination between non-specific and specific interaction. The concentration of antibody used was in the range of 0.05 μM to 1.0 μM.

TABLE 1

Binding specificity and affinity of mouse (ACI-01-Ab-7-C2) chimeric (AF) and humanized antibodies (H4K1; H4K4) for amyloid beta 1-42 monomers and fibers

|  | Monomers | | | Fibers | | |
|---|---|---|---|---|---|---|
|  | $k_a$ (1/Ms) | $k_d$ (1/s) | KD (M) | $k_a$ (1/Ms) | $k_d$ (1/s) | KD (M) |
| Mouse ACI-01-Ab-7-C2 | 1.8E+04 | 2.7E−03 | 1.5E−07 | 2.4E+04 | 9.9E−04 | 4.1E−08 |
| chimeric AF | 4.7E+04 | 9.5E−04 | 2E−08 | 5.1E+04 | 3.3E−04 | 6.5E−09 |

TABLE 1-continued

Binding specificity and affinity of mouse (ACI-01-Ab-7-C2) chimeric (AF)
and humanized antibodies (H4K1; H4K4) for amyloid beta 1-42 monomers and fibers

| | Monomers | | | Fibers | | |
|---|---|---|---|---|---|---|
| | $k_a$ (1/Ms) | $k_d$ (1/s) | KD (M) | $k_a$ (1/Ms) | $k_d$ (1/s) | KD (M) |
| humanized H4K1 | 5.0E+04 | 9.5E−04 | 1.9E−08 | 4.9E+04 | 2.3E−04 | 4.7E−09 |
| humanized H4K4 | 2.5E+04 | 4.4E−04 | 1.8E−08 | 1.3E+05 | 3.0E−04 | 2.3E−09 |

Example 11

Immunhistochemical Binding Assay 11.1 Human Brain Sections

Brains from healthy, non-demented pre-AD and AD patients were obtained from the Universitätsklinik in Bonn after ethical approval. Brains were fixed in formaldehyde and the hippocampus region was dehydrated, embedded in paraffin and 5 μm sections were cut with a microtome. Paraffin sections were stored at RT until use. For fresh material, 5 μm cryosections were cut with a cryostat and sections stored at −80° C. until use.

11.2 Immunohistochemistry

Paraffin sections were deparaffinized and rehydrated by bathing slides in xylene followed by 100% ethanol, 90% ethanol and 70% ethanol. Background was decreased by 30 minutes incubation in 10% $H_2O_2$, 10% methanol in water. Antigen retrieval was obtained by incubating the slides in 100% formic acid for 3 minutes. After 3 washes in Tris buffered saline (TBS, pH 7.5), non-specific labeling was blocked by a 2 hour incubation of the slides in 10% BSA, 0.25% Triton X-100 in TBS. After washing (3 washes in TBS) blocking of endogenous antibodies was performed by adding a non-labeled anti-human IgG (Biomeda) and incubating slides in humid chambers overnight at RT. After another 3 washes, the primary human anti amyloid antibody was added to the slides and incubated another 24 hours at RT. Following washing, an alkaline phosphatase labeled secondary anti human IgG (Sigma) was added to the slides and incubated for 2 hours at RT. After washing, slides were developed with Liquid permanent Red (Dakocytomation) washed with water and air-dried before mounting with permanent mounting media (corbitbalsam).

Cryosection were fixed in methanol for 30 minutes at −80° C. and background decreased by adding $H_2O_2$ to the cold methanol to a final concentration of 10% and incubating for 30 minutes at RT. After 3 washes in Tris buffered saline (TBS, pH7.5), non-specific labeling was blocked by a 2 hour incubation of the slides in 10% BSA, 0.25% Triton X 100 in TBS as above and the same staining procedure as above was carried out.

Sections were examined with a Leica DMLB microscope and photographed using a Leica DC500 camera and Leica FireCam1.2.0 software.

Both human antibodies A and C labeled plaques of brains from AD disease patients (FIG. 6). Both diffuse and cored plaques were labeled. Moreover, diffuse plaques in non-demented pre-AD patients could also be detected by the A and C antibodies. Amyloid in cerebral amyloid angiopathy (CAA) was labeled with both antibodies and some staining of neurons which may correspond to intracellular amyloid was also detected. No labeling was seen on control brains from healthy patient. Plaques could be detected on paraffin sections pretreated with formic acid but no plaques were labeled on paraffin sections without formic acid pretreatment and on cryosections fixed in methanol. The human antibody B did not detect plaques on paraffin sections and the mouse antibody did not stain either paraffin or cryosections of human brains.

Abbreviations:
A=binding chimeric antibody AF (IgG4) (mC2ChVHAF)
B=non-binding chimeric antibody B (IgG4) (mC2VHB)
C=binding humanized antibody H4K1 (IgG4) (HuVH4/HuVK1)
Mouse=ACI-01-Ab-C2 mouse antibody (IgG2b)

Example 12

Functionality of mC2 on Amyloid Fibers 12.1 Modification of Conformation of Aâ1-42 Fibers and Initiation of Disaggregation after Binding of the mC2 Antibody In order to evaluate the mechanism by which the antibody is capable to disaggregate preformed beta-amyloid ($A\beta_{1-42}$) fibers a head-to-head comparison of Thioflavin-T (Th-T) fluorescent assay was performed measuring disaggregation and solid-state Nuclear Magnetic Resonance (NMR) of U-$^{13}$C Tyrosine10 and Valine12-labeled Aβ1-42 peptide analysing secondary conformation (FIG. 7A). The mC2 antibody solubilised 35.4% of the preformed Aβ1-42 fibers and simultaneously induced a shift in secondary conformation from beta sheet to random coiled. The reduction in the population of the beta sheet conformation with respect to the random coil is of the order of 35% and is therefore in close agreement with that measured using fluorescence Th-T assay (FIG. 7B). These data indicate that the binding of the mC2 antibody initiates a transition of the secondary structure which potentially causes a destabilization of the parallel intermolecular arrangement of the beta sheets affecting a break of elongated fibers into smaller fragments.

12.2 Conformation-Dependent Binding Affinity of mC2 Antibody

Since it is well known in the scientific literature that a proportion of the antibody-antigen binding energy can be used for energy-dependent modification of the conformation of an antigen (Blond and Goldberg, 1987), a comparison experiment of the binding affinity of the C2 antibody to the whole $A\beta_{1-42}$ protein and to a smaller, nine amino acid long, peptide comprising the antibody's epitope was performed (FIG. 8). For this comparison the affinities of the humanized antibody C2 were analyzed by ELISA using biotinylated peptides covering the complete amino-acid sequence of the C2's epitope (produced by Mimotopes and purchased from ANAWA Trading SA) and a biotinylated complete Aβ1-42 peptide (Bachem). The analysis was done according to the manufacturer's (Mimotopes) instructions. As demonstrated in FIG. 8 and Table 2, the antibody binds with a 36.0% higher affinity to the peptide comprising its specific epitope (aminoacids 13-21 of the $A\beta_{1-42}$ sequence) than to the whole $A\beta 1$-42 protein. It is therefore suggested that the difference in binding affinity energy was used for the energy-consuming transition of the secondary conformation of the amyloid protein to present the antigen in a more acceptable position for the antibody interaction. This explains why the affinity of the antibody is lower for the native (the whole amyloid protein) than for the isolated subunit.

TABLE 2

|  | O.D | |
| --- | --- | --- |
|  | Amyloid beta 13-21 | Amyloid beta 1-42 |
| hC2 | 1.225 | 0.9005 |
| Control IgG | 0.171 | 0.196 |

Example 13

Effects of the Anti-Amyloid hC2 on the Aggregation of Amyloid Beta 1-42 Peptide

To evaluate the ability of the humanized anti-human amyloid beta monoclonal antibody hC2 to mediate anti-aggregating and disaggregating effects on amyloid beta (Aβ) a thioflavin T spectrofluorescence assay was accomplished.

13.1 Inhibition of Aggregation Assay

Aβ1-42 lyophilized powder was reconstituted in hexafluoroisopropanol (HFIP) to 1 mM. The peptide solution was sonicated for 15 min at room temperature, agitated overnight, and aliquots made into non-siliconized microcentrifuge tubes. The HFIP was then evaporated under a stream of argon. The resulting peptide film was vacuum dried for 10 min and stored at −80° C. until used.

To assay for the antibody-mediated inhibition of Aβ1-42 aggregation the hC2 antibody was pre-diluted in PBS and an assay solution containing the following components was made in a non-siliconized incubation tube: 3.3 or 0.33 μM pre-diluted antibody, 10 μM thioflavin T, 33 μM Aβ1-42, and 8.2% DMSO. Therefore the final molar ratios of antibody to Aβ1-42 were 1:10 and 1:100. Appropriate control solutions were also prepared. The solutions were then incubated for 24 hrs at 37° C., and the spectrofluorescence (relative fluorescence units; RFU) read in six replicates in black 384-well plates (Perkin-Elmer) on a Perkin-Elmer FluoroCount spectrofluorometer. The spectrofluorescence was then measured and % disaggregation calculated as described below.

13.2 Disaggregation Assay

To assay for antibody-mediated disaggregation of pre-aggregated Aβ1-42, a low-molecular weight Aβ1-42, prepared as described above, was made up as a 110 μM solution in 27% DMSO and 1×PBS. This solution was then allowed to aggregate at 37° C. for 24 hrs after which the following were added: 3.3 or 0.33 μM pre-diluted antibody, and 10 μM thioflavin T. This resulted in a molar ratio of 1:10 and 1:100 antibody to Aβ1-42. This solution was then incubated for additional 24 hrs at 37° C. The spectrofluorescence was then measured and % disaggregation calculated as described below.

13.3 Calculation

Inhibition of aggregation or disaggregation is expressed as mean % inhibition or disaggregation, respectively, ±standard error of the mean (SEM) according to the following equation:

$$\% \text{ inhibition} = \frac{(RFU \text{ of } pos \text{ } contrl - RFU \text{ of } neg \text{ } contrl) - (RFU \text{ of sample with } A\beta 1 - 42 - RFU \text{ of sample without } A\beta 1 - 42)}{(RFU \text{ of } pos \text{ } contrl - RFU \text{ of } neg \text{ } contrl)} \times 100\%$$

13.4 Result 13.4.1 Inhibition of Aβ1-42 Aggregation

Inhibition of Aβ1-42 aggregation using the hC2 antibody is shown in Table 3 and FIG. 11. At an antibody to Aβ1-42 molar ratio of 1:100 the inhibition averaged 30% (2 independent experiments), whereas at a 1:10 molar ratio the inhibition was 80% (2 independent experiments; see Table 3).

TABLE 3 hC2-mediated inhibition of Aβ1-42 aggregation at a 1:100 and 1:10 antibody to Aβ1-42 molar ratios.

|  | Molar ratio (antibody to Aβ1-42) | |
| --- | --- | --- |
| Antibody | 1:100 | 1:10 |
| hC2 | 30.0 ± 4.1% | 80.4 ± 6.9% |

13.4.2 Disaggregation of Pre-Aggregated Aβ1-42

Disaggregation of pre-aggregated Aβ1-42 using the hC2 antibody is shown in Table 4 and FIG. 12. At an antibody to Aβ1-42 molar ratio of 1:100 the disaggregation averaged 24%, whereas at a 1:10 molar ratio the disaggregation was 32% (3 independent experiments; see Table 4).

TABLE 4 hC2-mediated disaggregation of pre-aggregated Ab1-42 at a 1:100 and 1:10 antibody to Aβ1-42 molar ratios.

|  | Molar ratio (antibody to Aβ1-42) | |
| --- | --- | --- |
| Antibody | 1:100 | 1:10 |
| hC2 | 23.9 ± 4.4% | 31.9 ± 3.5% |

Using the thioflavin T assay, the bi-functional properties of the anti-Aβ humanized antibody hC2 can be demonstrated, namely to inhibit the aggregation of Aβ1-42 into pathogenic protofibrillar conformation and in addition to disaggregate preformed Aβ1-42 protofibrils. hC2 inhibited Aβ1-42 aggregation by 80% at an antibody to Aβ1-42 molar ratio of 1:10. The ability of hC2 to disaggregate pre-aggregated protofibrils of Aβ1-42 at a 1:10 molar ratio was shown to be 32%.

Example 14

Conformation-Specific Binding of mC2 to Different Classes of Amyloid Protein

In order to evaluate the specificity of mC2 to different stages of polymerized amyloid protein, monomeric, polymeric soluble and fibrillic amyloid, an ELISA coated with these different stages of polymeric beta-amyloid was performed (FIG. 9). Monomers were prepared according to a modified method published by (Klein, 2002), soluble polymeric amyloid beta according to (Barghorn et al., 2005), whereas fibers were performed by incubation of amyloid (Bachem, Switzerland) with a final concentration of 1 μg/μl in Tris/HCl pH 7.4 at 37° C. for 5 days followed by a centrifugation step (10,000 rpm for 5 minutes). Then amyloid polymers were coated on an ELISA plates with a final concentration of 55 μg/ml and binding affinity ELISA by using an anti-mouse IgG monoclonal antibody (Jackson) labelled with alkaline phosphate was performed. As demonstrated in Table 5 the mC2 antibody binds with higher affinity to soluble polymeric amyloid beta than to fibers and with the lowest to monomers. These data indicate that the antibody's binding is influenced by the amyloid epitope and by the conformation of the different amyloid aggregates.

TABLE 5

Conformation-specific binding of mC2 to Amyloid Monomers, Oligomers and Fibres

| mC2 Ab Conc | O.D | | |
|---|---|---|---|
| (ug/ml) | Oligomer | Fibers | Monomers |
| 0.625 | 2.806 | 1.620 | 1.155 |
| 0.312 | 1.724 | 0.989 | 0.649 |
| 0.156 | 1.036 | 0.631 | 0.397 |
| 0.078 | 0.652 | 0.499 | 0.333 |

Example 15

Epitope Mapping of AC Immune's Monoclonal Antibody hC2

Epitope mapping of the humanized monoclonal antibody hC2 was performed by ELISA using three different peptide libraries. One library comprised a total of 33 biotinylated peptides covering the complete amino acid (aa) sequence of Aβ1-42 (produced by Mimotopes and purchased from ANAWA Trading SA), the second library contains biotinylated peptides using peptide 12 (aa12-20 of Aβ) from the first peptide library and substituting each aa in the sequence by an alanine (see table 8 below), and the third library contains biotinylated peptides 13, 14, or 15 (aa 13-21, 14-22 or 15-23 of Aβ) and substituting in each case the last amino acids to an alanine or to a glycine for aa 21 which is already an alanine (see table 9 below). A biotinylated complete Aβ1-42 peptide was used as positive control (Bachem). Epitope mapping was done according to the manufacturer's (Mimotopes) instructions. Briefly, Streptavidin coated plates (NUNC) were blocked with 0.1% BSA in PBS overnight at 4° C. After washing with PBS-0.05% Tween 20, plates were coated for 1 hour at RT with the different peptides from the library, diluted in 0.1% BSA, 0.1% Sodium Azide in PBS to a final concentration of 10 μM. After washing, plates were incubated for 1 hour at RT with the hC2 antibody or a non Aβ binding chimeric IgG4 antibody diluted to 200 ng/ml in 2% BSA, 0.1% Sodium Azide in PBS. Plates were washed again and incubated with alkaline phosphatase conjugated goat anti human IgG for 1 h at RT. After final washing, plates were incubated with phosphatase substrate (pNPP) and read at 405 nm using an ELISA plate reader.

It was shown that the humanized monoclonal antibody hC2 bound specifically to peptides 12, 13, 14, 15 and 16 of the first peptide library. These peptides comprise aa 12-20, 13-21, 14-22, 15-23 and 16-24 respectively of Aβ1-42, suggesting that the epitope lies in region 12-24 of Aβ. A second library with alanine substitutions was used to determine the critical aa for binding to Aβ12-20 (VHHQKLVFF)(SEQ ID NO: 42). The binding of the hC2 antibody is lost completely when amino acids 16, 17, 19 or 20 are substituted by an alanine, indicating that these aa are absolutely critical for binding of the antibody to Aβ. The binding of the hC2 antibody is partially lost when aa 15 and 18 are substituted.

The binding was also almost completely lost when aa 14 was substituted for an alanine, indicating that aa 14 is also very important for binding.

Finally, a third library was used to determine whether aa 21, 22 or 23 are critical for binding to the epitope. The binding of the antibody to aa 15-23 was reduced when aa 23 was substituted for an alanine, indicating that aa 23 is also important for binding. The binding was partially lost when aa 21 was substituted for a glycine and slightly lost when aa 22 was substituted for an alanine.

Example 16

Neuroprotection by the hC2 Antibody

The ability of antibody hC2 to protect neurons from Abeta oligomer-induced degeneration was assessed in an in vitro assay. Embryonic day 16.5-17.5 mouse cortical neurons were isolated, dissociated, and cultured in vitro in N3-F12 media. The cells were grown for nine days in total, and were fed on day 3 and on the day that Abeta oligomer, or Abeta oligomer plus anti-Abeta antibody hC2 was added. At day five ("4 days Abeta") or day six ("3 days Abeta"), certain wells of cells were treated with either 2 μM Abeta oligomer alone, or a combination of 2 μM Abeta oligomer and 50 μg/mL anti-Abeta antibody hC2.

The Abeta oligomer was prepared by dissolving Abeta 1-42 (rPeptide) in HFIP, from which Abeta peptides were aliquoted into 10 μl aliquots at 1 mg/ml and then evaporated in a fume hood for 30 minutes and peptide films were stored at −80 C until use. Upon use, the peptide film was dissolved in 10 μl of DMSO, then 78.6 μl of HAMS F12, and the Abeta peptide solution was incubated at 4 C for 24-48 hours (25 μM final concentration of Abeta).

For control cells, DMSO-F12 alone was added at the same volume as Abeta-DMSO at day 5, and the cells were cultured for an additional 4 days without any additional treatment. On day 9, neurons from all culture conditions were fixed and stained with Tuj1 (an anti-beta-tubulin antibody), followed by staining with secondary antibodies labeled with FITC to visualize microtubules, and thus neuronal processes in general. The results are shown in FIG. 13.

Untreated mouse embryonic cortical neurons showed normal morphology after nine days of culture (FIG. 13, leftmost panel). Treatment of the cells with Abeta oligomer for three days induced axon degeneration and caused a decrease in the total number of axons (FIG. 13, lower center panel), and this effect was even more pronounced at four days of treatment (FIG. 13, upper center panel). In contrast, the cells treated with the combination of Abeta oligomer and anti-Abeta antibody hC2 looked similar to control cells (FIG. 13, upper and lower right panels). These results indicate that anti-Abeta antibody hC2 was able to protect embryonic mouse cortical neurons from Abeta oligomer-induced degeneration.

TABLE 6

Positions and changes made in the humanized C2 light chain framework regions

| Position Light chain | 45 | 87 | 50 | 53 |
|---|---|---|---|---|
| Mouse C2V$_K$ | K | F | K | N |
| Humanized C2HuV$_K$1 | Q | Y | K | N |
| Humanized C2HuV$_K$2 | Q | F | K | N |
| Humanized C2HuV$_K$3 | K | Y | K | N |
| Humanized C2HuV$_K$4 | K | F | K | N |
| Human Germline dpk15 | Q | Y | L | N |
| Mouse C2V$_K$-R | | | R | |
| Mouse C2V$_K$-S | | | | S |

TABLE 7

Positions and changes made in the humanized C2 heavy chain framework regions

| Position Heavy chain | 47 | 94 |
|---|---|---|
| Mouse C2VHAF | L | S |
| Humanized C2HuVHAF1 | W | R |
| Humanized C2HuVHAF2 | W | S |
| Humanized C2HuVHAF3 | L | R |
| Humanized C2HuVHAF4 | L | S |
| Human Germline DP-54 | W | R |

A total of 8 different antibodies were constructed with light chains Humanized C2HuV$_K$1, C2HuV$_K$2, C2HuV$_K$3, C2HuV$_K$4 and heavy chains C2HuVHAF4 and C2HuVHAF2.

TABLE 8

Summary of peptides used in the second library aa that are important for binding are marked in italics and underscore and aa absolutely critical for binding are marked in italics and bold (SEQ ID NOS 42-51 respectively in order of appearance).

| | | | | | | | | |
|---|---|---|---|---|---|---|---|---|
| p12-20 | V | H | H | Q | K | L | V | F | F |
| A12 | A | H | H | Q | K | L | V | F | F |
| A13 | V | A | H | Q | K | L | V | F | F |
| A14 | V | H | A | Q | K | L | V | F | F |
| A15 | V | H | H | A | K | L | V | F | F |
| A16 | V | H | H | Q | A | L | V | F | F |
| A17 | V | H | H | Q | K | A | V | F | F |
| A18 | V | H | H | Q | K | L | A | F | F |
| A19 | V | H | H | Q | K | L | V | A | F |
| A20 | V | H | H | Q | K | L | V | F | A |
| aa no. | 12 | 13 | 14 | *15* | 16 | 17 | *18* | 19 | 20 |

TABLE 9

Summary of peptides used in the third library. aa that are important for binding are marked in italics and underscore and aa absolutely critical for binding are marked in italics and bold (SEQ ID NOS 52-57 respectively in order of appearance)

| | | | | | | | | | | |
|---|---|---|---|---|---|---|---|---|---|---|
| p13-21 | H | H | Q | K | L | V | F | F | A | |
| p13-21 G21 | H | H | Q | K | L | V | F | F | G | |
| p14-22 | | H | Q | K | L | V | F | A | E | |
| p14-22 A22 | | H | Q | K | L | V | F | A | A | |
| p15-23 | | | Q | K | L | V | F | A | E | D |
| p15-23 A23 | | | Q | K | L | V | F | A | E | A |
| aa no. | 13 | *14* | *15* | 16 | 17 | *18* | 19 | 20 | 21 | 22 | *23* |

The invention claimed is:

1. A method for treating or alleviating the effects of a disease or disorder associated with amyloid plaque formation, said method comprising administering to an animal or a human in need thereof an antibody or a fragment thereof capable of specifically binding beta-amyloid peptide, wherein said antibody or fragment thereof comprises:
 (i) human- or primate-derived framework regions,
 (ii) a Heavy Chain Variable Region (HCVR) CDR1 having the amino acid sequence of SEQ ID NO: 1,
 (iii) an HCVR CDR2 having the amino acid sequence of SEQ ID NO: 2,
 (iv) an HCVR CDR3 having the amino acid sequence of SEQ ID NO: 3, and
 (v) a Light Chain Variable Region (LCVR) comprising an amino acid sequence that is at least 98% identical to the amino acid sequence of SEQ ID NO: 12, wherein the LCVR comprises an LCVR CDR2 having the amino acid sequence of SEQ ID NO: 5 or the amino acid sequence of SEQ ID NO: 5 with one amino acid substitution; and
wherein at least one of the effects of the disease or disorder associated with amyloid plaque formation is treated or alleviated.

2. A method for treating or alleviating the effects of a disease or disorder associated with amyloid plaque formation, said method comprising administering a composition to an animal or a human in need thereof, wherein said composition comprises a therapeutically effective amount of an antibody or fragment thereof capable of specifically binding beta-amyloid peptide, and wherein said antibody or fragment thereof comprises:
 (i) human- or primate-derived framework regions,
 (ii) an HCVR CDR1 having the amino acid sequence of SEQ ID NO: 1,
 (iii) an HCVR CDR2 having the amino acid sequence of SEQ ID NO: 2,
 (iv) an HCVR CDR3 having the amino acid sequence of SEQ ID NO: 3, and
 (v) a Light Chain Variable Region (LCVR) comprising an amino acid sequence that is at least 98% identical to the amino acid sequence of SEQ ID NO: 12, wherein the LCVR comprises an LCVR CDR2 having the amino acid sequence of SEQ ID NO: 5 or the amino acid sequence of SEQ ID NO: 5 with one amino acid substitution in a therapeutically effective amount.

3. The method of claim 1 or 2, wherein the disease or disorder is Alzheimer's Disease.

4. The method of claim 1 or 2, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, ALS (amyotrophic lateral sclerosis), Adult Onset Diabetes, senile cardiac amyloidosis, endocrine tumors, or macular degeneration.

5. A method for treating or alleviating the effects of a disease or disorder associated with amyloid plaque formation, said method comprising administering to an animal or a human in need thereof an antibody or a fragment thereof capable of specifically binding beta-amyloid peptide, wherein said antibody or fragment thereof comprises:
 (i) human- or primate-derived framework regions,
 (ii) a Light Chain Variable Region (LCVR) CDR1 having the amino acid sequence of SEQ ID NO: 4,
 (iii) an LCVR CDR2 having the amino acid sequence of SEQ ID NO: 5 or the amino acid sequence of SEQ ID NO: 5 with one amino acid substitution,
 (iv) an LCVR CDR3 having the amino acid sequence of SEQ ID NO: 6, and
 (v) an HCVR comprising an amino acid sequence that is at least 98% identical to the amino acid sequence of SEQ ID NO: 15; and
wherein at least one of the effects of the disease or disorder associated with amyloid plaque formation is treated or alleviated.

6. A method for treating or alleviating the effects of a disease or disorder associated with amyloid plaque formation, said method comprising administering to an animal or a human in need thereof a composition comprising a therapeutically effective amount of an antibody or fragment thereof capable of specifically binding beta-amyloid peptide, wherein said antibody or fragment thereof comprises:
 (i) human- or primate-derived framework regions,
 (ii) a Light Chain Variable Region (LCVR) CDR1 having the amino acid sequence of SEQ ID NO: 4,
 (iii) an LCVR CDR2 having the amino acid sequence of SEQ ID NO: 5 or the amino acid sequence of SEQ ID NO: 5 with one amino acid substitution,
 (iv) an LCVR CDR3 having the amino acid sequence of SEQ ID NO: 6, and
 (v) an HCVR comprising an amino acid sequence that is at least 98% identical to the amino acid sequence of SEQ ID NO: 15.

7. The method of claim 5 or 6, wherein the disease or disorder is Alzheimer's Disease.

8. The method of claim 5 or 6, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, ALS (amyotrophic lateral sclerosis), Adult Onset Diabetes, senile cardiac amyloidosis, endocrine tumors, or macular degeneration.

9. The method of claim 2 or 6, wherein the framework regions comprise human germline VK sequences of Kabat subgroup VKII.

10. The method of claim 2 or 6, wherein the framework regions comprise human germline VH sequences of Kabat subgroup VHIII.

11. A method for treating or alleviating the effects of a disease or disorder associated with amyloid plaque formation, said method comprising administering to an animal or a human in need thereof an antibody or a fragment thereof capable of specifically binding beta-amyloid peptide, wherein said antibody or fragment thereof comprises:
 (i) human- or primate-derived framework regions;
 (ii) an HCVR comprising an HCVR CDR1 having the amino acid sequence of SEQ ID NO: 1,
 an HCVR CDR2 having the amino acid sequence of SEQ ID NO: 2, and
 an HCVR CDR3 having the amino acid sequence of SEQ ID NO: 3, wherein said HCVR comprises an amino acid sequence that is at least 98% identical to the amino acid sequence of SEQ ID NO: 15; and
 (iii) an LCVR comprising an LCVR CDR1 having the amino acid sequence of SEQ ID NO: 4,
 an LCVR CDR2 having the amino acid sequence of SEQ ID NO: 5 or the amino acid sequence of SEQ ID NO: 5 with one amino acid substitution, and
 an LCVR CDR3 having the amino acid sequence of SEQ ID NO: 6, wherein said LCVR comprises an amino acid sequence that is at least 98% identical to the amino acid sequence of SEQ ID NO: 12; and wherein at least one of the effects of the disease or disorder associated with amyloid plaque formation is treated or alleviated.

12. A method for treating or alleviating the effects of a disease or disorder associated with amyloid plaque formation, said method comprising administering to an animal or a human in need thereof a composition comprising a therapeutically effective amount of an antibody or fragment thereof capable of specifically binding beta-amyloid peptide, wherein said antibody or fragment thereof comprises:
(i) human- or primate-derived framework regions;
(ii) an HCVR comprising an HCVR CDR1 having the amino acid sequence of SEQ ID NO: 1,
an HCVR CDR2 having the amino acid sequence of SEQ ID NO: 2, and
an HCVR CDR3 having the amino acid sequence of SEQ ID NO: 3, wherein said HCVR comprises an amino acid sequence that is at least 98% identical to the amino acid sequence of SEQ ID NO: 15; and
(iii) an LCVR comprising an LCVR CDR1 having the amino acid sequence of SEQ ID NO: 4,
an LCVR CDR2 having the amino acid sequence of SEQ ID NO: 5 or the amino acid sequence of SEQ ID NO: 5 with one amino acid substitution, and
an LCVR CDR3 having the amino acid sequence of SEQ ID NO: 6, wherein said LCVR comprises an amino acid sequence that is at least 98% identical to the amino acid sequence of SEQ ID NO: 12.

13. The method of claim 11 or 12, wherein the disease or disorder is Alzheimer's Disease.

14. The method of claim 11 or 12, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, ALS (amyotrophic lateral sclerosis), Adult Onset Diabetes, senile cardiac amyloidosis, endocrine tumors, or macular degeneration.

15. The method according to claim 11 or 12, wherein the HCVR has the amino acid sequence of SEQ ID NO: 15.

16. The method according to claim 11 or 12, wherein the LCVR has the amino acid sequence of SEQ ID NO: 12.

17. The method of claim 11 or 12, wherein the CDR2 of the LCVR has the amino acid sequence of SEQ ID NO:5, SEQ ID NO:40, or SEQ ID NO:41.

18. The method of claim 11 or 12, wherein the CDR2 of the LCVR has the amino acid sequence of SEQ ID NO:5.

19. The method of claim 11 or 12, wherein the amino acid substitution is a conservative amino acid substitution.

20. The method of claim 11 or 12, wherein said antibody or fragment thereof comprises the humanized light chain of SEQ ID NO: 13 and the humanized heavy chain of SEQ ID NO: 16.

21. The method of claim 1, 2, 5, 6, 11 or 12, wherein said antibody or fragment thereof comprises the humanized light chain of SEQ ID NO: 13.

22. The method of claim 1, 2, 5, 6, 11 or 12, wherein said antibody or fragment thereof comprises the humanized heavy chain of SEQ ID NO: 16.

23. The method of claim 22, wherein the C-terminal Lys of the heavy chain constant region has been removed.

24. The method according to claim 1, 2, 5, 6, 11 or 12, wherein said antibody or fragment thereof is of the IgG4 isotype.

25. The method of claim 1, 5, or 11, wherein said antibody or fragment thereof binds to a beta-amyloid monomer with a binding affinity of at least about $1 \times 10^{-8}$ M to at least about $1 \times 10^{-11}$ M.

26. The method of claim 1, 5, or 11, wherein said antibody or fragment thereof binds to a beta-amyloid fiber, fibril or filament with a binding affinity of at least about $1 \times 10^{-9}$ M to at least about $1 \times 10^{-10}$ M.

27. A method for the preparation of a composition for use in treating or alleviating the effects of a disease or disorder associated with amyloid plaque formation, comprising formulating an antibody or a fragment thereof in a pharmaceutically acceptable form, wherein said antibody or fragment thereof is capable of specifically binding beta-amyloid peptide, and wherein said antibody or fragment thereof comprises:
(i) human- or primate-derived framework regions,
(ii) an HCVR CDR1 having the amino acid sequence of SEQ ID NO: 1,
(iii) an HCVR CDR2 having the amino acid sequence of SEQ ID NO: 2,
(iv) an HCVR CDR3 having the amino acid sequence of SEQ ID NO: 3, and
(v) a Light Chain Variable Region (LCVR) comprising an amino acid sequence that is at least 98% identical to the amino acid sequence of SEQ ID NO: 12, wherein the LCVR comprises an LCVR CDR2 having the amino acid sequence of SEQ ID NO: 5 or the amino acid sequence of SEQ ID NO: 5 with one amino acid substitution.

28. A method for the preparation of a composition for use in treating or alleviating the effects of a disease or disorder associated with amyloid plaque formation, comprising formulating an antibody or a fragment thereof in a pharmaceutically acceptable form, wherein said antibody or fragment thereof comprises:
(i) an HCVR having the amino acid sequence of SEQ ID NO: 15, and
(ii) an LCVR having the amino acid sequence of SEQ ID NO: 12.

29. A method for disaggregating preformed beta-amyloid fibers, comprising interacting an antibody or fragment thereof with preformed beta-amyloid fibers, wherein said antibody or fragment thereof is capable of specifically binding beta-amyloid peptide, and wherein said antibody or fragment thereof comprises:
(i) human- or primate-derived framework regions,
(ii) an HCVR CDR1 having the amino acid sequence of SEQ ID NO: 1,
(iii) an HCVR CDR2 having the amino acid sequence of SEQ ID NO: 2,
(iv) an HCVR CDR3 having the amino acid sequence of SEQ ID NO: 3, and
(v) a Light Chain Variable Region (LCVR) comprising an amino acid sequence that is at least 98% identical to the amino acid sequence of SEQ ID NO: 12, wherein the LCVR comprises an LCVR CDR2 having the amino acid sequence of SEQ ID NO: 5 or the amino acid sequence of SEQ ID NO: 5 with one amino acid substitution.

30. A method for disaggregating preformed beta-amyloid fibers, comprising interacting an antibody or fragment thereof with preformed beta-amyloid fibers, wherein said antibody or fragment thereof is capable of specifically binding beta-amyloid peptide, and wherein said antibody or fragment thereof comprises:

(i) an HCVR having the amino acid sequence of SEQ ID NO: 15, and
(ii) an LCVR having the amino acid sequence of SEQ ID NO: 12.

31. A method for treating or alleviating the effects of a disease or disorder associated with amyloid plaque formation, said method comprising administering to an animal or a human in need thereof a therapeutically effective amount of an antibody or a fragment thereof capable of specifically binding beta-amyloid peptide, wherein said antibody or fragment thereof comprises an HCVR having the amino acid sequence of SEQ ID NO: 15.

32. The method of claim 31, wherein the disease or disorder is Alzheimer's Disease.

33. The method of claim 31, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, ALS (amyotrophic lateral sclerosis), Adult Onset Diabetes, senile cardiac amyloidosis, endocrine tumors, or macular degeneration.

34. A method for treating or alleviating the effects of a disease or disorder associated with amyloid plaque formation, said method comprising administering to an animal or a human in need thereof a therapeutically effective amount of an antibody or a fragment thereof capable of specifically binding beta-amyloid peptide, wherein said antibody or fragment thereof comprises an LCVR having the amino acid sequence of SEQ ID NO: 12.

35. The method of claim 34, wherein the disease or disorder is Alzheimer's Disease.

36. The method of claim 34, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, ALS (amyotrophic lateral sclerosis), Adult Onset Diabetes, senile cardiac amyloidosis, endocrine tumors, or macular degeneration.

37. A method for treating or alleviating the effects of a disease or disorder associated with amyloid plaque formation, said method comprising administering to an animal or a human in need thereof a therapeutically effective amount of an antibody or a fragment thereof capable of specifically binding beta-amyloid peptide, wherein said antibody or a fragment thereof comprises:
(i) an HCVR having the amino acid sequence of SEQ ID NO: 15, and
(ii) an LCVR having the amino acid sequence of SEQ ID NO: 12.

38. The method of claim 37, wherein the disease or disorder is Alzheimer's Disease.

39. The method of claim 37, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, ALS (amyotrophic lateral sclerosis), Adult Onset Diabetes, senile cardiac amyloidosis, endocrine tumors, or macular degeneration.

40. A method for treating or alleviating the effects of a disease or disorder associated with amyloid plaque formation in the brain, said method comprising administering to an animal or a human in need thereof an antibody or a fragment thereof capable of specifically binding beta-amyloid peptide, wherein said antibody or fragment thereof comprises:
(i) human- or primate-derived framework regions,
(ii) an HCVR CDR1 having the amino acid sequence of SEQ ID NO: 1,
(iii) an HCVR CDR2 having the amino acid sequence of SEQ ID NO: 2,
(iv) an HCVR CDR3 having the amino acid sequence of SEQ ID NO: 3, and
(v) an LCVR comprising an amino acid sequence that is at least 98% identical to the amino acid sequence of SEQ ID NO: 12, wherein the LCVR comprises an LCVR CDR2 having the amino acid sequence of SEQ ID NO: 5 or the amino acid sequence of SEQ ID NO: 5 with one amino acid substitution; and
wherein at least one of the effects of the disease or disorder associated with amyloid plaque formation in the brain is treated or alleviated.

41. A method for treating or alleviating the effects of a disease or disorder associated with amyloid plaque formation in the brain, said method comprising administering to an animal or a human in need thereof an antibody or a fragment thereof capable of specifically binding beta-amyloid peptide, wherein said antibody or fragment thereof comprises:
(i) human- or primate-derived framework regions,
(ii) an LCVR CDR1 having the amino acid sequence of SEQ ID NO: 4,
(iii) an LCVR CDR2 having the amino acid sequence of SEQ ID NO: 5 or the amino acid sequence of SEQ ID NO: 5 with one amino acid substitution,
(iv) an LCVR CDR3 having the amino acid sequence of SEQ ID NO: 6, and
(v) an HCVR comprising an amino acid sequence that is at least 98% identical to the amino acid sequence of SEQ ID NO: 15; and
wherein at least one of the effects of the disease or disorder associated with amyloid plaque formation in the brain is treated or alleviated.

42. The method of claim 40 or 41, wherein said antibody or fragment thereof comprises the humanized light chain of SEQ ID NO: 13 and the humanized heavy chain of SEQ ID NO: 16.

43. The method of claim 40 or 41, wherein said antibody or fragment thereof comprises an HCVR comprising the amino acid sequence of SEQ ID NO: 15 and an LCVR comprising the amino acid sequence of SEQ ID NO: 12.

44. The method of claim 40 or 41, wherein the C-terminal Lys of the heavy chain constant region has been removed.

45. The method of claim 40 or 41, wherein the CDR2 of the LCVR has the amino acid sequence of SEQ ID NO:40 or SEQ ID NO:41.

46. The method of claim 40 or 41, wherein the CDR2 of the LCVR has the amino acid sequence of SEQ ID NO:5.

47. The method of claim 40 or 41, wherein the disease or disorder is Alzheimer's Disease.

48. The method of claim 40 or 41, wherein the disease or disorder is Lewy body dementia, Down's syndrome, hereditary cerebral hemorrhage with amyloidosis (Dutch type), the Guam Parkinson-Dementia complex, progressive supranuclear palsy, multiple sclerosis, Creutzfeld Jacob disease, Parkinson's disease, HIV-related dementia, or ALS (amyotrophic lateral sclerosis).

49. The method of claim 37, 40, or 41, wherein said antibody or fragment thereof is of the IgG4 isotype.

50. A method for retaining or increasing cognitive memory capacity of an animal or a human suffering from memory impairment associated with a disease or disorder associated with brain amyloid plaque formation by administering to the animal or the human, a pharmaceutical composition comprising an antibody or a fragment thereof which is capable of specifically binding beta-amyloid peptide, and wherein said antibody or fragment thereof comprises:
  (i) an HCVR comprising an amino acid sequence that is at least 98% identical to the amino acid sequence of SEQ ID NO: 15, or
  (ii) an LCVR comprising an amino acid sequence that is at least 98% identical to the amino acid sequence of SEQ ID NO: 12, or
  (iii) an HCVR comprising an amino acid sequence that is at least 98% identical to the amino acid sequence of SEQ ID NO: 15 and an LCVR comprising an amino acid sequence that is at least 98% identical to the amino acid sequence of SEQ ID NO: 12.

51. A method for retaining or increasing cognitive memory capacity of an animal or a human suffering from memory impairment associated with a disease or disorder associated with brain amyloid plaque formation by administering to the animal or the human, a pharmaceutical composition comprising an antibody or a fragment thereof which is capable of specifically binding beta-amyloid peptide, and wherein said antibody or fragment thereof comprises:
  (i) an HCVR comprising the amino acid sequence of SEQ ID NO: 15, or
  (ii) an LCVR comprising the amino acid sequence of SEQ ID NO: 12 or
  (iii) an HCVR comprising the amino acid sequence of SEQ ID NO: 15 and an LCVR comprising the amino acid sequence of SEQ ID NO: 12.

52. A method for retaining or increasing cognitive memory capacity of an animal or a human suffering from memory impairment associated with a disease or disorder associated with brain amyloid plaque formation by administering to the animal or the human, a pharmaceutical composition comprising an antibody or a fragment thereof which is capable of specifically binding beta-amyloid peptide, and wherein said antibody or fragment thereof comprises:
  (i) an HCVR comprising the amino acid sequence of SEQ ID NO: 15, and
  (ii) an LCVR comprising the amino acid sequence of SEQ ID NO: 12.

53. A method for restoring the cognitive memory capacity of an animal or a human suffering from memory impairment associated with a disease or disorder associated with brain amyloid plaque formation by administering to the animal or the human, a pharmaceutical composition comprising an antibody or a fragment thereof which is capable of specifically binding beta-amyloid peptide, and wherein said antibody or fragment thereof comprises:
  (i) an HCVR comprising an amino acid sequence that is at least 98% identical to the amino acid sequence of SEQ ID NO: 15, or
  (ii) an LCVR comprising an amino acid sequence that is at least 98% identical to the amino acid sequence of SEQ ID NO: 12, or
  (iii) an HCVR comprising an amino acid sequence that is at least 98% identical to the amino acid sequence of SEQ ID NO: 15 and an LCVR comprising an amino acid sequence that is at least 98% identical to the amino acid sequence of SEQ ID NO: 12.

54. A method for restoring the cognitive memory capacity of an animal or a human suffering from memory impairment associated with a disease or disorder associated with brain amyloid plaque formation by administering to the animal or the human, a pharmaceutical composition comprising an antibody or a fragment thereof which is capable of specifically binding beta-amyloid peptide, and wherein said antibody or fragment thereof comprises:
  (i) an HCVR comprising the amino acid sequence of SEQ ID NO: 15, or
  (ii) an LCVR comprising the amino acid sequence of SEQ ID NO: 12 or
  (iii) an HCVR comprising the amino acid sequence of SEQ ID NO: 15 and an LCVR comprising the amino acid sequence of SEQ ID NO: 12.

55. A method for restoring the cognitive memory capacity of an animal or a human suffering from memory impairment associated with a disease or disorder associated with brain amyloid plaque formation by administering to the animal or the human, a pharmaceutical composition comprising an antibody or a fragment thereof which is capable of specifically binding beta-amyloid peptide, and wherein said antibody or fragment thereof comprises:
  (i) an HCVR comprising the amino acid sequence of SEQ ID NO: 15, and
  (ii) an LCVR comprising the amino acid sequence of SEQ ID NO: 12.

56. A method of protecting neurons from beta-amyloid induced neuron degradation comprising treating neurons with an effective amount of a humanized antibody or a fragment thereof which is capable of specifically binding beta-amyloid peptide, and wherein said humanized antibody or fragment thereof comprises:
  (i) an HCVR comprising the amino acid sequence of SEQ ID NO: 15 or an amino acid sequence that is at least 98% identical to the amino acid sequence of SEQ ID NO: 15, or
  (ii) an LCVR comprising the amino acid sequence of SEQ ID NO: 12 or an amino acid sequence that is at least 98% identical to the amino acid sequence of SEQ ID NO: 12, or
  (iii) an HCVR comprising an amino acid sequence that is at least 98% identical to the amino acid sequence of SEQ ID NO: 15 and an LCVR comprising an amino acid sequence that is at least 98% identical to the amino acid sequence of SEQ ID NO: 12, or
  (iv) an HCVR comprising the amino acid sequence of SEQ ID NO: 15 and an LCVR comprising the amino acid sequence of SEQ ID NO: 12.

57. A method of protecting neurons from beta-amyloid induced neuron degradation comprising treating neurons with an effective amount of a humanized antibody or a fragment thereof which is capable of specifically binding beta-amyloid peptide, and wherein said humanized antibody or fragment thereof comprises:
  (i) an HCVR comprising the amino acid sequence of SEQ ID NO: 15, and
  (ii) an LCVR comprising the amino acid sequence of SEQ ID NO: 12.

* * * * *

SEQUENCE LISTING

<160> NUMBER OF SEQ ID NOS: 80

<210> SEQ ID NO 1
<211> LENGTH: 10
<212> TYPE: PRT
<213> ORGANISM: Mus musculus

<400> SEQUENCE: 1

Gly Phe Thr Phe Ser Ser Tyr Gly Met Ser
1               5                   10

<210> SEQ ID NO 2
<211> LENGTH: 17
<212> TYPE: PRT
<213> ORGANISM: Mus musculus

<400> SEQUENCE: 2

Ser Ile Asn Ser Asn Gly Gly Ser Thr Tyr Tyr Pro Asp Ser Val Lys
1               5                   10                  15

Gly

<210> SEQ ID NO 3
<211> LENGTH: 3
<212> TYPE: PRT
<213> ORGANISM: Mus musculus

<400> SEQUENCE: 3

Gly Asp Tyr
1

<210> SEQ ID NO 4
<211> LENGTH: 16
<212> TYPE: PRT
<213> ORGANISM: Mus musculus

<400> SEQUENCE: 4

Arg Ser Ser Gln Ser Leu Val Tyr Ser Asn Gly Asp Thr Tyr Leu His
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Ser Gln Ser Thr His Val Pro Trp Thr
1               5

<210> SEQ ID NO 7
<211> LENGTH: 6
<212> TYPE: PRT
<213> ORGANISM: Homo sapiens

<400> SEQUENCE: 7

Val Phe Phe Ala Glu Asp
1               5

<210> SEQ ID NO 8
<211> LENGTH: 5
<212> TYPE: PRT
<213> ORGANISM: Homo sapiens

<400> SEQUENCE: 8

His Gln Lys Leu Val
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: Ala, Val, Leu, norleucine, Met, Phe or Ile
<220> FEATURE:

```
<221> NAME/KEY: MOD_RES
<222> LOCATION: (4)
<223> OTHER INFORMATION: Ala, Val, Leu, Ser or Ile
<220> FEATURE:
<221> NAME/KEY: MOD_RES
<222> LOCATION: (5)
<223> OTHER INFORMATION: Glu or Asp
<220> FEATURE:
<221> NAME/KEY: MOD_RES
<222> LOCATION: (6)
<223> OTHER INFORMATION: Glu or Asp

<400> SEQUENCE: 9

Xaa Phe Phe Xaa Xaa Xaa
 1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: His, Asn, Gln, Lys or Arg
<220> FEATURE:
<221> NAME/KEY: MOD_RES
<222> LOCATION: (2)
<223> OTHER INFORMATION: Asn or Gln
<220> FEATURE:
<221> NAME/KEY: MOD_RES
<222> LOCATION: (5)
<223> OTHER INFORMATION: Ala, Val, Leu, norleucine, Met, Phe or Ile

<400> SEQUENCE: 10

Xaa Xaa Lys Leu Xaa
 1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: His, Asn or Gln
<220> FEATURE:
<221> NAME/KEY: MOD_RES
<222> LOCATION: (2)
<223> OTHER INFORMATION: Asn or Gln
<220> FEATURE:
<221> NAME/KEY: MOD_RES
<222> LOCATION: (5)
<223> OTHER INFORMATION: Val, Leu or Ile
<220> FEATURE:
<221> NAME/KEY: MOD_RES
<222> LOCATION: (8)
<223> OTHER INFORMATION: Ala or Val
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Glu or Asp

<400> SEQUENCE: 11

Xaa Xaa Lys Leu Xaa Phe Phe Xaa Xaa Xaa
 1               5                  10
```

```
<210> SEQ ID NO 12
<211> LENGTH: 112
<212> TYPE: PRT
<213> ORGANISM: Artificial Sequence
<220> FEATURE:
<223> OTHER INFORMATION: Synthetic humanized C2 HuVK 1 variable light
      chain

<400> SEQUENCE: 12
```

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

```
<210> SEQ ID NO 13
<211> LENGTH: 219
<212> TYPE: PRT
<213> ORGANISM: Artificial Sequence
<220> FEATURE:
<223> OTHER INFORMATION: Synthetic humanized C2 light chain

<400> SEQUENCE: 13
```

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

```
Pro Val Thr Lys Ser Phe Asn Arg Gly Glu Cys
        210                 215
```

<210> SEQ ID NO 14
<211> LENGTH: 107
<212> TYPE: PRT
<213> ORGANISM: Artificial Sequence
<220> FEATURE:
<223> OTHER INFORMATION: Synthetic humanized C2 light chain constant
      region

<400> SEQUENCE: 14

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 15
<211> LENGTH: 112
<212> TYPE: PRT
<213> ORGANISM: Artificial Sequence
<220> FEATURE:
<223> OTHER INFORMATION: Synthetic humanized C2 HuVH AF 4 variable
      heavy chain

<400> SEQUENCE: 15

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110
```

<210> SEQ ID NO 16
<211> LENGTH: 439
<212> TYPE: PRT
<213> ORGANISM: Artificial Sequence
<220> FEATURE:
<223> OTHER INFORMATION: Synthetic humanized C2 heavy chain

<400> SEQUENCE: 16

```
Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly Lys
        435
```

<210> SEQ ID NO 17
<211> LENGTH: 326
<212> TYPE: PRT
<213> ORGANISM: Homo sapiens

<400> SEQUENCE: 17

```
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 18
<211> LENGTH: 51
<212> TYPE: DNA
<213> ORGANISM: Mus musculus

<400> SEQUENCE: 18

```
agcatcaata gtaatggtgg tagcacctat tatccagaca gtgtgaaggg c         51
```

```
<210> SEQ ID NO 19
<211> LENGTH: 9
<212> TYPE: DNA
<213> ORGANISM: Mus musculus

<400> SEQUENCE: 19 ggtgactac                                                        9
```

```
<210> SEQ ID NO 20
<211> LENGTH: 49
<212> TYPE: DNA
<213> ORGANISM: Mus musculus

<400> SEQUENCE: 20
agatctagtc agagccttgt atatagtaat ggagacacct atttacatt           49
```

```
<210> SEQ ID NO 21
<211> LENGTH: 336
<212> TYPE: DNA
<213> ORGANISM: Artificial Sequence
<220> FEATURE:
<223> OTHER INFORMATION: Synthetic humanized C2 Hu VK 1 variable light
      chain

<400> SEQUENCE: 21
gatattgtga tgacccaatc tccactctcc ctgcctgtca ctcctggtga gcctgcctcc   60
atctcttgca gatctagtca gagccttgta tatagtaatg gagacaccta tttacattgg  120
tacctgcaga agccaggcca gtctccacag ctcctgatct acaaagtttc caaccgattt  180
tctggggtcc cagacaggtt cagtggcagt ggatcaggga cagatttcac actcaagatc  240
agcagagtgg aggctgagga tgtgggagtt tattactgct ctcaaagtac acatgttcct  300
tggacgttcg gccaaggcac caaggtggaa atcaaa                            336
```

```
<210> SEQ ID NO 22
<211> LENGTH: 657
<212> TYPE: DNA
<213> ORGANISM: Artificial Sequence
<220> FEATURE:
<223> OTHER INFORMATION: Synthetic humanized C2 light chain

<400> SEQUENCE: 22
gatattgtga tgacccaatc tccactctcc ctgcctgtca ctcctggtga gcctgcctcc   60
atctcttgca gatctagtca gagccttgta tatagtaatg gagacaccta tttacattgg  120
tacctgcaga agccaggcca gtctccacag ctcctgatct acaaagtttc caaccgattt  180
tctggggtcc cagacaggtt cagtggcagt ggatcaggga cagatttcac actcaagatc  240
agcagagtgg aggctgagga tgtgggagtt tattactgct ctcaaagtac acatgttcct  300
tggacgttcg gccaaggcac caaggtggaa atcaaaagga ctgtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657
```

```
<210> SEQ ID NO 23
<211> LENGTH: 321
```

```
<212> TYPE: DNA
<213> ORGANISM: Artificial Sequence
<220> FEATURE:
<223> OTHER INFORMATION: Synthetic humanized C2 light chain constant
      region

<400> SEQUENCE: 23
aggactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 24
<211> LENGTH: 336
<212> TYPE: DNA
<213> ORGANISM: Artificial Sequence
<220> FEATURE:
<223> OTHER INFORMATION: Synthetic humanized C2 HuVH AF variable heavy
      chain

<400> SEQUENCE: 24
gaggtgcagc tggtcgagtc tgggggaggc ttagtgcagc ctggagggtc cctgagactc    60
tcctgtgcag cctctggatt cactttcagt agctatggca tgtcttgggt tcgccaggct   120
ccaggcaagg gtctcgaatt ggtcgcaagc atcaatagta tggtggtag  cacctattat   180 ccagacagtg tgaagggccg attcaccatc tccagagaca atgccaagaa ctccctgtac   240
ctgcaaatga acagtctgag agctgaggac accgccgtgt attactgtgc aagtggtgac   300
tactggggcc aaggcaccac tgtcacagtc tcctca                             336

<210> SEQ ID NO 25
<211> LENGTH: 1317
<212> TYPE: DNA
<213> ORGANISM: Artificial Sequence
<220> FEATURE:
<223> OTHER INFORMATION: Synthetic humanized C2 heavy chain

<400> SEQUENCE: 25
gaggtgcagc tggtcgagtc tgggggaggc ttagtgcagc ctggagggtc cctgagactc    60
tcctgtgcag cctctggatt cactttcagt agctatggca tgtcttgggt tcgccaggct   120
ccaggcaagg gtctcgaatt ggtcgcaagc atcaatagta tggtggtag  cacctattat   180 ccagacagtg tgaagggccg attcaccatc tccagagaca atgccaagaa ctccctgtac   240
ctgcaaatga acagtctgag agctgaggac accgccgtgt attactgtgc aagtggtgac   300
tactggggcc aaggcaccac tgtcacagtc tcctcagctt ccaccaaggg cccatccgtc   360
ttccccctgg cgccctgctc cagatcgacc tccgagagca gccgccct  gggctgcctg   420 gtcaaggact acttccccga accggtgacg gtgtcgtgga actcaggcgc cctgaccagc   480
ggcgtgcaca ccttcccggc tgtcctacag tcctcaggac tctactccct cagcagcgtg   540
gtgaccgtgc cctccagcag cttgggcacg aagacctaca cctgcaacgt agatcacaag   600
cccagcaaca ccaaggtgga caagagagtt gagtccaaat atggtccccc gtgtccccca   660
tgcccagcac ctgagttcct gggggaccca tcagtcttcc tgttcccccc aaaacccaag   720
gacactctca tgatctcccg gacccctgag gtcacgtgcg tggtggtgga cgtgagccaa   780 gaagacccg aggtccagtt caactggtac gtggatggcg tggaggtgca taatgccaag   840
```

```
acaaagccgc gggaggagca gttcaacagc acgtaccgtg tggtcagcgt cctcaccgtc      900
ctgcaccagg actggctgaa cggcaaggag tacaagtgca aggtctccaa caaaggcctc      960
ccgtcctcca tcgagaaaac catctccaaa gccaagggc agccccgaga gccacaggtg     1020
tacaccctgc ccccatccca ggaggagatg accaagaacc aggtcagcct gacctgcctg     1080
gtcaaaggct tctacccag cgacatcgcc gtggagtggg agagcaatgg gcagccggag      1140
aacaactaca agaccacgcc tcccgtcctc gattccgacg gctccttctt cctctacagc     1200
aggctaaccg tggacaagag caggtggcag gaggggaatg tcttctcatg ctccgtgatg     1260
catgaggctc tgcacaacca ctacacacag aagagcctct ccctgtctct gggtaaa       1317
```

<210> SEQ ID NO 26
<211> LENGTH: 981
<212> TYPE: DNA
<213> ORGANISM: Artificial Sequence
<220> FEATURE:
<223> OTHER INFORMATION: Synthetic humanized C2 heavy chain constant
      region

<400> SEQUENCE: 26

```
gcttccacca agggcccatc cgtcttcccc ctggcgccct gctccagatc gacctccgag       60
agcacagccg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacgaagacc      240
tacacctgca acgtagatca caagcccagc aacaccaagg tggacaagag agttgagtcc      300
aaatatggtc cccgtgtcc cccatgccca gcacctgagt tcctggggg accatcagtc       360 ttcctgttcc ccccaaaacc caaggacact ctcatgatct cccggacccc tgaggtcacg      420
tgcgtggtgg tggacgtgag ccaggaagac cccgaggtcc agttcaactg gtacgtggat      480
ggcgtggagg tgcataatgc caagacaaag ccgcgggagg agcagttcaa cagcacgtac      540
cgtgtggtca gcgtcctcac cgtcctgcac caggactggc tgaacggcaa ggagtacaag      600
tgcaaggtct ccaacaaagg cctcccgtc tccatcgaga aaaccatctc caaagccaaa      660
gggcagcccc gagagccaca ggtgtacacc ctgcccccat cccaggagga gatgaccaag      720
aaccaggtca gcctgacctg cctggtcaaa ggcttctacc ccagcgacat cgccgtggag      780
tgggagagca atgggcagcc ggagaacaac tacaagacca cgcctcccgt cctcgattcc      840
gacggctcct tcttcctcta cagcaggcta accgtggaca agagcaggtg gcaggagggg      900
aatgtcttct catgctccgt gatgcatgag gctctgcaca accactacac acagaagagc      960
ctctccctgt ctctgggtaa a                                                 981
```

<210> SEQ ID NO 27
<211> LENGTH: 112
<212> TYPE: PRT
<213> ORGANISM: Mus musculus

<400> SEQUENCE: 27

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
```

```
                50                   55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

<210> SEQ ID NO 28
<211> LENGTH: 112
<212> TYPE: PRT
<213> ORGANISM: Mus musculus

<400> SEQUENCE: 28

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Ser Tyr
             20                  25                  30

Gly Met Ser Trp Val Arg Gln Thr Pro Asp Lys Arg Leu Glu Leu Val
         35                  40                  45

Ala Ser Ile Asn Ser Asn Gly Gly Ser Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Ser Gly Asp Tyr Trp Gly Gln Gly Ser Thr Leu Thr Val Ser Ser
            100                 105                 110

<210> SEQ ID NO 29
<211> LENGTH: 336
<212> TYPE: DNA
<213> ORGANISM: Mus musculus

<400> SEQUENCE: 29
gatgttgtga tgacccaaac tccactctcc ctgcctgtca gtcttggaga tcaagcctcc      60
atctcttgca gatctagtca gagccttgta tatagtaatg agacacctat tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
tggacgttcg gtggaggcac caagctagaa atcaaa                              336

<210> SEQ ID NO 30
<211> LENGTH: 417
<212> TYPE: DNA
<213> ORGANISM: Mus musculus

<400> SEQUENCE: 30
atgaagttgc tgttaggct gttggtgctg atgttctgga ttcctgcttc cagcagtgat       60
gttgtgatga cccaaactcc actctccctg cctgtcagtc ttggagatca agcctccatc    120
tcttgcagat ctagtcagag ccttgtatat agtaatggag acacctattt acattggtac    180
ctgcagaagc caggccagtc tccaaagctc ctgatctaca agtttccaa ccgatttct     240 ggggtcccag acaggttcag tggcagtgga tcagggacag atttcacact caagatcagc    300
agagtggagg ctgaggatct gggagtttat ttctgctctc aaagtacaca tgttccttgg    360
```

```
acgttcggtg gaggcaccaa gctagaaatc aaacgggctg atgctgcacc aactgta          417
```

<210> SEQ ID NO 31
<211> LENGTH: 336
<212> TYPE: DNA
<213> ORGANISM: Mus musculus

<400> SEQUENCE: 31

```
gaggtgcagc tggtggagtc tgggggaggc ttagtgcagc ctggagggtc cctgaaactc          60
tcctgtgcag cctctggatt cactttcagt agctatggca tgtcttgggt tcgccagact         120
ccagacaaga ggctggaatt ggtcgcaagc atcaatagta atggtggtag cacctattat         180
ccagacagtg tgaagggccg attcaccatc tccagagaca atgccaagaa caccctgtac         240
ctgcaaatga gcagtctgaa gtctgaggac acagccatgt attactgtgc aagtggtgac         300
tactggggcc aaggctccac tctcacagtc tcctca                                   336
```

<210> SEQ ID NO 32
<211> LENGTH: 408
<212> TYPE: DNA
<213> ORGANISM: Mus musculus

<400> SEQUENCE: 32

```
atgrasttsg ggytcagmtt grttttcctt gcccttattt taaaaggtgt ccaatgtgag          60
gtgcagctgg tggagtctgg gggaggctta gtgcagcctg agggtccct gaaactctcc         120
tgtgcagcct ctggattcac tttcagtagc tatggcatgt cttgggttcg ccagactcca         180
gacaagaggc tggaattggt cgcaagcatc aatagtaatg gtggtagcac ctattatcca         240
gacagtgtga agggccgatt caccatctcc agagacaatg ccaagaacac cctgtacctg         300
caaatgagca gtctgaagtc tgaggacaca gccatgtatt actgtgcaag tggtgactac         360
tggggccaag gctccactct cacagtctcc tcagccaaaa caacaccc                      408
```

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Asn or Gln
<220> FEATURE:
<221> NAME/KEY: MOD_RES
<222> LOCATION: (5)
<223> OTHER INFORMATION: Ala, Val, Leu, norleucine, Met, Phe or Ile
<220> FEATURE:
<221> NAME/KEY: MOD_RES
<222> LOCATION: (8)
<223> OTHER INFORMATION: Ala, Val, Leu, Ser or Ile
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Glu or Asp

<400> SEQUENCE: 33

```
His Xaa Lys Leu Xaa Phe Phe Xaa Xaa Xaa
 1               5                  10
```

<210> SEQ ID NO 34
<211> LENGTH: 10

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: His, Asn, Gln, Lys or Arg
<220> FEATURE:
<221> NAME/KEY: MOD_RES
<222> LOCATION: (2)
<223> OTHER INFORMATION: Asn or Gln
<220> FEATURE:
<221> NAME/KEY: MOD_RES
<222> LOCATION: (5)
<223> OTHER INFORMATION: Val, Ala, Leu, Met, Phe, norleucine or Ile
<220> FEATURE:
<221> NAME/KEY: MOD_RES
<222> LOCATION: (8)
<223> OTHER INFORMATION: Ala, Val, Leu or Ile
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Glu or Asp

<400> SEQUENCE: 34

Xaa Xaa Lys Leu Xaa Phe Phe Xaa Xaa Xaa
 1               5                  10

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Phe Phe Ala Glu
 1

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: His, Asn, Gln, Lys or Arg
<220> FEATURE:
<221> NAME/KEY: MOD_RES
<222> LOCATION: (3)
<223> OTHER INFORMATION: Asn or Gln
<220> FEATURE:
<221> NAME/KEY: MOD_RES
<222> LOCATION: (6)
<223> OTHER INFORMATION: Ala, Val, Leu, norleucine, Met Phe or Ile
<220> FEATURE:
<221> NAME/KEY: MOD_RES
<222> LOCATION: (9)
<223> OTHER INFORMATION: Ala, Val, Leu, Ser or Ile
<220> FEATURE:
<221> NAME/KEY: MOD_RES
<222> LOCATION: (10)
<223> OTHER INFORMATION: Glu or Asp
<220> FEATURE:
<221> NAME/KEY: MOD_RES
<222> LOCATION: (12)
<223> OTHER INFORMATION: Ala, Val, Leu, norleucine, Met, Phe or Ile

<400> SEQUENCE: 36
```

```
Xaa His Xaa Lys Leu Xaa Phe Phe Xaa Xaa Asp Xaa
 1               5                  10
```

<210> SEQ ID NO 37
<211> LENGTH: 12
<212> TYPE: PRT
<213> ORGANISM: Artificial Sequence
<220> FEATURE:
<223> OTHER INFORMATION: Synthetic peptide

<400> SEQUENCE: 37

```
Val His His Gln Lys Leu Val Phe Phe Ala Glu Asp
 1               5                  10
```

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

```
Val His His Gln Lys Leu Val Phe Phe Ala Glu Asp Val Gly
 1               5                  10
```

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Asn or Gln
<220> FEATURE:
<221> NAME/KEY: MOD_RES
<222> LOCATION: (5)
<223> OTHER INFORMATION: Val, Leu or Ile
<220> FEATURE:
<221> NAME/KEY: MOD_RES
<222> LOCATION: (8)
<223> OTHER INFORMATION: Ala or Val
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Glu or Asp

<400> SEQUENCE: 39

```
His Xaa Lys Leu Xaa Phe Phe Xaa Xaa Xaa
 1               5                  10
```

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

```
Arg Val Ser Asn Arg Phe Ser
 1               5
```

<210> SEQ ID NO 41
<211> LENGTH: 7
<212> TYPE: PRT

<213> ORGANISM: Artificial Sequence
<220> FEATURE:
<223> OTHER INFORMATION: Synthetic peptide

<400> SEQUENCE: 41

Lys Val Ser Ser Arg Phe Ser
 1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Val His His Gln Lys Leu Val Phe Phe
 1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Ala His His Gln Lys Leu Val Phe Phe
 1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Val Ala His Gln Lys Leu Val Phe Phe
 1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Val His Ala Gln Lys Leu Val Phe Phe
 1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Val His His Ala Lys Leu Val Phe Phe
 1               5

<210> SEQ ID NO 47
<211> LENGTH: 9
<212> TYPE: PRT
<213> ORGANISM: Artificial Sequence
<220> FEATURE:

```
<223> OTHER INFORMATION: Synthetic peptide

<400> SEQUENCE: 47

Val His His Gln Ala Leu Val Phe Phe
  1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Val His His Gln Lys Ala Val Phe Phe
  1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Val His His Gln Lys Leu Ala Phe Phe
  1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Val His His Gln Lys Leu Val Ala Phe
  1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Val His His Gln Lys Leu Val Phe Ala
  1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

His His Gln Lys Leu Val Phe Phe Ala
  1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 53

His His Gln Lys Leu Val Phe Phe Gly
  1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

His Gln Lys Leu Val Phe Phe Ala Glu
  1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

His Gln Lys Leu Val Phe Phe Ala Ala
  1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Gln Lys Leu Val Phe Phe Ala Glu Asp
  1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Gln Lys Leu Val Phe Phe Ala Glu Ala
  1               5

<210> SEQ ID NO 58
<211> LENGTH: 635
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (122)..(166)
<220> FEATURE:
<221> NAME/KEY: CDS
<222> LOCATION: (249)..(596)

<400> SEQUENCE: 58
aagcttatga atatgcaaat cctctgaatc tacatggtaa atataggttt gtctatacca    60
caaacagaaa aacatgagat cacagttctc tctacagtta ctgagcacac aggacctcac   120 c atg gga tgg agc tgt atc atc ctc ttc ttg gta gca aca gct aca        166
  Met Gly Trp Ser Cys Ile Ile Leu Phe Leu Val Ala Thr Ala Thr
    1               5                  10                  15
```

```
ggtaagggc tcacagtagc aggcttgagg tctggacata tatatgggtg acaatgacat      226
ccactttgcc tttctctcca ca ggt gtc cac tcc gat gtt gtg atg acc caa     278
                         Gly Val His Ser Asp Val Val Met Thr Gln
                                     20                  25 act cca ctc tcc ctg cct gtc agt ctt gga gat caa gcc tcc atc tct     326
Thr Pro Leu Ser Leu Pro Val Ser Leu Gly Asp Gln Ala Ser Ile Ser
                30                  35                  40 tgc aga tct agt cag agc ctt gta tat agt aat gga gac acc tat tta     374
Cys Arg Ser Ser Gln Ser Leu Val Tyr Ser Asn Gly Asp Thr Tyr Leu
            45                  50                  55 cat tgg tac ctg cag aag cca ggc cag tct cca aag ctc ctg atc tac     422
His Trp Tyr Leu Gln Lys Pro Gly Gln Ser Pro Lys Leu Leu Ile Tyr
        60                  65                  70 aaa gtt tcc aac cga ttt tct ggg gtc cca gac agg ttc agt ggc agt     470
Lys Val Ser Asn Arg Phe Ser Gly Val Pro Asp Arg Phe Ser Gly Ser
    75                  80                  85 gga tca ggg aca gat ttc aca ctc aag atc agc aga gtg gag gct gag     518
Gly Ser Gly Thr Asp Phe Thr Leu Lys Ile Ser Arg Val Glu Ala Glu
90                  95                  100                 105 gat ctg gga gtt tat ttc tgc tct caa agt aca cat gtt cct tgg acg     566
Asp Leu Gly Val Tyr Phe Cys Ser Gln Ser Thr His Val Pro Trp Thr
                110                 115                 120 ttc ggc gga ggc acc aag ctg gaa atc aaa cgtgagtaga atttaaactt       616
Phe Gly Gly Gly Thr Lys Leu Glu Ile Lys
            125                 130 tgcttcctca gttggatcc                                                 635

<210> SEQ ID NO 59
<211> LENGTH: 131
<212> TYPE: PRT
<213> ORGANISM: Artificial Sequence
<220> FEATURE:
<223> OTHER INFORMATION: Synthetic construct

<400> SEQUENCE: 59

Met Gly Trp Ser Cys Ile Ile Leu Phe Leu Val Ala Thr Ala Thr Gly
1               5                   10                  15

Val His Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val Tyr Ser Asn Gly Asp Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys
    130

<210> SEQ ID NO 60
<211> LENGTH: 798
<212> TYPE: DNA
<213> ORGANISM: Artificial Sequence
<220> FEATURE:
```

-continued

```
<223> OTHER INFORMATION: Synthetic construct
<220> FEATURE:
<221> NAME/KEY: CDS
<222> LOCATION: (122)..(166)
<220> FEATURE:
<221> NAME/KEY: CDS
<222> LOCATION: (249)..(596)

<400> SEQUENCE: 60
aagcttatga atatgcaaat cctctgaatc tacatggtaa atataggttt gtctatacca      60
caaacagaaa acatgagat cacagttctc tctacagtta ctgagcacac aggacctcac     120 c atg gga tgg agc tgt atc atc ctc ttc ttg gta gca aca gct aca          166
  Met Gly Trp Ser Cys Ile Ile Leu Phe Leu Val Ala Thr Ala Thr
   1               5                  10                  15 ggtaaggggc tcacagtagc aggcttgagg tctggacata tatatgggtg acaatgacat     226
ccactttgcc tttctctcca ca ggt gtc cac tcc gag gtg cag ctg gtc gag      278
                          Gly Val His Ser Glu Val Gln Leu Val Glu
                                              20                  25 tct ggg gga ggc tta gtg cag cct gga ggg tcc ctg aaa ctc tcc tgt       326
Ser Gly Gly Gly Leu Val Gln Pro Gly Gly Ser Leu Lys Leu Ser Cys
              30                  35                  40 gca gcc tct gga ttc act ttc agt agc tat ggc atg tct tgg gtt cgc       374
Ala Ala Ser Gly Phe Thr Phe Ser Ser Tyr Gly Met Ser Trp Val Arg
            45                  50                  55 cag act cca gac aag agg ctg gaa ttg gtc gca agc atc aat agt aat       422
Gln Thr Pro Asp Lys Arg Leu Glu Leu Val Ala Ser Ile Asn Ser Asn
        60                  65                  70 ggt ggt agc acc tat tat cca gac agt gtg aag ggc cga ttc acc atc       470
Gly Gly Ser Thr Tyr Tyr Pro Asp Ser Val Lys Gly Arg Phe Thr Ile
    75                  80                  85 tcc aga gac aat gcc aag aac acc ctg tac ctg caa atg agc agt ctg       518
Ser Arg Asp Asn Ala Lys Asn Thr Leu Tyr Leu Gln Met Ser Ser Leu
 90                  95                 100                 105 aag tct gag gac aca gcc atg tat tac tgt gca agt ggt gac tac tgg       566
Lys Ser Glu Asp Thr Ala Met Tyr Tyr Cys Ala Ser Gly Asp Tyr Trp
                110                 115                 120 ggc caa ggc tcc act ctc aca gtc tcc tca ggtgagtcct tacaacctct         616
Gly Gln Gly Ser Thr Leu Thr Val Ser Ser
                125                 130 ctcttctatt cagcttaaat agattttact gcatttgttg gggggaaat gtgtgtatct      676 gaatttcagg tcatgaagga ctagggacac cttgggagtc agaaagggtc attgggagcc     736
cgggctgatg cagacagaca tcctcagctc ccagacttca tggccagaga tttataggat     796
cc                                                                    798

<210> SEQ ID NO 61
<211> LENGTH: 131
<212> TYPE: PRT
<213> ORGANISM: Artificial Sequence
<220> FEATURE:
<223> OTHER INFORMATION: Synthetic construct

<400> SEQUENCE: 61

Met Gly Trp Ser Cys Ile Ile Leu Phe Leu Val Ala Thr Ala Thr Gly
 1               5                  10                  15

Val His Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
```

```
                    50                  55                  60
Glu Leu Val Ala Ser Ile Asn Ser Asn Gly Gly Ser Thr Tyr Tyr Pro
 65                  70                  75                  80

Asp Ser Val Lys Gly Arg Phe Thr Ile Ser Arg Asp Asn Ala Lys Asn
                     85                  90                  95

Thr Leu Tyr Leu Gln Met Ser Ser Leu Lys Ser Glu Asp Thr Ala Met
                100                 105                 110

Tyr Tyr Cys Ala Ser Gly Asp Tyr Trp Gly Gln Gly Ser Thr Leu Thr
                115                 120                 125

Val Ser Ser
130

<210> SEQ ID NO 62
<211> LENGTH: 99
<212> TYPE: PRT
<213> ORGANISM: Mus musculus

<400> SEQUENCE: 62

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Tyr
                 20                  25                  30

Gly Met Ser Trp Val Arg Gln Thr Pro Asp Lys Arg Leu Glu Trp Val
             35                  40                  45

Ala Thr Ile Ser Ser Gly Gly Ser Tyr Thr Tyr Tyr Pro Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Arg

<210> SEQ ID NO 63
<211> LENGTH: 112
<212> TYPE: PRT
<213> ORGANISM: Artificial Sequence
<220> FEATURE:
<223> OTHER INFORMATION: Synthetic construct

<400> SEQUENCE: 63

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val Tyr Ser
                 20                  25                  30

Asn Gly Asp Thr Tyr Leu His Trp Tyr Leu Gln Lys Pro Gly Gln Ser
             35                  40                  45

Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Trp Thr Phe Gly Gln Gly Thr Lys Val Glu Ile Lys
                100                 105                 110

<210> SEQ ID NO 64
<211> LENGTH: 112
<212> TYPE: PRT
```

```
<213> ORGANISM: Artificial Sequence
<220> FEATURE:
<223> OTHER INFORMATION: Synthetic construct

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: Synthetic construct

<400> SEQUENCE: 65

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

<210> SEQ ID NO 66
<211> LENGTH: 100
<212> TYPE: PRT
<213> ORGANISM: Artificial Sequence
<220> FEATURE:
<223> OTHER INFORMATION: Synthetic construct

<400> SEQUENCE: 66

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100
```

<210> SEQ ID NO 67
<211> LENGTH: 12
<212> TYPE: PRT
<213> ORGANISM: Artificial Sequence
<220> FEATURE:
<223> OTHER INFORMATION: Synthetic construct

<400> SEQUENCE: 67

```
Trp Thr Phe Gly Gln Gly Thr Lys Val Glu Ile Lys
 1               5                  10
```

<210> SEQ ID NO 68
<211> LENGTH: 112
<212> TYPE: PRT
<213> ORGANISM: Artificial Sequence
<220> FEATURE:
<223> OTHER INFORMATION: Synthetic construct

<400> SEQUENCE: 68

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
                 20                  25                  30

Gly Met Ser Trp Val Arg Gln Thr Pro Asp Lys Arg Leu Glu Leu Val
             35                  40                  45

Ala Ser Ile Asn Ser Asn Gly Gly Ser Thr Tyr Tyr Pro Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Ser Gly Asp Tyr Trp Gly Gln Gly Ser Leu Thr Val Ser Ser
            100                 105                 110
```

<210> SEQ ID NO 69
<211> LENGTH: 112
<212> TYPE: PRT
<213> ORGANISM: Artificial Sequence
<220> FEATURE:
<223> OTHER INFORMATION: Synthetic construct

<400> SEQUENCE: 69

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Trp Val
             35                  40                  45

Ala Ser Ile Asn Ser Asn Gly Gly Ser Thr Tyr Tyr Pro Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ala Arg Gly Asp Tyr Trp Gly Gln Gly Thr Thr Val Thr Val Ser Ser
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: Synthetic construct

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Synthetic construct

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Trp Gly Gln Gly Thr Thr Val Thr Val Ser Ser
            100                 105                 110

<210> SEQ ID NO 72
<211> LENGTH: 98
<212> TYPE: PRT
<213> ORGANISM: Artificial Sequence
<220> FEATURE:
<223> OTHER INFORMATION: Synthetic construct

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                    20                  25                  30
Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 73
<211> LENGTH: 20
<212> TYPE: PRT
<213> ORGANISM: Artificial Sequence
<220> FEATURE:
<223> OTHER INFORMATION: Synthetic construct

<400> SEQUENCE: 73

Tyr Tyr Tyr Tyr Tyr Gly Met Asp Val Trp Gly Gln Gly Thr Thr Val
1               5                   10                  15

Thr Val Ser Ser
            20

<210> SEQ ID NO 74
<211> LENGTH: 635
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (122)..(166)
<220> FEATURE:
<221> NAME/KEY: CDS
<222> LOCATION: (249)..(596)

<400> SEQUENCE: 74
aagcttatga atatgcaaat cctctgaatc tacatggtaa atataggttt gtctatacca      60
caaacagaaa acatgagat cacagttctc tctacagtta ctgagcacac aggacctcac     120 c atg gga tgg agc tgt atc atc ctc ttc ttg gta gca aca gct aca        166
  Met Gly Trp Ser Cys Ile Ile Leu Phe Leu Val Ala Thr Ala Thr
  1               5                   10                  15 ggtaaggggc tcacagtagc aggcttgagg tctggacata tatatgggtg acaatgacat    226
ccactttgcc tttctctcca ca ggt gtc cac tcc gat att gtg atg acc caa    278
                         Gly Val His Ser Asp Ile Val Met Thr Gln
                                                  20              25 tct cca ctc tcc ctg cct gtc act cct ggt gag cct gcc tcc atc tct     326
Ser Pro Leu Ser Leu Pro Val Thr Pro Gly Glu Pro Ala Ser Ile Ser
                30                  35                  40 tgc aga tct agt cag agc ctt gta tat agt aat gga gac acc tat tta     374
Cys Arg Ser Ser Gln Ser Leu Val Tyr Ser Asn Gly Asp Thr Tyr Leu
        45                  50                  55 cat tgg tac ctg cag aag cca ggc cag tct cca cag ctc ctg atc tac     422
His Trp Tyr Leu Gln Lys Pro Gly Gln Ser Pro Gln Leu Leu Ile Tyr
60                  65                  70 aaa gtt tcc aac cga ttt tct ggg gtc cca gac agg ttc agt ggc agt     470
Lys Val Ser Asn Arg Phe Ser Gly Val Pro Asp Arg Phe Ser Gly Ser
    75                  80                  85 gga tca ggg aca gat ttc aca ctc aag atc agc aga gtg gag gct gag     518
Gly Ser Gly Thr Asp Phe Thr Leu Lys Ile Ser Arg Val Glu Ala Glu
```

```
                  90                  95                  100                 105
gat gtg gga gtt tat tac tgc tct caa agt aca cat gtt cct tgg acg              566
Asp Val Gly Val Tyr Tyr Cys Ser Gln Ser Thr His Val Pro Trp Thr
                    110                 115                 120 ttc ggc caa ggc acc aag gtg gaa atc aaa cgtgagtaga atttaaactt                616
Phe Gly Gln Gly Thr Lys Val Glu Ile Lys
            125                 130 tgcttcctca gttggatcc                                                         635

<210> SEQ ID NO 75
<211> LENGTH: 131
<212> TYPE: PRT
<213> ORGANISM: Artificial Sequence
<220> FEATURE:
<223> OTHER INFORMATION: Synthetic construct

<400> SEQUENCE: 75

Met Gly Trp Ser Cys Ile Ile Leu Phe Leu Val Ala Thr Ala Thr Gly
 1               5                   10                  15

Val His Ser Asp Ile Val Met Thr Gln Ser Pro Leu Ser Leu Pro Val
                20                  25                  30

Thr Pro Gly Glu Pro Ala Ser Ile Ser Cys Arg Ser Ser Gln Ser Leu
            35                  40                  45

Val Tyr Ser Asn Gly Asp Thr Tyr Leu His Trp Tyr Leu Gln Lys Pro
        50                  55                  60

Gly Gln Ser Pro Gln Leu Leu Ile Tyr Lys Val Ser Asn Arg Phe Ser
 65                 70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Ser Thr His Val Pro Trp Thr Phe Gly Gln Gly Thr Lys Val
        115                 120                 125

Glu Ile Lys
    130

<210> SEQ ID NO 76
<211> LENGTH: 5561
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (2138)..(2455)

<400> SEQUENCE: 76
ggatcctggc agagtctcac agatgcttct gagacaacat tgctttcaa aaaatgaacc            60 acacacatcc taaagatctc agccacttcc catgtttcat tttatgttac agcaaacatc          120
acaacaatca ttcctacaga tcaccactgc atgtgatcaa taaaatagtt tttgcaacaa          180
tgctacttat gataatcatc ttttattgtt tacaaatact gctttacaat agttattcgg          240
ttgcactgtt catattagat ttccaattag ctcacttagg aacataagtc cctcgaacag          300
ctcagtcatc tttttcattc ctgtttctat cccctacatc tctttccttt gcagacgact          360
atctcctaca ctgaaacagg aaagctagct ttttttttc agtgctattt aattatttca           420
atatcctctc atcaaatgta tttaaataac aaaagctcaa ccaaaaagaa agaaatatgt          480
aattctttca gagtaaaaat cacacccatg acctggccac tgagggcttg atcaattcac          540
```

```
                                            -continued tttgaatttg gcattaaata ccattaaggt atattaactg attttaaaat aagatatatt    600
cgtgaccatg ttttaacttt tcaaaaatgt agctgccagt gtgtgatttt atttcagttg    660
tacaaaatat ctaaacctat agcaatgtga ttaataaaaa cttaaacata ttttccagta    720
ccttaattct gtgataggaa aattttaatc tgagtatttt aatttcataa tctctaaaat    780
agtttaatga tttgtcattg tgttgctctc gtttacccca gctgatctca aaagtgatat    840
ttaaggagat tattttggtc tgcaacaact tgataggact attttagggc cttttaaag     900 ctctattaaa actaacttac aacgattcaa aactgtttta aactatttca aaatgatttt    960
agagcctttt gaaaactctt ttaaacactt tttaaactct attaaaacta ataagataac   1020
ttgaaataat tttcatgtca aatacattaa ctgtttaatg tttaaatgcc agatgaaaaa   1080
tgtaaagcta tcaagaattc acccagatag gagtatcttc atagcatgtt tttccctgct   1140
tattttccag tgatcacatt attttgctac catggttatt ttatacaatt atctgaaaaa   1200
aattagttat gaagattaaa agagaagaaa atattaaaca taagagattc agtctttcat   1260
gttgaactgc ttggttaaca gtgaagttag ttttaaaaaa aaaaaaaact atttctgtta   1320
tcacctgact tctccctatc tgttgacttc tcccagcaaa agattcttat tttacatttt   1380
aactactgct ctcccaccca acgggtggaa tcccccagag ggggatttcc aagaggccac   1440
ctggcagttg ctgagggtca gaagtgaagc tagccacttc ctcttaggca ggtggccaag   1500
attacagttg acctctcctg gtatggctga aaattgctgc atatggttac aggccttgag   1560
gcctttggga gggcttagag agttgctgga acagtcagaa ggtggagggg ctgacaccac   1620
ccaggcgcag aggcagggct cagggcctgc tctgcaggga ggttttagcc cagcccagcc   1680
aaagtaaccc ccgggagcct gttatcccag cacagtcctg gaagaggcac aggggaaata   1740
aaagcggacg gaggctttcc ttgactcagc cgctgcctgg tcttcttcag acctgttctg   1800
aattctaaac tctgaggggg tcggatgacg tggccattct ttgcctaaag cattgagttt   1860
actgcaaggt cagaaaagca tgcaaagccc tcagaatggc tgcaaagagc tccaacaaaa   1920
caatttagaa cttattaag  gaatagggggg aagctaggaa gaaactcaaa acatcaagat   1980
tttaaatacg cttcttggtc tccttgctat aattatctgg gataagcatg ctgttttctg   2040
tctgtcccta acatgccctg tgattatccg caaacaacac acccaagggc agaactttgt   2100
tacttaaaca ccatcctgtt tgcttctttc ctcagga act gtg gct gca cca tct    2155
                                         Thr Val Ala Ala Pro Ser
                                           1               5 gtc ttc atc ttc ccg cca tct gat gag cag ttg aaa tct gga act gcc    2203
Val Phe Ile Phe Pro Pro Ser Asp Glu Gln Leu Lys Ser Gly Thr Ala
         10                  15                  20 tct gtt gtg tgc ctg ctg aat aac ttc tat ccc aga gag gcc aaa gta    2251
Ser Val Val Cys Leu Leu Asn Asn Phe Tyr Pro Arg Glu Ala Lys Val
     25                  30                  35 cag tgg aag gtg gat aac gcc ctc caa tcg ggt aac tcc cag gag agt    2299
Gln Trp Lys Val Asp Asn Ala Leu Gln Ser Gly Asn Ser Gln Glu Ser
 40                  45                  50 gtc aca gag cag gac agc aag gac agc acc tac agc ctc agc agc acc    2347
Val Thr Glu Gln Asp Ser Lys Asp Ser Thr Tyr Ser Leu Ser Ser Thr
 55                  60                  65                  70 ctg acg ctg agc aaa gca gac tac gag aaa cac aaa gtc tac gcc tgc    2395
Leu Thr Leu Ser Lys Ala Asp Tyr Glu Lys His Lys Val Tyr Ala Cys
             75                  80                  85 gaa gtc acc cat cag ggc ctg agc tcg ccc gtc aca aag agc ttc aac    2443
Glu Val Thr His Gln Gly Leu Ser Ser Pro Val Thr Lys Ser Phe Asn
         90                  95                 100
```

| | |
|---|---|
| agg gga gag tgt tagagggaga agtgccccca cctgctcctc agttccagcc<br>Arg Gly Glu Cys<br>    105 | 2495 |
| tgaccccctc ccatcctttg gcctctgacc cttttttccac aggggaccta cccctattgc | 2555 |
| ggtcctccag ctcatctttc acctcacccc cctcctcctc cttggcttta attatgctaa | 2615 |
| tgttggagga gaatgaataa ataaagtgaa tctttgcacc tgtggtttct ctctttcctc | 2675 |
| atttaataat tattatctgt tgttttacca actactcaat ttctcttata agggactaaa | 2735 |
| tatgtagtca tcctaaggcg cataaccatt tataaaaatc atccttcatt ctattttacc | 2795 |
| ctatcatcct ctgcaagaca gtcctccctc aaacccacaa gccttctgtc ctcacagtcc | 2855 |
| cctgggccat ggtaggagag acttgcttcc ttgttttccc ctcctcagca agccctcata | 2915 |
| gtccttttta agggtgacag gtcttacagt catatatcct ttcattcaat tccctgagaa | 2975 |
| tcaaccaaag caaattttc aaaagaagaa acctgctata aagagaatca ttcattgcaa | 3035 |
| catgatataa aataacaaca caataaaagc aattaaataa acaaacaata gggaaatgtt | 3095 |
| taagttcatc atggtactta gacttaatgg aatgtcatgc cttatttaca ttttaaaca | 3155 |
| ggtactgagg gactcctgtc tgccaagggc cgtattgact actttccaca acctaattta | 3215 |
| atccacacta tactgtgaga ttaaaaacat tcattaaaat gttgcaaagg ttctataaag | 3275 |
| ctgagagaca aatatattct ataactcagc aatcccactt ctagatgact gagtgtcccc | 3335 |
| acccaccaaa aaactatgca agaatgttca aagcagcttt atttacaaaa gccaaaaatt | 3395 |
| ggaaatagcc cgattgtcca acaatagaat gagttattaa actgtggtat gtttatacat | 3455 |
| tagaatacc aatgaggaga attaacaagc tacaactata cctactcaca cagatgaatc | 3515 |
| tcataaaaat aatgttacat aagagaaact caatgcaaaa gatatgttct gtatgttttc | 3575 |
| atccatataa agttcaaaac caggtaaaaa taaagttaga aatttggatg gaaattactc | 3635 |
| ttagctgggg gtgggcgagt tagtgcctgg gagaagacaa gaaggggctt ctggggtctt | 3695 |
| ggtaatgttc tgttcctcgt gtggggttgt gcagttatga tctgtgcact gttctgtata | 3755 |
| cacattatgc ttcaaaataa cttcacataa agaacatctt atacccagtt aatagataga | 3815 |
| agaggaataa gtaataggtc aagaccatgc agctggtaag tgggggggcc tgggatcaaa | 3875 |
| tagctacctg cctaatgctc ccctcttgag ccctgaatga gtctgccttc cagggctcaa | 3935 |
| ggtgctcaac aaaacaacag gcctgctatt ttcctggcat ctgtgccctg tttggctagc | 3995 |
| taggagcaca catacataga aattaaatga aacagacctt cagcaagggg acagaggaca | 4055 |
| gaattaaacct tgcccagaca ctggaaaccc atgtatgaac actcacatgt ttgggaaggg | 4115 |
| ggaagggcac atgtaaatga ggactcttcc tcattctatg gggcactctg gccctgcccc | 4175 |
| tctcagctac tcatccatcc aacacacctt tctaagtacc tctctctgcc tacactctga | 4235 |
| aggggttcag gagtaactaa cacagcatcc cttccctcaa atgactgacc atcccttgtt | 4295 |
| cctgctttgt ttttctttcc agtcagtact gggaaagtgg ggaaggacag tcatggaaaa | 4355 |
| actacataag gaagcacctt gcccttctgc ctcttgagaa tgttgatgag tatcaaatct | 4415 |
| ttcaaacttt ggaggtttga gtaggggtga gactcagtaa tgtcccttcc aatgacatga | 4475 |
| acttgctcac tcatccctgg gggccaaatt gaacaatcaa aggcaggcat aatccagtta | 4535 |
| tgaattcaaa ccttcttctc agaagataac actctgaagg gaaacccacc cataacctaa | 4595 |
| gcaagtgaag acaggtgctg caggtggaat tgtgtccttc aaaaaggtat gctcaactcc | 4655 |
| ttgctcttgg tactcataaa tgggtcacat aaatgtgact ttatttggaa atagggtctt | 4715 |
| tgcagaggta atcaagtcaa aattaggtca tactgaaatg tttgtgagga tgcggtgaaa | 4775 |

-continued

```
atggatcatt catatattgc tggtgggaat ataaaagggt atagctactc tagaaaatag    4835
ttgtcagttt cttgaaaaac taaacaaaag acacctacca tatgacccag gaattgtact    4895
ccttgggaat ttaccccccag gaaataaaaa cttatgtcca cacagaaccc atacatgatt   4955
gttcacagca gctttatttg ttgtagccaa agctagaaag agccaaccca tccctcaata    5015
ggcaactagc ctaacaaatt gtaatatatc catgccatag aatgctatga ggcaataaaa    5075
aggaacgaag tgttgataca gagaactgga gtgattctga aggactttct actgagtgaa    5135
aaaagccaat ctgaaagggt cacataccat gtgattcctt ttatgtaaca ttgttgaagt    5195
gacaaaatta tagggataga gaacagattc tggttgccag gggttagggt ggtgagaaa    5255 gaagagtagg cgaaactata aagggagatc tttgtgatca tgggataaat ctgtatcttg    5315
attgcagtgg tagttgcagg catctagaca tgtgataaaa tgacatagaa ctgtacacac    5375 ttatttatc aatgtcaaat tcttggtttt aatatcgtac tgtaattacg taagaagtaa     5435
ccaacaggag aaactgggtg caggacacat cagacctctg tgctttatat cctgtctttg    5495
ctactttctg tgaatctata attatttcca aataattttt ttaaactttt tttttatgct    5555
ggatcg                                                              5561
```

```
<210> SEQ ID NO 77
<211> LENGTH: 106
<212> TYPE: PRT
<213> ORGANISM: Artificial Sequence
<220> FEATURE:
<223> OTHER INFORMATION: Synthetic construct

<400> SEQUENCE: 77
```

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

```
<210> SEQ ID NO 78
<211> LENGTH: 2027
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (230)..(523)
<220> FEATURE:
<221> NAME/KEY: CDS
<222> LOCATION: (920)..(955)
<220> FEATURE:
<221> NAME/KEY: CDS
<222> LOCATION: (1074)..(1403)
<220> FEATURE:
<221> NAME/KEY: CDS
<222> LOCATION: (1501)..(1821)

<400> SEQUENCE: 78
```

```
ggatcctcta gattgagctt tctggggcag gccaggcctg accttggctg ggggcaggga      60
gggggctaag gtgacgcagg tggcgccagc caggtgcaca cccaatgccc atgagcccag     120
acactggacc ctgcatggac catcgcggat agacaagaac cgagggcct ctgcgccctg      180 ggcccagctc tgtcccacac cgcggtcaca tggcaccacc tctcttgca gct tcc acc    238
                                                        Ala Ser Thr
                                                         1 aag ggc cca tcc gtc ttc ccc ctg gcg ccc tgc tcc aga tcg acc tcc      286
Lys Gly Pro Ser Val Phe Pro Leu Ala Pro Cys Ser Arg Ser Thr Ser
     5              10                  15 gag agc aca gcc gcc ctg ggc tgc ctg gtc aag gac tac ttc ccc gaa      334
Glu Ser Thr Ala Ala Leu Gly Cys Leu Val Lys Asp Tyr Phe Pro Glu
 20              25                  30                  35 ccg gtg acg gtg tcg tgg aac tca ggc gcc ctg acc agc ggc gtg cac      382
Pro Val Thr Val Ser Trp Asn Ser Gly Ala Leu Thr Ser Gly Val His
                 40                  45                  50 acc ttc ccg gct gtc cta cag tcc tca gga ctc tac tcc ctc agc agc      430
Thr Phe Pro Ala Val Leu Gln Ser Ser Gly Leu Tyr Ser Leu Ser Ser
                     55                  60                  65 gtg gtg acc gtg ccc tcc agc agc ttg ggc acg aag acc tac acc tgc      478
Val Val Thr Val Pro Ser Ser Ser Leu Gly Thr Lys Thr Tyr Thr Cys
             70                  75                  80 aac gta gat cac aag ccc agc aac acc aag gtg gac aag aga gtt          523
Asn Val Asp His Lys Pro Ser Asn Thr Lys Val Asp Lys Arg Val
                 85                  90                  95 ggtgagaggc cagcacaggg agggagggtg tctgctggaa gccaggctca gccctcctgc     583
ctggacgcac cccggctctg cagccccagc ccagggcagc aaggcatgcc ccatctgtct     643
cctcacccgg aggcctctga ccaccccact catgctcagg gagagggtct tctggatttt     703
tccaccaggc tccgggcagc cacaggctgg atgcccctac ccaggccct gcgcatacag      763 gggcaggtgc tgcgctcaga cctgccaaga gccatatccg ggaggaccct gcccctgacc     823
taagcccacc ccaaaggcca aactctccac tccctcagct cagacacctt ctctcctccc     883
agatcgatct gagtaactcc caatcttctc tctgca gag tcc aaa tat ggt ccc      937
                                        Glu Ser Lys Tyr Gly Pro
                                                            100 ccg tgt ccc cca tgc cca ggtaagccaa cccaggcctc gccctccagc             985
Pro Cys Pro Pro Cys Pro
105                 110 tcaaggcggg acaggtgccc tagagtagcc tgcatccagg acaggcccc agccgggtgc     1045 tgacgcatcc acctccatct cttcctca gca cct gag ttc ctg ggg gga cca      1097
                                 Ala Pro Glu Phe Leu Gly Gly Pro
                                                         115 tca gtc ttc ctg ttc ccc cca aaa ccc aag gac act ctc atg atc tcc     1145
Ser Val Phe Leu Phe Pro Pro Lys Pro Lys Asp Thr Leu Met Ile Ser
    120                 125                 130 cgg acc cct gag gtc acg tgc gtg gtg gtg gac gtg agc cag gaa gac     1193
Arg Thr Pro Glu Val Thr Cys Val Val Val Asp Val Ser Gln Glu Asp
135                 140                 145                 150 ccc gag gtc cag ttc aac tgg tac gtg gat ggc gtg gag gtg cat aat     1241
Pro Glu Val Gln Phe Asn Trp Tyr Val Asp Gly Val Glu Val His Asn
                155                 160                 165 gcc aag aca aag ccg cgg gag gag cag ttc aac agc acg tac cgt gtg     1289
Ala Lys Thr Lys Pro Arg Glu Glu Gln Phe Asn Ser Thr Tyr Arg Val
                    170                 175                 180 gtc agc gtc ctc acc gtc ctg cac cag gac tgg ctg aac ggc aag gag     1337
Val Ser Val Leu Thr Val Leu His Gln Asp Trp Leu Asn Gly Lys Glu
            185                 190                 195
```

```
tac aag tgc aag gtc tcc aac aaa ggc ctc ccg tcc tcc atc gag aaa    1385
Tyr Lys Cys Lys Val Ser Asn Lys Gly Leu Pro Ser Ser Ile Glu Lys
    200                 205                 210 acc atc tcc aaa gcc aaa ggtgggaccc acggggtgcg agggccacat            1433
Thr Ile Ser Lys Ala Lys
215                 220 ggacagaggt cagctcggcc caccctctgc cctgggagtg accgctgtgc caacctctgt   1493 ccctaca ggg cag ccc cga gag cca cag gtg tac acc ctg ccc cca tcc    1542
        Gly Gln Pro Arg Glu Pro Gln Val Tyr Thr Leu Pro Pro Ser
                        225                 230 cag gag gag atg acc aag aac cag gtc agc ctg acc tgc ctg gtc aaa    1590
Gln Glu Glu Met Thr Lys Asn Gln Val Ser Leu Thr Cys Leu Val Lys
235                 240                 245                 250 ggc ttc tac ccc agc gac atc gcc gtg gag tgg gag agc aat ggg cag    1638
Gly Phe Tyr Pro Ser Asp Ile Ala Val Glu Trp Glu Ser Asn Gly Gln
                255                 260                 265 ccg gag aac aac tac aag acc acg cct ccc gtc ctc gat tcc gac ggc    1686
Pro Glu Asn Asn Tyr Lys Thr Thr Pro Pro Val Leu Asp Ser Asp Gly
            270                 275                 280 tcc ttc ttc ctc tac agc agg cta acc gtg gac aag agc agc tgg cag    1734
Ser Phe Phe Leu Tyr Ser Arg Leu Thr Val Asp Lys Ser Ser Trp Gln
        285                 290                 295 gag ggg aat gtc ttc tca tgc tcc gtg atg cat gag gct ctg cac aac    1782
Glu Gly Asn Val Phe Ser Cys Ser Val Met His Glu Ala Leu His Asn
    300                 305                 310 cac tac aca cag aag agc ctc tcc ctg tct ctg ggt aaa tgagtgccag     1831
His Tyr Thr Gln Lys Ser Leu Ser Leu Ser Leu Gly Lys
315                 320                 325 ggccggcaag cccccgctcc ccgggctctc ggggtcgcgc gaggatgctt ggcacgtacc   1891
ccgtctacat acttcccagg cacccagcat ggaaataaag cacccaccac tgccctgggc  1951
ccctgtgaga ctgtgatggt tctttccacg ggtcaggccg agtctgaggc ctgagtgaca  2011
tgagggaggc agatcc                                                  2027

<210> SEQ ID NO 79
<211> LENGTH: 327
<212> TYPE: PRT
<213> ORGANISM: Artificial Sequence
<220> FEATURE:
<223> OTHER INFORMATION: Synthetic construct

<400> SEQUENCE: 79

Ala Ser Thr Lys Gly Pro Ser Val Phe Pro Leu Ala Pro Cys Ser Arg
 1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Ser Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 80
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: His, Asn, Gln, Lys or Arg
<220> FEATURE:
<221> NAME/KEY: MOD_RES
<222> LOCATION: (2)
<223> OTHER INFORMATION: Asn or Gln
<220> FEATURE:
<221> NAME/KEY: MOD_RES
<222> LOCATION: (5)
<223> OTHER INFORMATION: Ala, Val, Leu, norleucine, Met, Phe or Ile
<220> FEATURE:
<221> NAME/KEY: MOD_RES
<222> LOCATION: (8)
<223> OTHER INFORMATION: Ala, Val, Leu, Ser or Ile
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Glu or Asp

<400> SEQUENCE: 80

Xaa Xaa Lys Leu Xaa Phe Phe Xaa Xaa Xaa
1               5                   10
```